(12) United States Patent
Meyer et al.

(10) Patent No.: US 7,056,742 B2
(45) Date of Patent: Jun. 6, 2006

(54) HIGH LEVEL PRODUCTION OF ARBUTIN IN GREEN PLANTS

(75) Inventors: Knut Meyer, Wilmington, DE (US); Paul V. Viitanen, West Chester, PA (US); Dennis Flint, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/462,162

(22) Filed: Jun. 16, 2003

(65) Prior Publication Data

US 2004/0261147 A1    Dec. 23, 2004

(51) Int. Cl.
*C12N 15/82*    (2006.01)
*C12N 15/90*    (2006.01)
*A01H 5/00*    (2006.01)

(52) U.S. Cl. ..................... 435/468; 800/278
(58) Field of Classification Search .......... 536/23.1; 800/295, 278; 435/320.1, 69.1, 69.7, 419, 435/468
See application file for complete search history.

(56) References Cited

U.S. PATENT DOCUMENTS

| | | | |
|---|---|---|---|
| 3,201,385 A | 8/1965 | Jarrett | 424/62 |
| 5,776,736 A | 7/1998 | Frost et al. | 435/108 |
| 6,210,937 B1 | 4/2001 | Ward et al. | 435/146 |
| 6,306,376 B1 | 10/2001 | Philippe | 424/62 |
| 6,388,103 B1 | 5/2002 | Lee et al. | 549/417 |

FOREIGN PATENT DOCUMENTS

| | | | |
|---|---|---|---|
| DE | WO200210210 A2 | * | 5/2002 |
| WO | WO 00/73484 A1 | | 12/2000 |
| WO | WO 01/07631 A2 | | 2/2001 |
| WO | WO 01/59140 | * | 8/2001 |
| WO | WO 01/94607 | * | 12/2001 |

OTHER PUBLICATIONS

Bertani et al. Microbiol. 2001. vol. 147. pp. 1611-1620.*
Viale et al. FEBS 3121. 1985. vol. 192(2). pp. 283-288.*
Siebert et al. Plant Physiology. 1996. vol. 112. pp. 811-819.*
Joachim Arend et al., Hydroquinone:O-glucosyltransferase from cultivated Rauvolfia cells: enrichment and partial amino acid sequences, Phytochemistry, vol. 53:187-193, 2000.
Joachim Arend et al., Utilizing Genetically Engineered Bacteria to Produce Plant-Specific Glucosides, Biotech. Bioeng., vol.v76(2): 126-131, 2001.
Tobias Hefner et al., Arbutin Synthase, a Novel Member of the NRD 1β Glycosyltransferase Family, is a Unique Multifunctional Enzyme Converting Various Natural Products and Xenobiotics, Bioorganic & Medicinal Chemistry, vol. 10:1731-1741, 2002.
Ningqing Ran et al., Benzene-Free Synthesis of Hydroquinone, J. Am. Chem. Soc., vol. 123:10927-10934, 2001.
Marion Siebert et al., Genetic Engineering of Plant Secondary Metabolism, Plant Physiol., vol. 112:811-819, 1996.
Alan Berry, Improving Production of Aromatic Compounds In *Escherichia coli* by Metabolic Engineering, TIBTECH Reviews, vol. 14:250-256, Jul. 1996.
Johannes Bongaerts et al., Metabolic Engineering for Microbial Production of Aromatic Amino Acids and Derived Compounds, Metabolic Engineering, vol. 3:289-300, 2001.
Matthew Tatarko et al., Disruption of a Global Regulatory Gene to Enhance Central Carbon Flux into Phenylalanine Biosynthesis in *Escherichia coli*, Current Microbiology, vol. 43:26-32, 2001.

* cited by examiner

*Primary Examiner*—Ashwin Mehta

(57) ABSTRACT

This invention relates to methods and materials to produce hydroquinone glucoside in genetically modified green plants and microorganisms.

12 Claims, 7 Drawing Sheets

ID NO:38)(cytosolic) for the increased production of pHBA. In

SEQUENCE LISTING

```
<160> NUMBER OF SEQ ID NOS: 54

<210> SEQ ID NO 1
<211> LENGTH: 24
<212> TYPE: PRT
<213> ORGANISM: Candida parapsilosis

<400> SEQUENCE: 1

Ala Val Gln Ala Pro Ser Lys Thr Tyr Gly Phe Gln Lys Ala Pro Ile
1               5                   10                  15

Gln Leu Thr Phe Val Val Val Gly
            20

<210> SEQ ID NO 2
<211> LENGTH: 7
<212> TYPE: PRT
<213> ORGANISM: Candida parapsilosis

<400> SEQUENCE: 2

Asn Pro Thr Tyr Thr Tyr Pro
1               5
```

```
<210> SEQ ID NO 3
<211> LENGTH: 14
<212> TYPE: PRT
<213> ORGANISM: Candida parapsilosis

<400> SEQUENCE: 3

Gln Tyr Val Gly Asp Val Ile Val Gly Tyr Asp Gly Val Arg
1               5                   10

<210> SEQ ID NO 4
<211> LENGTH: 13
<212> TYPE: PRT
<213> ORGANISM: Candida parapsilosis

<400> SEQUENCE: 4

Ala Leu Leu Thr Gly Asp Ser Ser Gly Ala Tyr Asp Thr
1               5                   10

<210> SEQ ID NO 5
<211> LENGTH: 32
<212> TYPE: DNA
<213> ORGANISM: artificial sequence
<220> FEATURE:
<223> OTHER INFORMATION: Primer 1
<220> FEATURE:
<221> NAME/KEY: misc_feature
<222> LOCATION: (6)..(6)
<223> OTHER INFORMATION: N=inosine
<220> FEATURE:
<221> NAME/KEY: misc_feature
<222> LOCATION: (9)..(9)
<223> OTHER INFORMATION: N=inosine
<220> FEATURE:
<221> NAME/KEY: misc_feature
<222> LOCATION: (12)..(12)
<223> OTHER INFORMATION: R= A or G
<220> FEATURE:
<221> NAME/KEY: misc_feature
<222> LOCATION: (15)..(15)
<223> OTHER INFORMATION: n=inosine
<220> FEATURE:
<221> NAME/KEY: misc_feature
<222> LOCATION: (18)..(18)
<223> OTHER INFORMATION: n=inosine
<220> FEATURE:
<221> NAME/KEY: misc_feature
<222> LOCATION: (19)..(19)
<223> OTHER INFORMATION: W= A or T
<220> FEATURE:
<221> NAME/KEY: misc_feature
<222> LOCATION: (20)..(20)
<223> OTHER INFORMATION: S= C or G
<220> FEATURE:
<221> NAME/KEY: misc_feature
<222> LOCATION: (21)..(21)
<223> OTHER INFORMATION: n=inosine
<220> FEATURE:
<221> NAME/KEY: misc_feature
<222> LOCATION: (24)..(24)
<223> OTHER INFORMATION: R= A or G
<220> FEATURE:
<221> NAME/KEY: misc_feature
<222> LOCATION: (27)..(27)
<223> OTHER INFORMATION: n=inosine
<220> FEATURE:
<221> NAME/KEY: misc_feature
<222> LOCATION: (30)..(30)
<223> OTHER INFORMATION: n=inosine

<400> SEQUENCE: 5
atggcngtnc argcnccnws naaracntan gg                             32
```

```
<210> SEQ ID NO 6
<211> LENGTH: 32
<212> TYPE: DNA
<213> ORGANISM: artificial sequence
<220> FEATURE:
<223> OTHER INFORMATION: Primer 2
<220> FEATURE:
<221> NAME/KEY: misc_feature
<222> LOCATION: (3)..(3)
<223> OTHER INFORMATION: R= A or G
<220> FEATURE:
<221> NAME/KEY: misc_feature
<222> LOCATION: (6)..(6)
<223> OTHER INFORMATION: R= A or G
<220> FEATURE:
<221> NAME/KEY: misc_feature
<222> LOCATION: (9)..(9)
<223> OTHER INFORMATION: n=inosine
<220> FEATURE:
<221> NAME/KEY: misc_feature
<222> LOCATION: (12)..(12)
<223> OTHER INFORMATION: n=inosine
<220> FEATURE:
<221> NAME/KEY: misc_feature
<222> LOCATION: (15)..(15)
<223> OTHER INFORMATION: D= A, G, or T
<220> FEATURE:
<221> NAME/KEY: misc_feature
<222> LOCATION: (18)..(18)
<223> OTHER INFORMATION: n=inosine
<220> FEATURE:
<221> NAME/KEY: misc_feature
<222> LOCATION: (21)..(21)
<223> OTHER INFORMATION: R= A or G
<220> FEATURE:
<221> NAME/KEY: misc_feature
<222> LOCATION: (24)..(24)
<223> OTHER INFORMATION: n=inosine
<220> FEATURE:
<221> NAME/KEY: misc_feature
<222> LOCATION: (27)..(27)
<223> OTHER INFORMATION: n=inosine
<220> FEATURE:
<221> NAME/KEY: misc_feature
<222> LOCATION: (30)..(30)
<223> OTHER INFORMATION: R= A or G

<400> SEQUENCE: 6
ccrtcrtanc cnacdatnac rtcnccnacr ta                              32

<210> SEQ ID NO 7
<211> LENGTH: 11
<212> TYPE: PRT
<213> ORGANISM: Candida parapsilosis

<400> SEQUENCE: 7

Met Ala Val Gln Ala Pro Ser Lys Thr Tyr Gly
1               5                   10

<210> SEQ ID NO 8
<211> LENGTH: 11
<212> TYPE: PRT
<213> ORGANISM: Candida parapsilosis

<400> SEQUENCE: 8

Tyr Val Gly Asp Val Ile Val Gly Tyr Asp Gly
1               5                   10

<210> SEQ ID NO 9
<211> LENGTH: 518
<212> TYPE: DNA
<213> ORGANISM: Candida parapsilosis
```

```
<220> FEATURE:
<221> NAME/KEY: misc_feature
<222> LOCATION: (24)..(24)
<223> OTHER INFORMATION: R= A or G
<220> FEATURE:
<221> NAME/KEY: misc_feature
<222> LOCATION: (489)..(489)
<223> OTHER INFORMATION: Y= C or T
<220> FEATURE:
<221> NAME/KEY: misc_feature
<222> LOCATION: (504)..(504)
<223> OTHER INFORMATION: W= A or T
<220> FEATURE:
<221> NAME/KEY: misc_feature
<222> LOCATION: (513)..(513)
<223> OTHER INFORMATION: Y= C or T

<400> SEQUENCE: 9
atggcggtgc aggcgccgtg gaaracgtac ggtttccaaa aggctccaat acaacttaca    60
tttgtcgttg taggtgccgg tctcggggga gtcgccgcta gtatttgcct cagattggca   120
ggccacagag tcattttatt agaagcagct actgaattgg gtgaagttgg agctggtatt   180
caaattccac caccatcaac caagatttta aaagcaattg gcgtattgga tgcagttgat   240
aaagtctcga ttcatccaca tgatatcttg gtcaagaaat ataaaggtga acttttatct   300
acgcaaaact tggtgcctta tgttctggag aaatacgatg gaatgtattt acatattcac   360
agggctgatt atcataaagt attggttgat agagccgaag aattgggggt tgaaatccat   420
acaaattcaa gagttgttga tattgatttt gaaaagcaa ctgtcactac tgcaactgga   480
aaacaatayg tcggcgatgt catwgtcggc taygatgg                            518

<210> SEQ ID NO 10
<211> LENGTH: 172
<212> TYPE: PRT
<213> ORGANISM: Candida parapsilosis

<400> SEQUENCE: 10

Met Ala Val Gln Ala Pro Trp Lys Thr Tyr Gly Phe Gln Lys Ala Pro
1               5                   10                  15

Ile Gln Leu Thr Phe Val Val Gly Ala Gly Leu Gly Gly Val Ala
            20                  25                  30

Ala Ser Ile Cys Leu Arg Leu Ala Gly His Arg Val Ile Leu Leu Glu
        35                  40                  45

Ala Ala Thr Glu Leu Gly Glu Val Gly Ala Gly Ile Gln Ile Pro Pro
    50                  55                  60

Pro Ser Thr Lys Ile Leu Lys Ala Ile Gly Val Leu Asp Ala Val Asp
65                  70                  75                  80

Lys Val Ser Ile His Pro His Asp Ile Leu Val Lys Lys Tyr Lys Gly
                85                  90                  95

Glu Leu Leu Ser Thr Gln Asn Leu Val Pro Tyr Val Leu Glu Lys Tyr
            100                 105                 110

Asp Gly Met Tyr Leu His Ile His Arg Ala Asp Tyr His Lys Val Leu
        115                 120                 125

Val Asp Arg Ala Glu Glu Leu Gly Val Glu Ile His Thr Asn Ser Arg
    130                 135                 140

Val Val Asp Ile Asp Phe Glu Lys Ala Thr Val Thr Thr Ala Thr Gly
145                 150                 155                 160

Lys Gln Tyr Val Gly Asp Val Ile Val Gly Tyr Asp
                165                 170
```

```
<210> SEQ ID NO 11
<211> LENGTH: 34
<212> TYPE: DNA
<213> ORGANISM: artificial sequence
<220> FEATURE:
<223> OTHER INFORMATION: Primer 3

<400> SEQUENCE: 11
ggccacgcgt cgactagtac ttttttttt tttt                               34

<210> SEQ ID NO 12
<211> LENGTH: 35
<212> TYPE: DNA
<213> ORGANISM: artificial sequence
<220> FEATURE:
<223> OTHER INFORMATION: Primer 4

<400> SEQUENCE: 12
ggttgataga gccgaagaat tgggggttga aatcc                             35

<210> SEQ ID NO 13
<211> LENGTH: 20
<212> TYPE: DNA
<213> ORGANISM: artificial sequence
<220> FEATURE:
<223> OTHER INFORMATION: Primer 5

<400> SEQUENCE: 13
ggccacgcgt cgactagtac                                              20

<210> SEQ ID NO 14
<211> LENGTH: 1526
<212> TYPE: DNA
<213> ORGANISM: Candida parapsilosis
<220> FEATURE:
<221> NAME/KEY: misc_feature
<222> LOCATION: (24)..(24)
<223> OTHER INFORMATION: R = A or G

<400> SEQUENCE: 14
atggcggtgc aggcgccgtg gaaracgtac ggtttccaaa aggctccaat acaacttaca    60
tttgtcgttg taggtgccgg tctcggggga gtcgccgcta gtatttgcct cagattggca   120
ggccacagag tcattttatt agaagcagct actgaattgg gtgaagttgg agctggtatt   180
caaattccac caccatcaac caagatttta aaagcaattg gcgtattgga tgcagttgat   240
aaagtctcga ttcatccaca tgatatcttg gtcaagaaat ataaaggtga acttttatct   300
acgcaaaact tggtgcctta tgttctggag aaatacgatg gaatgtattt acatattcac   360
agggctgatt atcataaagt attggttgat agagccgaag aattgggggt tgaaatccat   420
acaaattcaa gagttgttga tattgatttt gaaaaagcaa ctgtcactac tgcaactgga   480
aaacaataca gtggtgatgt cattgtaggg tatgatggag tcagatcaca aaccagagct   540
ttattaactg gtgactcttc tggagcttac gatactggtg atttagcata ccgtgcattg   600
attaaagttg aagatatgaa gaaagttcct ggattggaga aattttacgc caacccaaac   660
atcaacttct ggtggggtcc caccatgcac attgtcatgt atttcttgca cgaaggtgaa   720
atctgtaatg ttgttgcctt gtgccctgac acattaccaa aaggagtttt gaaacaagat   780
gcatcacaag aggaattatt agacttggtt aaaggttggg atcaagacct caccactgtt   840
ttcaaattga ttcatcagt gagtaaatgg cgtttacaag actcacgtga attgaaaacg   900
tgggtcaatt ccaaaactgg caattttata atcttgggtg atgcttccca ttcaaccttg   960
```

```
ccttatttgg ccagtggtgc atcgcaagca gttgaggatg gtgctgttct tgctggatta    1020
ttctccaaga tcgaactgcg tgaccaaatc cctcaacttt acaaatgac ggagaatttg     1080 cgtaaatgga gaagttctca agtggttaga ggatctcatc aatgtcaaga tatttatcat    1140
ttacccgatg gtgaattaca agaaattaga gattcttatt tgtatgataa acaaccggaa    1200
ttgggatgtc ccaatagatt tgctgatcca gttttccaag attttctttg gggatataat    1260
gcttttgatg aagttgaaag agcttggaag gagtttaagg ctggtggtaa tccaacttat    1320
acttatccta acttgtataa accaaagagt agtggtgaga aggatgtgtc aggtggagga    1380
gcagcagcaa cccttgctgc tggtaatacc ccagctgctc cattaagtgc atcaggctaa    1440
gggcatgtgc gggatggata tcttatgtag tttaaattgt atttgaagtt atttacatct    1500
ttttgcaaaa aaaaaaaaa aaaaaa                                          1526

<210> SEQ ID NO 15
<211> LENGTH: 1440
<212> TYPE: DNA
<213> ORGANISM: Candida parapsilosis
<220> FEATURE:
<221> NAME/KEY: misc_feature
<222> LOCATION: (24)..(24)
<223> OTHER INFORMATION: R = A or G

<400> SEQUENCE: 15
atggcggtgc aggcgccgtg gaaracgtac ggtttccaaa aggctccaat acaacttaca    60
tttgtcgttg taggtgccgg tctcggggga gtcgccgcta gtatttgcct cagattggca    120
ggccacagag tcattttatt agaagcagct actgaattgg gtgaagttgg agctggtatt    180
caaattccac caccatcaac caagatttta aaagcaattg gcgtattgga tgcagttgat    240
aaagtctcga ttcatccaca tgatatcttg gtcaagaaat ataaaggtga acttttatct    300
acgcaaaact tggtgcctta tgttctggag aaatacgatg gaatgtattt acatattcac    360
agggctgatt atcataaagt attggttgat agagccgaag aattgggggt tgaaatccat    420
acaaattcaa gagttgttga tattgatttt gaaaaagcaa ctgtcactac tgcaactgga    480
aaacaataca gtggtgatgt cattgtaggg tatgatggag tcagatcaca aaccagagct    540
ttattaactg gtgactcttc tggagcttac gatactggtg atttagcata ccgtgcattg    600
attaaagttg aagatatgaa gaaagttcct ggattggaga aatttttacgc caacccaaac    660 atcaacttct ggtggggtcc caccatgcac attgtcatgt atttcttgca cgaaggtgaa    720
atctgtaatg ttgttgcctt gtgccctgac acattaccaa aaggagtttt gaaacaagat    780
gcatcacaag aggaattatt agacttggtt aaaggttggg atcaagacct caccactgtt    840
ttcaaattga ttacatcagt gagtaaatgg cgtttacaag actcacgtga attgaaaacg    900
tgggtcaatt ccaaaactgg caattttata atcttgggtg atgcttccca ttcaaccttg    960
ccttatttgg ccagtggtgc atcgcaagca gttgaggatg gtgctgttct tgctggatta    1020
ttctccaaga tcgaactgcg tgaccaaatc cctcaacttt acaaatgac ggagaatttg     1080 cgtaaatgga gaagttctca agtggttaga ggatctcatc aatgtcaaga tatttatcat    1140
ttacccgatg gtgaattaca agaaattaga gattcttatt tgtatgataa acaaccggaa    1200
ttgggatgtc ccaatagatt tgctgatcca gttttccaag attttctttg gggatataat    1260
gcttttgatg aagttgaaag agcttggaag gagtttaagg ctggtggtaa tccaacttat    1320
acttatccta acttgtataa accaaagagt agtggtgaga aggatgtgtc aggtggagga    1380
gcagcagcaa cccttgctgc tggtaatacc ccagctgctc cattaagtgc atcaggctaa    1440
```

<210> SEQ ID NO 16
<211> LENGTH: 479
<212> TYPE: PRT
<213> ORGANISM: Candida parapsilosis

<400> SEQUENCE: 16

```
Met Ala Val Gln Ala Pro Trp Lys Thr Tyr Gly Phe Gln Lys Ala Pro
1               5                   10                  15

Ile Gln Leu Thr Phe Val Val Gly Ala Gly Leu Gly Gly Val Ala
            20                  25                  30

Ala Ser Ile Cys Leu Arg Leu Ala Gly His Arg Val Ile Leu Leu Glu
        35                  40                  45

Ala Ala Thr Glu Leu Gly Glu Val Gly Ala Gly Ile Gln Ile Pro Pro
    50                  55                  60

Pro Ser Thr Lys Ile Leu Lys Ala Ile Gly Val Leu Asp Ala Val Asp
65                  70                  75                  80

Lys Val Ser Ile His Pro His Asp Ile Leu Val Lys Tyr Lys Gly
                85                  90                  95

Glu Leu Leu Ser Thr Gln Asn Leu Val Pro Tyr Val Leu Glu Lys Tyr
                100                 105                 110

Asp Gly Met Tyr Leu His Ile His Arg Ala Asp Tyr His Lys Val Leu
            115                 120                 125

Val Asp Arg Ala Glu Glu Leu Gly Val Glu Ile His Thr Asn Ser Arg
    130                 135                 140

Val Val Asp Ile Asp Phe Glu Lys Ala Thr Val Thr Thr Ala Thr Gly
145                 150                 155                 160

Lys Gln Tyr Ser Gly Asp Val Ile Val Gly Tyr Asp Gly Val Arg Ser
                165                 170                 175

Gln Thr Arg Ala Leu Leu Thr Gly Asp Ser Ser Gly Ala Tyr Asp Thr
            180                 185                 190

Gly Asp Leu Ala Tyr Arg Ala Leu Ile Lys Val Glu Asp Met Lys Lys
        195                 200                 205

Val Pro Gly Leu Glu Lys Phe Tyr Ala Asn Pro Asn Ile Asn Phe Trp
    210                 215                 220

Trp Gly Pro Thr Met His Ile Val Met Tyr Phe Leu His Glu Gly Glu
225                 230                 235                 240

Ile Cys Asn Val Val Ala Leu Cys Pro Asp Thr Leu Pro Lys Gly Val
                245                 250                 255

Leu Lys Gln Asp Ala Ser Gln Glu Glu Leu Leu Asp Leu Val Lys Gly
            260                 265                 270

Trp Asp Gln Asp Leu Thr Thr Val Phe Lys Leu Ile Thr Ser Val Ser
        275                 280                 285

Lys Trp Arg Leu Gln Asp Ser Arg Glu Leu Lys Thr Trp Val Asn Ser
    290                 295                 300

Lys Thr Gly Asn Phe Ile Ile Leu Gly Asp Ala Ser His Ser Thr Leu
305                 310                 315                 320

Pro Tyr Leu Ala Ser Gly Ala Ser Gln Ala Val Glu Asp Gly Ala Val
                325                 330                 335

Leu Ala Gly Leu Phe Ser Lys Ile Glu Leu Arg Asp Gln Ile Pro Gln
            340                 345                 350

Leu Leu Gln Met Thr Glu Asn Leu Arg Lys Trp Arg Ser Ser Gln Val
        355                 360                 365

Val Arg Gly Ser His Gln Cys Gln Asp Ile Tyr His Leu Pro Asp Gly
    370                 375                 380
```

-continued

```
Glu Leu Gln Glu Ile Arg Asp Ser Tyr Leu Tyr Asp Lys Gln Pro Glu
385                 390                 395                 400

Leu Gly Cys Pro Asn Arg Phe Ala Asp Pro Val Phe Gln Asp Phe Leu
                405                 410                 415

Trp Gly Tyr Asn Ala Phe Asp Glu Val Glu Arg Ala Trp Lys Glu Phe
            420                 425                 430

Lys Ala Gly Gly Asn Pro Thr Tyr Thr Tyr Pro Asn Leu Tyr Lys Pro
        435                 440                 445

Lys Ser Ser Gly Glu Lys Asp Val Ser Gly Gly Ala Ala Ala Thr
    450                 455                 460

Leu Ala Ala Gly Asn Thr Pro Ala Ala Pro Leu Ser Ala Ser Gly
465                 470                 475
```

<210> SEQ ID NO 17
<211> LENGTH: 35
<212> TYPE: DNA
<213> ORGANISM: artificial sequence
<220> FEATURE:
<223> OTHER INFORMATION: Primer 6

<400> SEQUENCE: 17
ggatttcaac ccccaattct tcggctctat caacc          35

<210> SEQ ID NO 18
<211> LENGTH: 36
<212> TYPE: DNA
<213> ORGANISM: artificial sequence
<220> FEATURE:
<223> OTHER INFORMATION: Primer 7
<220> FEATURE:
<221> NAME/KEY: misc_feature
<222> LOCATION: (24)..(25)
<223> OTHER INFORMATION: n=inosine
<220> FEATURE:
<221> NAME/KEY: misc_feature
<222> LOCATION: (29)..(30)
<223> OTHER INFORMATION: n=inosine
<220> FEATURE:
<221> NAME/KEY: misc_feature
<222> LOCATION: (34)..(35)
<223> OTHER INFORMATION: n=inosine

<400> SEQUENCE: 18
ggccacgcgt cgactagtac gggnngggnn gggnng          36

<210> SEQ ID NO 19
<211> LENGTH: 30
<212> TYPE: DNA
<213> ORGANISM: artificial sequence
<220> FEATURE:
<223> OTHER INFORMATION: Primer 8

<400> SEQUENCE: 19
cttggttgat ggtggtggaa tttgaatacc          30

<210> SEQ ID NO 20
<211> LENGTH: 264
<212> TYPE: DNA
<213> ORGANISM: Candida parapsilosis

<400> SEQUENCE: 20
aaccagaatc ttctgtactt tcacgaatca acaatatac aacaagtaca caccagagaa     60
atggcagttc aagcaccatc aaaaacttat ggtttccaaa aggctccaat acaacttaca    120
tttgtcgttg taggtgccgg tctcggggga gtcgccgcta gtatttgcct cagattggca    180

```
ggccacagag tcattttatt agaagcagct actgaattgg gtgaagttgg agctggtatt    240
caaattccac caccatcaac caag                                           264

<210> SEQ ID NO 21
<211> LENGTH: 1586
<212> TYPE: DNA
<213> ORGANISM: Candida parapsilosis

<400> SEQUENCE: 21
aaccagaatc ttctgtactt tcacgaatca acaatatac aacaagtaca caccagagaa     60
atggcagttc aagcaccatc aaaaacttat ggtttccaaa aggctccaat acaacttaca   120
tttgtcgttg taggtgccgg tctcggggga gtcgccgcta gtatttgcct cagattggca   180
ggccacagag tcattttatt agaagcagct actgaattgg gtgaagttgg agctggtatt   240
caaattccac caccatcaac caagatttta aaagcaattg gcgtattgga tgcagttgat   300
aaagtctcga ttcatccaca tgatatcttg gtcaagaaat ataaaggtga acttttatct   360
acgcaaaact tggtgcctta tgttctggag aaatacgatg gaatgtattt acatattcac   420
agggctgatt atcataaagt attggttgat agagccgaag aattgggggt tgaaatccat   480
acaaattcaa gagttgttga tattgatttt gaaaaagcaa ctgtcactac tgcaactgga   540
aaacaataca gtggtgatgt cattgtaggg tatgatggag tcagatcaca aaccagagct   600
ttattaactg gtgactcttc tggagcttac gatactggtg atttagcata ccgtgcattg   660
attaaagttg aagatatgaa gaaagttcct ggattggaga attttacgc caacccaaac    720 atcaacttct ggtggggtcc caccatgcac attgtcatgt atttcttgca cgaaggtgaa   780
atctgtaatg ttgttgccctt gtgccctgac acattaccaa aaggagtttt gaaacaagat   840
gcatcacaag aggaattatt agacttggtt aaaggttggg atcaagacct caccactgtt   900
ttcaaattga ttcatcagt gagtaaatgg cgtttacaag actcacgtga attgaaaacg    960
tgggtcaatt ccaaaactgg caattttata atcttgggtg atgcttccca ttcaaccttg   1020
ccttatttgg ccagtggtgc atcgcaagca gttgaggatg gtgctgttct tgctggatta   1080
ttctccaaga tcgaactgcg tgaccaaatc cctcaacttt tacaaatgac ggagaatttg   1140
cgtaaatgga gaagttctca gtggttaga ggatctcatc aatgtcaaga tatttatcat    1200
ttacccgatg gtgaattaca agaaattaga gattcttatt tgtatgataa acaaccggaa   1260
ttgggatgtc ccaatagatt tgctgatcca gttttccaag attttctttg gggatataat   1320
gcttttgatg aagttgaaag agcttggaag gagtttaagg ctggtggtaa tccaacttat   1380
acttatccta acttgtataa accaaagagt agtggtgaga aggatgtgtc aggtggagga   1440
gcagcagcaa cccttgctgc tggtaatacc ccagctgctc cattaagtgc atcaggctaa   1500
gggcatgtgc gggatggata tcttatgtag tttaaattgt atttgaagtt atttacatct   1560
ttttgcaaaa aaaaaaaaa aaaaaa                                         1586

<210> SEQ ID NO 22
<211> LENGTH: 1440
<212> TYPE: DNA
<213> ORGANISM: Candida parapsilosis

<400> SEQUENCE: 22
atggcagttc aagcaccatc aaaaacttat ggtttccaaa aggctccaat acaacttaca    60
tttgtcgttg taggtgccgg tctcggggga gtcgccgcta gtatttgcct cagattggca   120
ggccacagag tcattttatt agaagcagct actgaattgg gtgaagttgg agctggtatt   180
```

```
caaattccac caccatcaac caagatttta aaagcaattg gcgtattgga tgcagttgat    240
aaagtctcga ttcatccaca tgatatcttg gtcaagaaat ataaaggtga actttatct    300 acgcaaaact tggtgcctta tgttctggag aaatacgatg gaatgtattt acatattcac    360
agggctgatt atcataaagt attggttgat agagccgaag aattgggggt tgaaatccat    420
acaaattcaa gagttgttga tattgatttt gaaaaagcaa ctgtcactac tgcaactgga    480
aaacaataca gtggtgatgt cattgtaggg tatgatggag tcagatcaca aaccagagct    540
ttattaactg gtgactcttc tggagcttac gatactggtg atttagcata ccgtgcattg    600
attaaagttg aagatatgaa gaaagttcct ggattggaga aattttacgc aacccaaac    660 atcaacttct ggtggggtcc caccatgcac attgtcatgt atttcttgca cgaaggtgaa    720
atctgtaatg ttgttgcctt gtgccctgac acattaccaa aaggagtttt gaaacaagat    780
gcatcacaag aggaattatt agacttggtt aaaggttggg atcaagacct caccactgtt    840
ttcaaattga ttcatcagt gagtaaatgg cgtttacaag actcacgtga attgaaaacg    900
tgggtcaatt ccaaaactgg caattttata atcttgggtg atgcttccca ttcaaccttg    960
ccttatttgg ccagtggtgc atcgcaagca gttgaggatg tgctgttct tgctggatta    1020 ttctccaaga tcgaactgcg tgaccaaatc cctcaacttt tacaaatgac ggagaatttg    1080
cgtaaatgga gaagttctca gtggttaga ggatctcatc aatgtcaaga tatttatcat    1140 tacccgatg gtgaattaca agaaattaga gattcttatt tgtatgataa acaaccggaa    1200
ttgggatgtc ccaatagatt tgctgatcca gtttccaag attttctttg gggatataat    1260
gcttttgatg aagttgaaag agcttggaag gagtttaagg ctggtggtaa tccaacttat    1320
acttatccta acttgtataa accaaagagt agtggtgaga aggatgtgtc aggtggagga    1380
gcagcagcaa cccttgctgc tggtaatacc ccagctgctc cattaagtgc atcaggctaa    1440
```

<210> SEQ ID NO 23
<211> LENGTH: 479
<212> TYPE: PRT
<213> ORGANISM: Candida parapsilosis

<400> SEQUENCE: 23

```
Met Ala Val Gln Ala Pro Ser Lys Thr Tyr Gly Phe Gln Lys Ala Pro
1               5                   10                  15

Ile Gln Leu Thr Phe Val Val Gly Ala Gly Leu Gly Gly Val Ala
            20                  25                  30

Ala Ser Ile Cys Leu Arg Leu Ala Gly His Arg Val Ile Leu Glu
            35                  40                  45

Ala Ala Thr Glu Leu Gly Glu Val Gly Ala Gly Ile Gln Ile Pro Pro
        50                  55                  60

Pro Ser Thr Lys Ile Leu Lys Ala Ile Gly Val Leu Asp Ala Val Asp
65                  70                  75                  80

Lys Val Ser Ile His Pro Asp Ile Leu Val Lys Tyr Lys Gly
                    85                  90                  95

Glu Leu Leu Ser Thr Gln Asn Leu Val Pro Tyr Val Leu Glu Lys Tyr
                100                 105                 110

Asp Gly Met Tyr Leu His Ile His Arg Ala Asp Tyr His Lys Val Leu
            115                 120                 125

Val Asp Arg Ala Glu Glu Leu Gly Val Glu Ile His Thr Asn Ser Arg
        130                 135                 140

Val Val Asp Ile Asp Phe Glu Lys Ala Thr Val Thr Thr Ala Thr Gly
145                 150                 155                 160
```

-continued

Lys Gln Tyr Ser Gly Asp Val Ile Val Gly Tyr Asp Gly Val Arg Ser
                165                 170                 175

Gln Thr Arg Ala Leu Leu Thr Gly Asp Ser Ser Gly Ala Tyr Asp Thr
            180                 185                 190

Gly Asp Leu Ala Tyr Arg Ala Leu Ile Lys Val Glu Asp Met Lys Lys
        195                 200                 205

Val Pro Gly Leu Glu Lys Phe Tyr Ala Asn Pro Asn Ile Asn Phe Trp
    210                 215                 220

Trp Gly Pro Thr Met His Ile Val Met Tyr Phe Leu His Glu Gly Glu
225                 230                 235                 240

Ile Cys Asn Val Val Ala Leu Cys Pro Asp Thr Leu Pro Lys Gly Val
                245                 250                 255

Leu Lys Gln Asp Ala Ser Gln Glu Glu Leu Leu Asp Leu Val Lys Gly
            260                 265                 270

Trp Asp Gln Asp Leu Thr Thr Val Phe Lys Leu Ile Thr Ser Val Ser
        275                 280                 285

Lys Trp Arg Leu Gln Asp Ser Arg Glu Leu Lys Thr Trp Val Asn Ser
    290                 295                 300

Lys Thr Gly Asn Phe Ile Ile Leu Gly Asp Ala Ser His Ser Thr Leu
305                 310                 315                 320

Pro Tyr Leu Ala Ser Gly Ala Ser Gln Ala Val Glu Asp Gly Ala Val
                325                 330                 335

Leu Ala Gly Leu Phe Ser Lys Ile Glu Leu Arg Asp Gln Ile Pro Gln
            340                 345                 350

Leu Leu Gln Met Thr Glu Asn Leu Arg Lys Trp Arg Ser Ser Gln Val
        355                 360                 365

Val Arg Gly Ser His Gln Cys Gln Asp Ile Tyr His Leu Pro Asp Gly
    370                 375                 380

Glu Leu Gln Glu Ile Arg Asp Ser Tyr Leu Tyr Asp Lys Gln Pro Glu
385                 390                 395                 400

Leu Gly Cys Pro Asn Arg Phe Ala Asp Pro Val Phe Gln Asp Phe Leu
                405                 410                 415

Trp Gly Tyr Asn Ala Phe Asp Glu Val Glu Arg Ala Trp Lys Glu Phe
            420                 425                 430

Lys Ala Gly Gly Asn Pro Thr Tyr Thr Tyr Pro Asn Leu Tyr Lys Pro
        435                 440                 445

Lys Ser Ser Gly Glu Lys Asp Val Ser Gly Gly Ala Ala Ala Thr
    450                 455                 460

Leu Ala Ala Gly Asn Thr Pro Ala Ala Pro Leu Ser Ala Ser Gly
465                 470                 475

<210> SEQ ID NO 24
<211> LENGTH: 34
<212> TYPE: DNA
<213> ORGANISM: artificial sequence
<220> FEATURE:
<223> OTHER INFORMATION: Primer 9

<400> SEQUENCE: 24
cccgcacata agcttagcct gatgcactta atgg         34

<210> SEQ ID NO 25
<211> LENGTH: 39
<212> TYPE: DNA
<213> ORGANISM: artificial sequence

```
<220> FEATURE:
<223> OTHER INFORMATION: Primer 10

<400> SEQUENCE: 25
gaattcgccc atatggcggt gcaggcgccg tcgaagacg                                39

<210> SEQ ID NO 26
<211> LENGTH: 1440
<212> TYPE: DNA
<213> ORGANISM: Candida parapsilosis

<400> SEQUENCE: 26
atggcggtgc aggcgccgtc gaagacgtac ggtttccaaa aggctccaat acaacttaca        60
tttgtcgttg taggtgccgg tctcggggga gtcgccgcta gtatttgcct cagattggca       120
ggccacagag tcattttatt agaagcagct actgaattgg gtgaagttgg agctggtatt       180
caaattccac caccatcaac caagatttta aaagcaattg gcgtattgga tgcagttgat       240
aaagtctcga ttcatccaca tgatatcttg gtcaagaaat ataaaggtga acttttatct       300
acgcaaaact tggtgcctta tgttctggag aaatacgatg gaatgtattt acatattcac       360
agggctgatt atcataaagt attggttgat agagccgaag aattggggt tgaaatccat       420 acaaattcaa gagttgttga tattgatttt gaaaaagcaa ctgtcactac tgcaactgga       480
aaacaataca gtggtgatgt cattgtaggg tatgatggag tcagatcaca aaccagagct       540
ttattaactg gtgactcttc tggagcttac gatactggtg atttagcata ccgtgcattg       600
attaaagttg aagatatgaa gaaagttcct ggattggaga aattttacgc aacccaaac       660 atcaacttct ggtggggtcc caccatgcac attgtcatgt atttcttgca cgaaggtgaa       720
atctgtaatg ttgttgcctt gtgccctgac acattaccaa aggagttttt gaaacaagat       780
gcatcacaag aggaattatt agacttggtt aaaggttggg atcaagacct caccactgtt       840
ttcaaattga ttcatcagt gagtaaatgg cgtttacaag actcacgtga attgaaaacg       900
tgggtcaatt ccaaaactgg caatttata atcttggtg atgcttccca ttcaaccttg       960
ccttatttgg ccagtggtgc atcgcaagca gttgaggatg gtgctgttct tgctggatta      1020
ttctccaaga tcgaactgcg tgaccaaatc cctcaacttt tacaaatgac ggagaatttg      1080
cgtaaatgga gaagttctca gtggttaga ggatctcatc aatgtcaaga tatttatcat       1140
ttacccgatg gtgaattaca agaaattaga gattcttatt tgtatgataa acaaccggaa      1200
ttgggatgtc ccaatagatt tgctgatcca gttttccaag attttctttg gggatataat      1260
gcttttgatg aagttgaaag agcttggaag gagtttaagg ctggtggtaa tccaacttat      1320
acttatccta acttgtataa accaaagagt agtggtgaga aggatgtgtc aggtggagga      1380
gcagcagcaa cccttgctgc tggtaatacc ccagctgctc cattaagtgc atcaggctaa      1440

<210> SEQ ID NO 27
<211> LENGTH: 32
<212> TYPE: DNA
<213> ORGANISM: artificial sequence
<220> FEATURE:
<223> OTHER INFORMATION: Primer 11

<400> SEQUENCE: 27
ctactcaatt catatgtcac accccgcgtt aa                                      32
```

```
<210> SEQ ID NO 28
<211> LENGTH: 34
<212> TYPE: DNA
<213> ORGANISM: artificial sequence
<220> FEATURE:
<223> OTHER INFORMATION: Primer 12

<400> SEQUENCE: 28
catcttacta gatctttagt acaacggtga cgcc                                34

<210> SEQ ID NO 29
<211> LENGTH: 498
<212> TYPE: DNA
<213> ORGANISM: Escherichia coli

<400> SEQUENCE: 29
atgtcacacc ccgcgttaac gcaactgcgt gcgctgcgct attgtaaaga gatccctgcc    60
ctggatccgc aactgctcga ctggctgttg ctggaggatt ccatgacaaa acgttttgaa   120
cagcagggaa aaacggtaag cgtgacgatg atccgcgaag ggtttgtcga gcagaatgaa   180
atccccgaag aactgccgct gctgccgaaa gagtctcgtt actggttacg tgaaattttg   240
ttatgtgccg atggtgaacc gtggcttgcc ggtcgtaccg tcgttcctgt gtcaacgtta   300
agcgggccgg agctggcgtt acaaaaattg ggtaaaacgc cgttaggacg ctatctgttc   360
acatcatcga cattaacccg ggactttatt gagataggcc gtgatgccgg gctgtggggg   420
cgacgttccc gcctgcgatt aagcggtaaa ccgctgttgc taacagaact gttttttaccg   480 gcgtcaccgt tgtactaa                                                 498

<210> SEQ ID NO 30
<211> LENGTH: 165
<212> TYPE: PRT
<213> ORGANISM: Escherichia coli

<400> SEQUENCE: 30

Met Ser His Pro Ala Leu Thr Gln Leu Arg Ala Leu Arg Tyr Cys Lys
1               5                   10                  15

Glu Ile Pro Ala Leu Asp Pro Gln Leu Leu Asp Trp Leu Leu Leu Glu
            20                  25                  30

Asp Ser Met Thr Lys Arg Phe Glu Gln Gln Gly Lys Thr Val Ser Val
        35                  40                  45

Thr Met Ile Arg Glu Gly Phe Val Glu Gln Asn Glu Ile Pro Glu Glu
    50                  55                  60

Leu Pro Leu Leu Pro Lys Glu Ser Arg Tyr Trp Leu Arg Glu Ile Leu
65                  70                  75                  80

Leu Cys Ala Asp Gly Glu Pro Trp Leu Ala Gly Arg Thr Val Val Pro
                85                  90                  95

Val Ser Thr Leu Ser Gly Pro Glu Leu Ala Leu Gln Lys Leu Gly Lys
            100                 105                 110

Thr Pro Leu Gly Arg Tyr Leu Phe Thr Ser Ser Thr Leu Thr Arg Asp
        115                 120                 125

Phe Ile Glu Ile Gly Arg Asp Ala Gly Leu Trp Gly Arg Arg Ser Arg
    130                 135                 140

Leu Arg Leu Ser Gly Lys Pro Leu Leu Leu Thr Glu Leu Phe Leu Pro
145                 150                 155                 160

Ala Ser Pro Leu Tyr
                165
```

<210> SEQ ID NO 31
<211> LENGTH: 39
<212> TYPE: DNA
<213> ORGANISM: artificial sequence
<220> FEATURE:
<223> OTHER INFORMATION: Primer 13

<400> SEQUENCE: 31
ctactcactt agatctccat ggcttcctct gtcatttct                              39

<210> SEQ ID NO 32
<211> LENGTH: 32
<212> TYPE: DNA
<213> ORGANISM: artificial sequence
<220> FEATURE:
<223> OTHER INFORMATION: Primer 14

<400> SEQUENCE: 32
catcttactc atatgccaca cctgcatgca gc                                    32

<210> SEQ ID NO 33
<211> LENGTH: 684
<212> TYPE: DNA
<213> ORGANISM: Escherichia coli

<400> SEQUENCE: 33
atggcttcct ctgtcatttc ttcagcagct gttgccacac gcagcaatgt tacacaagct       60
agcatggttg cacctttcac tggtctcaaa tcttcagcca cttccctgt tacaaagaag       120 caaaaccttg acatcacttc cattgctagc aatggtggaa gagttagctg catgcaggtg      180
tggcatatgt cacaccccgc gttaacgcaa ctgcgtgcgc tgcgctattg taaagagatc      240
cctgccctgg atccgcaact gctcgactgg ctgttgctgg aggattccat gacaaaacgt      300
tttgaacagc agggaaaaac ggtaagcgtg acgatgatcc gcgaagggtt tgtcgagcag      360
aatgaaatcc ccgaagaact gccgctgctg ccgaaagagt ctcgttactg gttacgtgaa      420
attttgttat gtgccgatgg tgaaccgtgg cttgccggtc gtaccgtcgt tcctgtgtca      480
acgttaagcg gccggagct ggcgttacaa aaattgggta aaacgccgtt aggacgctat       540
ctgttcacat catcgacatt aacccgggac tttattgaga taggccgtga tgccgggctg      600
tgggggcgac gttcccgcct gcgattaagc ggtaaaccgc tgttgctaac agaactgttt      660
ttaccggcgt caccgttgta ctaa                                             684

<210> SEQ ID NO 34
<211> LENGTH: 227
<212> TYPE: PRT
<213> ORGANISM: Escherichia coli

<400> SEQUENCE: 34

Met Ala Ser Ser Val Ile Ser Ser Ala Ala Val Ala Thr Arg Ser Asn
1               5                   10                  15

Val Thr Gln Ala Ser Met Val Ala Pro Phe Thr Gly Leu Lys Ser Ser
            20                  25                  30

Ala Thr Phe Pro Val Thr Lys Lys Gln Asn Leu Asp Ile Thr Ser Ile
        35                  40                  45

Ala Ser Asn Gly Gly Arg Val Ser Cys Met Gln Val Trp His Met Ser
    50                  55                  60

His Pro Ala Leu Thr Gln Leu Arg Ala Leu Arg Tyr Cys Lys Glu Ile
65                  70                  75                  80

```
Pro Ala Leu Asp Pro Gln Leu Leu Asp Trp Leu Leu Glu Asp Ser
            85                  90                  95
Met Thr Lys Arg Phe Glu Gln Gly Lys Thr Val Ser Val Thr Met
            100                 105                 110
Ile Arg Glu Gly Phe Val Glu Gln Asn Glu Ile Pro Glu Leu Pro
            115                 120                 125
Leu Leu Pro Lys Glu Ser Arg Tyr Trp Leu Arg Glu Ile Leu Cys
    130                 135                 140
Ala Asp Gly Glu Pro Trp Leu Ala Gly Arg Thr Val Pro Val Ser
145                 150                 155                 160
Thr Leu Ser Gly Pro Glu Leu Ala Leu Gln Lys Leu Gly Lys Thr Pro
                165                 170                 175
Leu Gly Arg Tyr Leu Phe Thr Ser Ser Thr Leu Thr Arg Asp Phe Ile
            180                 185                 190
Glu Ile Gly Arg Asp Ala Gly Leu Trp Gly Arg Arg Ser Arg Leu Arg
    195                 200                 205
Leu Ser Gly Lys Pro Leu Leu Leu Thr Glu Leu Phe Leu Pro Ala Ser
    210                 215                 220

Pro Leu Tyr
225

<210> SEQ ID NO 35
<211> LENGTH: 33
<212> TYPE: DNA
<213> ORGANISM: artificial sequence
<220> FEATURE:
<223> OTHER INFORMATION: Primer 15

<400> SEQUENCE: 35
cccgggggta cctaaagaag gagtgcgtcg aag                                    33

<210> SEQ ID NO 36
<211> LENGTH: 46
<212> TYPE: DNA
<213> ORGANISM: artificial sequence
<220> FEATURE:
<223> OTHER INFORMATION: Primer 16

<400> SEQUENCE: 36
gatatcaagc tttctagagt cgacatcgat ctagtaacat agatga                     46

<210> SEQ ID NO 37
<211> LENGTH: 831
<212> TYPE: DNA
<213> ORGANISM: Pseudomonas putida

<400> SEQUENCE: 37
atgagcacat acgaaggtcg ctgggctacc gtgaaggtcg aactggagtc gggcattgcc      60
tgggtcaccc tcaaccggcc ggaaaagcgc aatgcaatga gccccacgct gaaccgggaa     120
atggtcgacg tgctggaaac cctggaacag gacggcgaag ccggggtgct cgtgctgacc     180
ggcgcgggtg aatcgtggac ggcaggcatg gacctgaagg aatacttccg tgaggtggac     240
gccggcccgg aaatcctcca ggaaaaaatc cgccgcgatg cctcgcaatg caatggaggg     300
ctgctgcgca tgtacgccaa gccgactatc gccatggtca acggctggtg ctttggcggc     360
ggcttcagcc cgctggtggc ctgcgacctg gccatctgtg ccgacgaggc cacctttggc     420
ctgtcggaaa tcaactgggg catcccaccg ggcaacctgg tcagcaaagc catggccgat     480
accgttggcc accgccagtc gctgtactac atcatgaccg gcaagacttt cggcgggcct     540
```

```
aaagctgccg agatggggct ggttaacgag agcgtgccgc tgcgcaatt gcgcgacgtc      600 acccgcgaac tggcgctcaa cctgctggaa agaacccgg tggtgctgcg tgcggccaag      660
aacggtttca gcgctgccg cgaactgacc tgggagcaga acgaagacta cctgtacgcc      720
aagctcgacc agtcccgtct gctggacacc gaaggtgggc gcgagcaggg catgaagcag      780
ttcctcgacg acaagagcat caagccaggc ctgcaagcca tcaagcgctg a              831
```

<210> SEQ ID NO 38
<211> LENGTH: 276
<212> TYPE: PRT
<213> ORGANISM: Pseudomonas putida

<400> SEQUENCE: 38

```
Met Ser Thr Tyr Glu Gly Arg Trp Ala Thr Val Lys Val Glu Leu Glu
1               5                   10                  15

Ser Gly Ile Ala Trp Val Thr Leu Asn Arg Pro Glu Lys Arg Asn Ala
            20                  25                  30

Met Ser Pro Thr Leu Asn Arg Glu Met Val Asp Val Leu Glu Thr Leu
        35                  40                  45

Glu Gln Asp Gly Glu Ala Gly Val Leu Val Leu Thr Gly Ala Gly Glu
    50                  55                  60

Ser Trp Thr Ala Gly Met Asp Leu Lys Glu Tyr Phe Arg Glu Val Asp
65                  70                  75                  80

Ala Gly Pro Glu Ile Leu Gln Glu Lys Ile Arg Arg Asp Ala Ser Gln
                85                  90                  95

Trp Gln Trp Arg Leu Leu Arg Met Tyr Ala Lys Pro Thr Ile Ala Met
            100                 105                 110

Val Asn Gly Trp Cys Phe Gly Gly Phe Ser Pro Leu Val Ala Cys
        115                 120                 125

Asp Leu Ala Ile Cys Ala Asp Glu Ala Thr Phe Gly Leu Ser Glu Ile
    130                 135                 140

Asn Trp Gly Ile Pro Pro Gly Asn Leu Val Ser Lys Ala Met Ala Asp
145                 150                 155                 160

Thr Val Gly His Arg Gln Ser Leu Tyr Tyr Ile Met Thr Gly Lys Thr
                165                 170                 175

Phe Gly Gly Pro Lys Ala Ala Glu Met Gly Leu Val Asn Glu Ser Val
            180                 185                 190

Pro Leu Ala Gln Leu Arg Asp Val Thr Arg Glu Leu Ala Leu Asn Leu
        195                 200                 205

Leu Glu Lys Asn Pro Val Val Leu Arg Ala Ala Lys Asn Gly Phe Lys
    210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Thr Glu Gly Gly Arg Glu Gln
                245                 250                 255

Gly Met Lys Gln Phe Leu Asp Asp Lys Ser Ile Lys Pro Gly Leu Gln
            260                 265                 270

Ala Ile Lys Arg
        275
```

<210> SEQ ID NO 39
<211> LENGTH: 26
<212> TYPE: DNA
<213> ORGANISM: artificial sequence
<220> FEATURE:
<223> OTHER INFORMATION: Primer 17

<400> SEQUENCE: 39
gaatatttgc atccatggag gaatcc                                   26

<210> SEQ ID NO 40
<211> LENGTH: 24
<212> TYPE: DNA
<213> ORGANISM: artificial sequence
<220> FEATURE:
<223> OTHER INFORMATION: Primer 18

<400> SEQUENCE: 40
gaacatcgtc gacttagtgg ttgc                                     24

<210> SEQ ID NO 41
<211> LENGTH: 1443
<212> TYPE: DNA
<213> ORGANISM: Arabidopsis thaliana

<400> SEQUENCE: 41
atggaggaat ccaaaacacc tcacgttgcg atcataccaa gtccgggaat gggtcatctc    60
ataccactcg tcgagtttgc taaacgactc gtccatcttc acggcctcac cgttaccttc   120
gtcatcgccg gcgaaggtcc accatcaaaa gctcagagaa ccgtcctcga ctcgctccct   180
tcttcaatct cctccgtctt tctccctcct gttgatctca ccgatctctc ttcgtccact   240
cgcatcgaat ctcggatctc cctcaccgtg actcgttcaa acccggagct ccggaaagtc   300
ttcgactcgt tcgtggaggg aggtcgtttg ccaacggcgc tcgtcgtcga tctcttcggt   360
acggacgctt tcgacgtggc cgtagaattt cacgtgccac cgtatatttt ctacccaaca   420
acggccaacg tcttgtcgtt ttttctccat ttgcctaaac tagacgaaac ggtgtcgtgt   480
gagttcaggg aattaaccga accgcttatg ctccctggat gtgtaccggt tgccgggaaa   540
gatttccttg acccggccca agaccggaaa gacgatgcat acaaatggct tctccataac   600
accaagaggt acaaagaagc cgaaggtatt cttgtgaata ccttctttga gctagagcca   660
aatgctataa aggccttgca agaaccgggt cttgataaac caccggttta tccggttgga   720
ccgttggtta acattggtaa gcaagaggct aagcaatccg aagagtctga atgtttaaag   780
tggttggata ccagccgct cggttcggtt ttatatgtgt cctttggtag tggcggtacc   840
ctcacatgta agcagctcaa tgagcttgct cttggtcttg cagatagtga gcaacggttt   900
ctttgggtca tacgaagtcc tagtggggtc gctaattcgt cgtattttga ttcacatagc   960
caaacagatc cattgacatt tttaccaccg ggattttag agcggactaa aaaagaggt    1020 tttgtgatcc cttttggc tccacaagcc caagtcttgg cgcatccatc cacgggagga   1080
tttttaactc attgtggatg gaattcgact ctagagagtg tagtaagtgg tattccactt   1140
atagcatggc cattatacgc agaacagaag atgaatgcgg ttttgttgag tgaagatatt   1200
cgtgcggcac ttaggccgcg tgccggggac gatgggttag ttagaagaga gaggtggct   1260 agagtggtaa aaggattgat ggaaggtgaa gaaggcaaag gagtgaggaa caagatgaag   1320
gaattgaagg aagcagcttg tagggtattg aaggatgatg gacttcgac aaaagcactt    1380 agtcttgtgg cctttaaagtg gaaagcccac aaaaaagagt tagagcaaaa tggcaaccac   1440
taa                                                                 1443

<210> SEQ ID NO 42
<211> LENGTH: 480
<212> TYPE: PRT
<213> ORGANISM: Arabidopsis thaliana

```
<400> SEQUENCE: 42

Met Glu Glu Ser Lys Thr Pro His Val Ala Ile Ile Pro Ser Pro Gly
1               5                   10                  15

Met Gly His Leu Ile Pro Leu Val Glu Phe Ala Lys Arg Leu Val His
            20                  25                  30

Leu His Gly Leu Thr Val Thr Phe Val Ile Ala Gly Glu Gly Pro Pro
            35                  40                  45

Ser Lys Ala Gln Arg Thr Val Leu Asp Ser Leu Pro Ser Ser Ile Ser
    50                  55                  60

Ser Val Phe Leu Pro Pro Val Asp Leu Thr Asp Leu Ser Ser Ser Thr
65                  70                  75                  80

Arg Ile Glu Ser Arg Ile Ser Leu Thr Val Thr Arg Ser Asn Pro Glu
                85                  90                  95

Leu Arg Lys Val Phe Asp Ser Phe Val Glu Gly Arg Leu Pro Thr
                100                 105                 110

Ala Leu Val Val Asp Leu Phe Gly Thr Asp Ala Phe Asp Val Ala Val
            115                 120                 125

Glu Phe His Val Pro Pro Tyr Ile Phe Tyr Pro Thr Thr Ala Asn Val
130                 135                 140

Leu Ser Phe Phe Leu His Leu Pro Lys Leu Asp Glu Thr Val Ser Cys
145                 150                 155                 160

Glu Phe Arg Glu Leu Thr Glu Pro Leu Met Leu Pro Gly Cys Val Pro
                165                 170                 175

Val Ala Gly Lys Asp Phe Leu Asp Pro Ala Gln Asp Arg Lys Asp Asp
            180                 185                 190

Ala Tyr Lys Trp Leu Leu His Asn Thr Lys Arg Tyr Lys Glu Ala Glu
        195                 200                 205

Gly Ile Leu Val Asn Thr Phe Phe Glu Leu Glu Pro Asn Ala Ile Lys
    210                 215                 220

Ala Leu Gln Glu Pro Gly Leu Asp Lys Pro Val Tyr Pro Val Gly
225                 230                 235                 240

Pro Leu Val Asn Ile Gly Lys Gln Glu Ala Lys Gln Ser Glu Glu Ser
                245                 250                 255

Glu Cys Leu Lys Trp Leu Asp Asn Gln Pro Leu Gly Ser Val Leu Tyr
            260                 265                 270

Val Ser Phe Gly Ser Gly Gly Thr Leu Thr Cys Lys Gln Leu Asn Glu
        275                 280                 285

Leu Ala Leu Gly Leu Ala Asp Ser Glu Gln Arg Phe Leu Trp Val Ile
    290                 295                 300

Arg Ser Pro Ser Gly Val Ala Asn Ser Ser Tyr Phe Asp Ser His Ser
305                 310                 315                 320

Gln Thr Asp Pro Leu Thr Phe Leu Pro Pro Gly Phe Leu Glu Arg Thr
                325                 330                 335

Lys Lys Arg Gly Phe Val Ile Pro Phe Trp Ala Pro Gln Ala Gln Val
            340                 345                 350

Leu Ala His Pro Ser Thr Gly Gly Phe Leu Thr His Cys Gly Trp Asn
        355                 360                 365

Ser Thr Leu Glu Ser Val Ser Gly Ile Pro Leu Ile Ala Trp Pro
370                 375                 380

Leu Tyr Ala Glu Gln Lys Met Asn Ala Val Leu Leu Ser Glu Asp Ile
385                 390                 395                 400

Arg Ala Ala Leu Arg Pro Arg Ala Gly Asp Asp Gly Leu Val Arg Arg
                405                 410                 415
```

```
Glu Glu Val Ala Arg Val Val Lys Gly Leu Met Glu Gly Glu Glu Gly
                    420                 425                 430

Lys Gly Val Arg Asn Lys Met Lys Glu Leu Lys Glu Ala Ala Cys Arg
            435                 440                 445

Val Leu Lys Asp Asp Gly Thr Ser Thr Lys Ala Leu Ser Leu Val Ala
    450                 455                 460

Leu Lys Trp Lys Ala His Lys Lys Glu Leu Glu Gln Asn Gly Asn His
465                 470                 475                 480

<210> SEQ ID NO 43
<211> LENGTH: 34
<212> TYPE: DNA
<213> ORGANISM: artificial sequence
<220> FEATURE:
<223> OTHER INFORMATION: Primer 19

<400> SEQUENCE: 43
gtcgacaagg agatatacat atggcggtgc aggc                               34

<210> SEQ ID NO 44
<211> LENGTH: 31
<212> TYPE: DNA
<213> ORGANISM: artificial sequence
<220> FEATURE:
<223> OTHER INFORMATION: Primer 20

<400> SEQUENCE: 44
gtcgacaagc ttagcctgat gcacttaatg g                                  31

<210> SEQ ID NO 45
<211> LENGTH: 31
<212> TYPE: DNA
<213> ORGANISM: artificial sequence
<220> FEATURE:
<223> OTHER INFORMATION: Primer 21

<400> SEQUENCE: 45
gtcgacaagg agatatacca tggaggaatc c                                  31

<210> SEQ ID NO 46
<211> LENGTH: 33
<212> TYPE: DNA
<213> ORGANISM: artificial sequence
<220> FEATURE:
<223> OTHER INFORMATION: Primer 22

<400> SEQUENCE: 46
ctcgagttag tggttgccat tttgctctaa ctc                                33

<210> SEQ ID NO 47
<211> LENGTH: 3452
<212> TYPE: DNA
<213> ORGANISM: artificial sequence
<220> FEATURE:
<223> OTHER INFORMATION: Nucleotide sequence of nucleic acid fragment
      encoding CPL (from Escherichia coli), pHBA 1-hydroxylase (from
      Candida parapsilosis), and UGT72B1 (from Arabidopsis thaliana).

<400> SEQUENCE: 47
catatgtcac acccgcgtt aacgcaactg cgtgcgctgc gctattgtaa agagatccct     60
gccctggatc cgcaactgct cgactggctg ttgctggagg attccatgac aaaacgtttt   120
gaacagcagg gaaaaacggt aagcgtgacg atgatccgcg aagggtttgt cgagcagaat   180
gaaatccccg aagaactgcc gctgctgccg aaagagtctc gttactggtt acgtgaaatt   240
```

| | |
|---|---|
| ttgttatgtg ccgatggtga accgtggctt gccggtcgta ccgtcgttcc tgtgtcaacg | 300 |
| ttaagcgggc cggagctggc gttacaaaaa ttgggtaaaa cgccgttagg acgctatctg | 360 |
| ttcacatcat cgacattaac ccgggacttt attgagatag gccgtgatgc cgggctgtgg | 420 |
| gggcgacgtt cccgcctgcg attaagcggt aaaccgctgt tgctaacaga actgttttta | 480 |
| ccggcgtcac cgttgtacta agatccgaa ttcgagctcc gtcgacaagg agatatacat | 540 |
| atggcggtgc aggcgccgtc gaagacgtac ggtttccaaa aggctccaat acaacttaca | 600 |
| tttgtcgttg taggtgccgg tctcggggga gtcgccgcta gtatttgcct cagattggca | 660 |
| ggccacagag tcattttatt agaagcagct actgaattgg gtgaagttgg agctggtatt | 720 |
| caaattccac caccatcaac caagatttta aaagcaattg gcgtattgga tgcagttgat | 780 |
| aaagtctcga ttcatccaca tgatatcttg gtcaagaaat ataaaggtga acttttatct | 840 |
| acgcaaaact tggtgcctta tgttctggag aaatacgatg gaatgtattt acatattcac | 900 |
| agggctgatt atcataaagt attggttgat agagccgaag aattgggggt tgaaatccat | 960 |
| acaaattcaa gagttgttga tattgatttt gaaaaagcaa ctgtcactac tgcaactgga | 1020 |
| aaacaataca gtggtgatgt cattgtaggg tatgatggag tcagatcaca aaccagagct | 1080 |
| ttattaactg gtgactcttc tggagcttac gatactggtg atttagcata ccgtgcattg | 1140 |
| attaaagttg aagatatgaa gaaagttcct ggattggaga aattttacgc caacccaaac | 1200 |
| atcaacttct ggtggggtcc caccatgcac attgtcatgt atttcttgca cgaaggtgaa | 1260 |
| atctgtaatg ttgttgcctt gtgccctgac acattaccaa aaggagtttt gaaacaagat | 1320 |
| gcatcacaag aggaattatt agacttggtt aaaggttggg atcaagacct caccactgtt | 1380 |
| ttcaaattga ttcatcagt gagtaaatgg cgtttacaag actcacgtga attgaaaacg | 1440 |
| tgggtcaatt ccaaaactgg caatttatata atcttgggtg atgcttccca ttcaaccttg | 1500 |
| ccttatttgg ccagtggtgc atcgcaagca gttgaggatg gtgctgttct tgctggatta | 1560 |
| ttctccaaga tcgaactgcg tgaccaaatc cctcaacttt tacaaatgac ggagaatttg | 1620 |
| cgtaaatgga gaagttctca agtggttaga ggatctcatc aatgtcaaga tatttatcat | 1680 |
| ttacccgatg gtgaattaca agaaattaga gattcttatt tgtatgataa acaaccggaa | 1740 |
| ttgggatgtc ccaatagatt tgctgatcca gttttccaag attttctttg gggatataat | 1800 |
| gcttttgatg aagttgaaag agcttggaag gagtttaagg ctggtggtaa tccaacttat | 1860 |
| acttatccta acttgtataa accaaagagt agtggtgaga aggatgtgtc aggtggagga | 1920 |
| gcagcagcaa cccttgctgc tggtaatacc ccagctgctc cattaagtgc atcaggctaa | 1980 |
| gcttgtcgac aaggagatat accatggagg aatccaaaac acctcacgtt gcgatcatac | 2040 |
| caagtccggg aatgggtcat ctcataccac tcgtcgagtt tgctaaacga ctcgtccatc | 2100 |
| ttcacggcct caccgttacc ttcgtcatcg ccggcgaagg tccaccatca aaagctcaga | 2160 |
| gaaccgtcct cgactcgctc ccttcttcaa tctcctccgt ctttctccct cctgttgatc | 2220 |
| tcaccgatct ctcttcgtcc actcgcatcg aatctcggat ctccctcacc gtgactcgtt | 2280 |
| caaacccgga gctccggaaa gtcttcgact cgttcgtgga gggaggtcgt ttgccaacgg | 2340 |
| cgctcgtcgt cgatctcttc ggtacggacg cttcgacgt ggccgtagaa tttcacgtgc | 2400 |
| caccgtatat tttctaccca caacggcca acgtcttgtc gttttttctc catttgccta | 2460 |
| aactagacga aacggtgtcg tgtgagttca gggaattaac cgaaccgctt atgctccctg | 2520 |
| gatgtgtacc ggttgccggg aaagatttcc ttgacccggc ccaagaccgg aaagacgatg | 2580 |
| catacaaatg gcttctccat aacaccaaga ggtacaaaga agccgaaggt attcttgtga | 2640 |

```
atacctctt tgagctagag ccaaatgcta taaaggcctt gcaagaaccg ggtcttgata    2700
aaccaccggt ttatccggtt ggaccgttgg ttaacattgg taagcaagag gctaagcaat    2760
ccgaagagtc tgaatgttta aagtggttgg ataaccagcc gctcggttcg gttttatatg    2820
tgtcctttgg tagtggcggt accctcacat gtaagcagct caatgagctt gctcttggtc    2880
ttgcagatag tgagcaacgg tttctttggg tcatacgaag tcctagtggg gtcgctaatt    2940
cgtcgtattt tgattcacat agccaaacag atccattgac atttttacca ccgggatttt    3000
tagagcggac taaaaaaaga ggttttgtga tcccttttg ggctccacaa gcccaagtct    3060
tggcgcatcc atccacggga ggatttttaa ctcattgtgg atggaattcg actctagaga    3120
gtgtagtaag tggtattcca cttatagcat ggccattata cgcagaacag aagatgaatg    3180
cggttttgtt gagtgaagat attcgtgcgg cacttaggcc gcgtgccggg gacgatgggt    3240
tagttagaag agaagaggtg gctagagtgg taaaaggatt gatggaaggt gaagaaggca    3300
aaggagtgag gaacaagatg aaggaattga aggaagcagc ttgtagggta ttgaaggatg    3360
atgggacttc gacaaaagca cttagtcttg tggccttaaa gtggaaagcc cacaaaaaag    3420
agttagagca aaatggcaac cactaactcg ag                                  3452
```

<210> SEQ ID NO 48
<211> LENGTH: 38
<212> TYPE: DNA
<213> ORGANISM: artificial sequence
<220> FEATURE:
<223> OTHER INFORMATION: Primer 23

<400> SEQUENCE: 48
ggtaccgtga aaggagatat acatatggcg gtgcaggc                            38

<210> SEQ ID NO 49
<211> LENGTH: 31
<212> TYPE: DNA
<213> ORGANISM: artificial sequence
<220> FEATURE:
<223> OTHER INFORMATION: Primer 24

<400> SEQUENCE: 49
gagctcaagc ttagcctgat gcacttaatg g                                   31

<210> SEQ ID NO 50
<211> LENGTH: 35
<212> TYPE: DNA
<213> ORGANISM: artificial sequence
<220> FEATURE:
<223> OTHER INFORMATION: Primer 25

<400> SEQUENCE: 50
ggatccgtga aaggagatat accatggagg aatcc                               35

<210> SEQ ID NO 51
<211> LENGTH: 33
<212> TYPE: DNA
<213> ORGANISM: artificial sequence
<220> FEATURE:
<223> OTHER INFORMATION: Primer 26

<400> SEQUENCE: 51
aagcttttag tggttgccat ttgctctaa ctc                                  33

<210> SEQ ID NO 52
<211> LENGTH: 32
<212> TYPE: DNA
<213> ORGANISM: artificial sequence
<220> FEATURE:
<223> OTHER INFORMATION: Primer 27

<400> SEQUENCE: 52
ctactcattt catatgtcac accccgcgtt aa                                    32

<210> SEQ ID NO 53
<211> LENGTH: 34
<212> TYPE: DNA
<213> ORGANISM: artificial sequence
<220> FEATURE:
<223> OTHER INFORMATION: Primer 28

<400> SEQUENCE: 53
catcttactg tcgacttagt acaacggtga cgcc                                  34

<210> SEQ ID NO 54
<211> LENGTH: 1971
<212> TYPE: DNA
<213> ORGANISM: artificial sequence
<220> FEATURE:
<223> OTHER INFORMATION: Nucleic acid sequence of a nucleic acid
      fragment inserted into expression vector pET29a encoding CPL
      (from Escherichia coli) and pHBA 1-hydroxylase (from Cadida
      parapsilosis).

<400> SEQUENCE: 54
catatgtcac accccgcgtt aacgcaactg cgtgcgctgc gctattttaa agagatccct      60
gccctggatc cgcaactgct cgactggctg ttgctggagg attccatgac aaaacgtttt     120
gaacagcagg gaaaaacggt aagcgtgacg atgatccgcg aagggtttgt cgagcagaat     180
gaaatccccg aagaactgcc gctgctgccg aaagagtctc gttactggtt acgtgaaatt     240
ttgttatgtg ccgatggtga accgtggctt gccggtcgta ccgtcgttcc tgtgtcaacg     300
ttaagcgggc cggagctggc gttacaaaaa ttgggtaaaa cgccgttagg acgctatctg     360
ttcacatcat cgacattaac ccgggacttt attgagatag gccgtgatgc cgggctgtgg     420
gggcgacgtt cccgcctgcg attaagcggt aaaccgctgt tgctaacaga actgtttttta     480 ccggcgtcac cgttgtacta agtcgacaag gagatataca tatggcggtg caggcgccgt     540
cgaagacgta cggtttccaa aaggctccaa tacaacttac atttgtcgtt gtaggtgccg     600
gtctcggggg agtcgccgct agtatttgcc tcagattggc aggccacaga gtcattttat     660
tagaagcagc tactgaattg ggtgaagttg agctggtat tcaaattcca ccaccatcaa     720
ccaagatttt aaaagcaatt ggcgtattgg atgcagttga taagtctcg attcatccac     780 atgatatctt ggtcaagaaa tataaaggtg aactttatc tacgcaaaac ttggtgcctt     840
atgttctgga gaaatacgat ggaatgtatt tacatattca cagggctgat tatcataaag     900
tattggttga tagagccgaa gaattggggg ttgaaatcca tacaaattca agagttgttg     960
atattgattt tgaaaagca actgtcacta ctgcaactgg aaaacaatac agtggtgatg    1020
tcattgtagg gtatgatgga gtcagatcac aaaccagagc tttattaact ggtgactctt    1080
ctggagctta cgatactggt gatttagcat accgtgcatt gattaaagtt gaagatatga    1140
agaaagttcc tggattggag aaattttacg ccaacccaaa catcaacttc tggtgggtc    1200 ccaccatgca cattgtcatg tatttcttgc acgaaggtaa aatctgtaat gttgttgcct    1260
tgtgccctga cacattacca aaaggagttt tgaaacaaga tgcatcacaa gaggaattat    1320

-continued

```
tagacttggt taaaggttgg gatcaagacc tcaccactgt tttcaaattg attacatcag    1380
tgagtaaatg gcgtttacaa gactcacgtg aattgaaaac gtgggtcaat tccaaaactg    1440
gcaattttat aatcttgggt gatgcttccc attcaaccct gccttatttg gccagtggtg    1500
catcgcaagc agttgaggat ggtgctgttc ttgctggatt attctccaag atcgaactgc    1560
gtgaccaaat ccctcaactt ttacaaatga cggagaattt gcgtaaatgg agaagttctc    1620
aagtggttag aggatctcat caatgtcaag atatttatca tttacccgat ggtgaattac    1680
aagaaattag agattcttat ttgtatgata aacaaccgga attgggatgt cccaatagat    1740
ttgctgatcc agttttccaa gattttcttt ggggatataa tgcttttgat gaagttgaaa    1800
gagcttggaa ggagtttaag gctggtggta atccaactta tacttatcct aacttgtata    1860
aaccaaagag tagtggtgag aaggatgtgt caggtggagg agcagcagca acccttgctg    1920
ctggtaatac cccagctgct ccattaagtg catcaggcta agcttgtcga g              1971
```

HIGH LEVEL PRODUCTION OF ARBUTIN IN GREEN PLANTS

FIELD OF THE INVENTION

The invention relates to the field of plant gene expression, molecular biology, and microbiology. Methods and materials are presented for the production of hydroquinone glucoside (arbutin) in genetically modified green plants and microorganisms and in vitro.

BACKGROUND OF THE INVENTION

Arbutin (hydroquinone glucoside) and its aglycone, hydroquinone, are compounds used as skin whitening agents. Skin pigmentation is mainly determined by the amount of melanin produced by melanocytes. The biosynthetic pathway leading to melanin formation begins with the conversion of tyrosine to dihydroxyphenylalanine (DOPA) via the enzyme tyrosinase (EC 1.14.18.1). Inhibition of tyrosinase decreases the amount of melanin produced by the melanocytes, leading to the depigmentation of the skin. Arbutin and monoester derivatives of arbutin have been shown to decrease the amount of melanin produced by melanocytes by inhibiting tyrosinase (U.S. Pat. No. 6,306,376).

Hydroquinone and derivatives of hydroquinone, such as hydroquinone ethers, are also used as depigmenting agents. However, negative side effects from the use of these compounds have been reported. These compounds are particularly irritating and cytotoxic to melanocytes (U.S. Pat. No. 6,306,376). The use of arbutin as a depigmenting agent is preferred over hydroquinone because of arbutin's reduced toxicity in comparison to the aglycone.

Arbutin has also been reported to be useful as an antioxidant, an antimicrobial agent, an anti-inflammatory agent, and possibly as an inhibitor of carcinogenesis (melanoma). However, arbutin's commercial use has been limited due to its high cost. No low-cost commercial production route to this chemical exists. Current methods for production include chemical synthesis (U.S. Pat. No. 3,201,385; U.S. Pat. No. 6,388,103; and JP 62-226974A); extraction from plants naturally producing arbutin; bio-transformation using either microbial hosts or plant cell cultures, seeds, or seedlings expressing suitable glucosyltransferases contacted with hydroquinone and UDP-glucose (Arend et al., *Phytochemistry*, 53: 187–193 (2000); Arend et al., *Biotech. Bioeng.*, 76(2): 126–131 (2001); Hefner et al., *Bioorg. Med. Chem.*, 10: 1731–1741 (2002); and JP 07224083A), or by a similar process where a mixture of glucose and hydroquinone is contacted with a β-glucosidase (JP 05176785A).

Chemical synthesis is not a cost-effective way to produce arbutin. Chemical synthesis methods usually require expensive starting materials, various expensive and toxic solvents and catalysts, significant energy input, and a subsequent purification step to remove impurities. The investment in non-renewable resources is both expensive and environmentally unfriendly.

Many higher plants naturally produce arbutin. Members of the Eracaceae, Rosaceae, and Saxifragaceae families have been reported to produce arbutin in amounts up to 20% dry weight (leaf). However, these plants suffer from poor agronomic performance (Arend et al., *Phytochemistry*, 53:187–193 (2000)). Cost-effective production of arbutin in plants requires a crop plant species with high agronomic performance and an established processing infrastructure.

Even though various routes to the production of arbutin exist, the possibility of using green plants with high agronomic performance for the commercial production of chemicals has become an increasingly attractive alternative. As opposed to organic synthesis, green plants constitute a renewable energy source. Because of their unique photosynthetic capability, the only raw materials that are required to produce carbon-based compounds in green plants are carbon dioxide, water and soil, with sunlight providing the ultimate energy source. In comparison to existing fermentation facilities that are limited in size, green plants constitute a huge available biomass that could easily accommodate large-scale production of chemicals, even those requiring high-volume, low-cost applications.

Even though in vivo plant production offers a larger potential biomass, microbial production is also an attractive alternative in comparison to expensive, energy-intensive, and environmentally unfriendly chemical synthesis. Industrial microbes can be genetically modified to produce the desired genetic end product. Hefner et al. (*Bioorg. Med. Chem.*, 10:1731–1741 (2002)) produced arbutin by exogenously supplying hydroquinone, a toxic and expensive substrate, to either cell suspension cultures of *Rauvolfia serpentina* expressing an endogenous hydroquinone glucosyltransferase (HQ GT) or to recombinant *E. coli* cells expressing the same enzyme. However, suitable recombinant microorganisms modified to produce commercially useful levels of arbutin currently do not exist.

Ran et al. (*J. Am. Chem. Soc.*, 123:10927–10934 (2001)) teach a method to produce hydroquinone using a microbial catalyst to convert glucose to the intermediate quinic acid. The quinic acid is subsequently isolated and chemically converted into hydroquinone. Ran et al. (supra) postulate that glucose could theoretically be converted into hydroquinone via a pHBA intermediate using the pHBA 1-hydroxylase activity of *Candida parapsilosis*. However, Ran et al. do not teach the isolating of the pHBA 1-hydroxylase gene, the sequence of the gene, nor a method to produce arbutin in plants and microbes.

The problem to be solved therefore is the lack of methods and materials to produce arbutin (hydroquinone glucoside) in transgenic plants, in microorganisms, or in vitro at commercially-useful levels.

SUMMARY OF THE INVENTION

Embodiments of the present invention include expressing either functional CPL (see SEQ ID NO:30)(targeted to the chloroplast for production in green plants or non-targeted for cytosolic microbial expression) and/or HCHL (see SEQ ID NO:38)(cytosolic) for the increased production of pHBA. In a preferred embodiment in green plants or in microbes, CPL and HCHL are coexpressed to maximize pHBA production. The pHBA produced can act as a substrate for the novel enzyme pHBA 1-hydroxylase (see SEQ ID NO:23)(decarboxylating) where it is converted into hydroquinone. A UDP-glucosyltransferase either endogenous to the host cell or recombinantly engineered into the host cell (see SEQ ID NO:42) glucosylates the hydroquinone to form hydroquinone glucoside (arbutin). In a preferred embodiment, the UDP-glucosyltransferase used in the present invention preferentially glucosylates hydroquinone over pHBA or other phenolic metabolites.

Applicants' preferred method in green plants produced recovered hydroquinone glucoside that was greater than 10% per dry weight of plant leaf biomass; a more preferred method produced recovered hydroquinone glucoside that was greater than 15% per dry weight of plant leaf biomass;

and the most preferred method produced recovered hydroquinone glucoside that was greater than 20% per dry weight of plant leaf biomass.

A preferred embodiment of the invention is a microbial cell transformed with a plasmid carrying a synthetic operon allowing expression of CPL, pHBA 1-hydroxylase, and *arabidopsis* hydroquinone glucosyltransferase (FIG. 6) and supplied with a suitable carbon source. pHBA may be supplied to the microorganism possessing a recombinant pHBA 1-hydroxylase enzyme in the absence of CPL. Alternatively, hydroquinone may be supplied to the microorganism possessing a recombinant hydroquinone glucosyltransferase enzyme but in the absence of CPL and pHBA 1-hydroxylase enzyme. Alternatively, hydroquinone glucoside can be produced using a mixed microbial culture having a recombinant hydroquinone-producing microorganism and a hydroquinone glucoside-producing organism containing the described components, at a cell density of each recombinant microorganism of about $1 \times 10^6$ to about $2 \times 10^{10}$ cells/mL and with an excess of hydroquinone-producing microorganism to hydroquinone glucoside-producing microorganism in a cell ratio of greater than 1:1 to about 1:20, to produce hydroquinone glucoside. The method may use the microbes sequentially or in a single culturing medium.

A preferred embodiment of this invention is a pHBA 1-hydroxylase enzyme from *Candida parapsilosis* that has a Km of <1 μM and a Kcat of at least ~9.5/sec for pHBA and a glucosyltransferase enzyme from *Arabidopsis thaliana* (UGT72B1) that has a Km of <1 μM and a Kcat of at least 42/sec for hydroquinone.

Included in the invention are nucleic acid and amino acids as set forth in the Sequence Listing, expression cassettes, and transgenic green plants and microbes containing the described components.

BRIEF DESCRIPTION OF THE DRAWINGS SEQUENCE DESCRIPTIONS, AND BIOLOGICAL DEPOSITS

The invention can be more fully understood from the sequence listing, the Figures, a biological deposit, and the detailed description that together form this application.

FIG. 1 shows the enzyme pathway to produce arbutin from pHBA in transgenic plants. The modified CPL converts chorismate to pHBA in the chloroplast while expressed HCHL converts 4-coumaroyl-CoA to pHBA in the cytosol. The fungal enzyme pHBA 1-hydroxylase converts pHBA to hydroquinone. A UDP-glucosyltransferase glucosylates the hydroquinone to produce hydroquinone glucoside. The hydroquinone glucoside (arbutin) is subsequently stored and accumulated in the plant's vacuoles.

Figure 1:
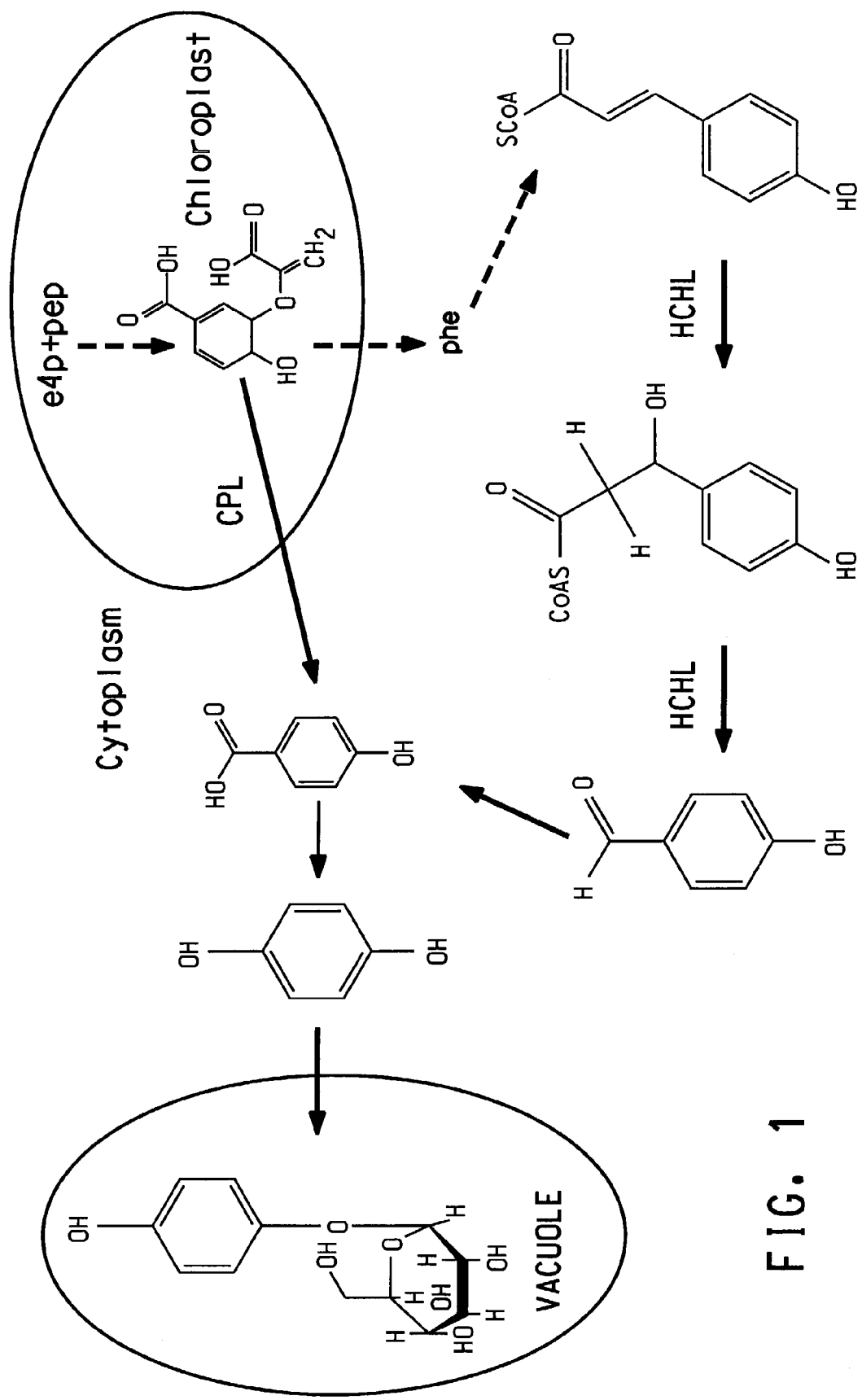

The following sequence descriptions and the sequence listing attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

SEQ ID NO:1 is the sequence of the first 24 amino acids (not including the initial methionine) of the pHBA 1-hydroxylase, determined by Edman degradation of the enzyme purified from *Candida parapsilosis* (ATCC 7336).

SEQ ID NO:2 is the amino acid sequence of peptide 4, a fragment generated by tryptic digestion of the purified pHBA 1-hydroxylase enzyme.

SEQ ID NO:3 is the amino acid sequence of peptide 5, a fragment generated by tryptic digestion of the purified pHBA 1-hydroxylase enzyme.

SEQ ID NO:4 is the amino acid sequence of peptide 6, a fragment generated by tryptic digestion of the purified pHBA 1-hydroxylase enzyme.

SEQ ID NO:5 is the nucleotide sequence of a 5' primer useful in a RT-PCR experiment for amplifying a 518 nt fragment of the pHBA 1-hydroxylase transcript from cDNA derived from *Candida parapsilosis* cells grown in the presence of pHBA as sole carbon source.

SEQ ID NO:6 is the nucleotide sequence of a 3' primer useful in a RT-PCR experiment for amplifying a 518 bp fragment of the pHBA 1-hydroxylase transcript from cDNA derived from *Candida parapsilosis* cells grown in the presence of pHBA as sole carbon source.

SEQ ID NO:7 is the amino acid sequence of the pHBA 1-hydroxylase protein that was reverse-translated into the 5' primer useful for amplifying a 518 bp fragment of the pHBA 1-hydroxylase transcript from cDNA derived from *Candida parapsilosis* cells grown in the presence of pHBA as sole carbon source.

SEQ ID NO:8 is the amino acid sequence of the pHBA 1-hydroxylase protein that was reverse-translated into the 3' primer useful for amplifying a 518 bp fragment of the pHBA 1-hydroxylase transcript from cDNA derived from *Candida parapsilosis* cells grown in the presence of pHBA as sole carbon source.

SEQ ID NO:9 is the consensus nucleotide sequence of the DNA fragment of the pHBA 1-hydroxylase transcript that can be amplified from cDNA derived from *Candida parapsilosis* cells grown in the presence of pHBA as sole carbon source using the primers of SEQ ID NO:5 and SEQ ID NO:6.

SEQ ID NO:10 is the deduced amino acid sequence of the DNA fragment of the pHBA 1-hydroxylase transcript that can be amplified from cDNA derived from *Candida parapsilosis* cells grown in the presence of pHBA as sole carbon source using the primers of SEQ ID NO:5 and SEQ ID NO:6.

SEQ ID NO:11 is a primer that is useful in a 3'RACE experiment for synthesis of cDNA from RNA of *Candida parapsilosis* cells grown on pHBA as sole carbon source.

SEQ ID NO:12 is the 5'primer useful in a 3'RACE experiment for amplifying a 1159 bp fragment of the pHBA 1-hydroxylase transcript from cDNA derived from *Candida parapsilosis* cells grown in the presence of pHBA as sole carbon source.

SEQ ID NO:13 is the 3'primer useful in a 3'RACE experiment for amplifying a 1159 nt DNA fragment of the pHBA 1-hydroxylase transcript from cDNA derived from *Candida parapsilosis* cells grown in the presence of pHBA as sole carbon source.

SEQ ID NO:14 is the consensus nucleotide sequence obtained by the alignment of SEQ ID NO:9 with the DNA sequence that can be amplified with primers of SEQ ID NO:12 and SEQ ID NO:13 from cDNA derived from *Candida parapsilosis* cells grown in the presence of pHBA as sole carbon source.

SEQ ID NO:15 is the nucleotide sequence of the 1440 bp open reading frame in SEQ ID NO:14 representing a variant of the pHBA 1-hydroxylase open reading frame.

SEQ ID NO:16 is the deduced amino acid sequence of the 1440 bp open reading frame in SEQ ID NO:14 representing a variant of the pHBA 1-hydroxylase open reading frame.

SEQ ID NO:17 is a primer that is useful in a 5'RACE experiment for synthesis of cDNA from RNA of *Candida parapsilosis* cells grown on pHBA as sole carbon source.

SEQ ID NO:18 is a 5' primer that is useful in a 5'RACE experiment for amplifying a 264 bp fragment representing the 5' end of the pHBA 1-hydroxylase transcript.

SEQ ID NO:19 is a 3' primer that is useful in a 5'RACE experiment for amplifying a 264 bp fragment representing the 5' end of the pHBA 1-hydroxylase transcript.

SEQ ID NO:20 is the nucleotide sequence of the 264 bp DNA fragment obtained by 5'RACE representing the 5'end of the pHBA 1-hydroxylase transcript.

SEQ ID NO:21 is the consensus nucleotide sequence of the pHBA 1-hydroxylase transcript that was obtained by alignment of DNA sequences obtained in RT-PCR, 3'RACE and 5'RACE experiments.

SEQ ID NO:22 is the consensus nucleotide sequence encoding the pHBA 1-hydroxylase enzyme present on the transcript that was obtained by alignment of DNA sequences obtained in RT-PCR, 3'RACE and 5'RACE experiments.

SEQ ID NO:23 is the deduced amino acid sequence of the pHBA 1-hydroxylase present on the transcript that was obtained by alignment of DNA sequences obtained in RT-PCR, 3'RACE and 5'RACE experiments.

SEQ ID NO:24 is the 3' primer useful for introducing the ORF of the pHBA 1-hydroxylase gene in the *Escherichia coli* expression vector, pET-29a(+).

SEQ ID NO:25 is the 5' primer useful for introducing the ORF of the pHBA 1-hydroxylase gene in the *Escherichia coli* expression vector, pET-29a(+).

SEQ ID NO:26 is the nucleotide sequence encoding the pHBA 1-hydroxylase in the *Escherichia coli* expression vector, pET-29a(+).

SEQ ID NO:27 is the 5' primer useful for amplifying the nucleotide sequence of the *E. coli* ubiC gene (GenBank® Accession No. M96268) using genomic DNA from *E. coli* strain W3110 and its insertion into the *Escherichia coli* expression vector pET-24a(+).

SEQ ID NO:28 is the 3' primer useful for amplifying the nucleotide sequence of the *E. coli* ubiC gene using genomic DNA from *E. coli* strain W3110 and its insertion into the *Escherichia coli* expression vector pET24a(+).

SEQ ID NO:29 is the nucleotide sequence of the ORF of the PCR-amplified CPL in *Escherichia coli* expression vector, pET-24a(+).

SEQ ID NO:30 is the deduced primary amino acid sequence of the ORF of the PCR-amplified CPL in *Escherichia coli* expression vector, pET-24a(+).

SEQ ID NO:31 is the 5' primer useful for amplifying the nucleotide sequence encoding the transit peptide from the Rubisco small subunit precursor from plasmid pTSS1–91 (#2)-IBI and its insertion into expression vector pET-24a-CPL.

SEQ ID NO:32 is the 3' primer useful for amplification of the nucleotide sequence encoding the transit peptide from the Rubisco small subunit precursor from plasmid pTSS1-91(#2)-IBI and its insertion into expression vector pET-24a-CPL.

SEQ ID NO:33 is the nucleotide sequence of the ORF of the PCR-amplified TP-CPL in *Escherichia coli* expression vector, pET24a-TP-CPL.

SEQ ID NO:34 is the deduced primary amino acid sequence of the ORF of the PCR-amplified TP-CPL in *Escherichia coli* expression vector, pET24a-TP-CPL.

SEQ ID NO:35 is the 5' primer useful for amplifying a shortened 3'NOS terminator sequence from plasmid pMH40 and its insertion into plasmid pML3 yielding plasmid pML63.

SEQ ID NO:36 is the 3' primer useful for amplifying a shortened 3'NOS terminator sequence from plasmid pMH40 and its insertion into plasmid pML3 yielding plasmid pML63.

SEQ ID NO:37 is the nucleotide sequence of the HCHL gene from *Pseudomonas putida* (DSM12585) (Muheim and Lerch, *Appl. Microbiol. Biotechnol.*, 51(4):456–461 (1999)) useful for producing pHBA in transgenic plants.

SEQ ID NO:38 is the deduced amino acid sequence of the HCHL protein of *Pseudomonas putida* (Muheim and Lerch, supra) useful for producing pHBA in transgenic plants.

SEQ ID NO:39 is the 5' primer useful for amplifying the nucleotide sequence of the *Arabidopsis thaliana* UGT72B1 gene using plasmid DNA from a full length cDNA clone of the UGT72B1 gene and its insertion into the *Escherichia coli* expression vector pET-28a(+).

SEQ ID NO:40 is the 3' primer useful for amplifying the nucleotide sequence of the *Arabidopsis thaliana* UGT72B1 gene using plasmid DNA from a full length cDNA clone of the UGT72B1 gene and its insertion into the *Escherichia coli* expression vector pET-28a(+).

SEQ ID NO:41 is the nucleotide sequence encoding the *Arabidopsis thaliana* UGT72B1 UDP-glucosyltransferase.

SEQ ID NO:42 is the amino acid sequence of the *Arabidopsis thaliana* UGT72B1 enzyme deduced from the nucleotide sequence of the *Arabidopsis thaliana* UGT72B1 gene.

SEQ ID NO:43 is the 5' primer useful for amplifying the nucleotide sequence of the pHBA 1-hydroxylase gene from *Candida parapsilosis* using plasmid DNA of a pET29a(+) plasmid containing the pHBA 1-hydroxylase gene (SEQ ID NO:26) and its insertion into the *Escherichia coli* expression vector pET24a(+).

SEQ ID NO:44 is the 3' primer useful for amplifying the nucleotide sequence of the pHBA 1-hydroxylase gene from *Candida parapsilosis* using plasmid DNA of a pET29a(+) plasmid containing the pHBA 1-hydroxylase gene (SEQ ID NO:26) and its insertion into the *Escherichia coli* expression vector pET24a(+).

SEQ ID NO:45 is the 5' primer useful for amplifying the nucleotide sequence encoding the *Arabidopsis thaliana*

UGT72B1 enzyme using plasmid DNA of a pET28a(+) plasmid containing the *Arabidopsis thaliana* UGT72B1 gene and its insertion into the *Escherichia coli* expression vector pET24a(+).

SEQ ID NO:46 is the 3' primer useful for amplifying the nucleotide sequence encoding the *Arabidopsis thaliana* UGT72B1 enzyme using plasmid DNA of a pET28a(+) plasmid containing the *Arabidopsis thaliana* UGT72B1 gene and its insertion into the *Escherichia coli* expression vector pET24a(+).

SEQ ID NO:47 is the nucleotide sequence of a nucleic acid fragment encoding the CPL, pHBA 1-hydroxylase, and UGT72B1 enzymes in the *Escherichia coli* expression vector pET24a(+).

SEQ ID NO:48 is the 5' primer useful for amplifying the nucleotide sequence encoding the pHBA 1-hydroxylase from *Candida parapsilosis* using plasmid DNA of a pET29a (+) plasmid containing the pHBA 1-hydroxylase gene (SEQ ID NO:26) and its insertion into the *Escherichia coli* expression vector pMPMT3.

SEQ ID NO:49 is the 3' primer useful for amplifying the nucleotide sequence encoding the pHBA 1-hydroxylase from *Candida parapsilosis* using plasmid DNA of a pET29a (+) plasmid containing the pHBA 1-hydroxylase gene (SEQ ID NO:26) and its insertion into the *Escherichia coli* expression vector pMPMT3.

SEQ ID NO:50 is the 5' primer useful for amplifying the nucleotide sequence encoding the *Arabidopsis thaliana* UGT72B1 enzyme using plasmid DNA of a pET28a(+) plasmid containing the *Arabidopsis thaliana* UGT72B1 gene and its insertion into the *Escherichia coli* expression vector pCL1920.

SEQ ID NO:51 is the 3' primer useful for amplifying the nucleotide sequence encoding the *Arabidopsis thaliana* UGT72B1 enzyme using plasmid DNA of a pET28a(+) plasmid containing the *Arabidopsis thaliana* UGT72B1 gene and its insertion into the *Escherichia coli* expression vector pCL1920.

SEQ ID NO:52 is the 5' primer useful for amplifying the nucleotide sequence encoding the *E. coli* CPL enzyme using genomic DNA of *E. coli* and its insertion into the *Escherichia coli* expression vector pET29a(+).

SEQ ID NO:53 is the 3' primer useful for amplifying the nucleotide sequence encoding the *E. coli* CPL enzyme using genomic DNA of *E. coli* and its insertion into the *Escherichia coli* expression vector pET29a(+).

SEQ ID NO:54 is the nucleotide sequence of a nucleic acid fragment encoding the CPL and pHBA 1-hydroxylase enzymes in the *Escherichia coli* expression vector pET29a (+).

BRIEF DESCRIPTION OF BIOLOGICAL DEPOSITS

Applicants have made the following biological deposit under the terms of the Budapest Treaty on the International Recognition of the Deposit of Microorganisms for the purposes of Patent Procedure:

| Depositor Identification Reference | Int'l. Depository, Designation | Date of Deposit |
|---|---|---|
| Plasmid pZBL1 | ATCC 209128 | Jun. 24, 1997 |

As used herein, "ATCC" refers to the American Type Culture Collection International Depository located at 10801 University Boulevard, Manassas, Va. 20110-2209, U.S.A. The "ATCC No." is the accession number to cultures on deposit with the ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The Applicants have solved the stated problem by providing transgenic plants and microorganisms that produce commercially useful levels of arbutin (4-hydroxyphenyl-β-D-glucopyranoside; CAS 487-76-7). An in vivo method relies upon transgenic plants that produce increased levels of the initial substrate, para-hydroxybenzoic acid (pHBA), in a novel biosynthetic pathway engineered to produce arbutin. Most plants naturally produce a very low level of pHBA through a pathway that is not very well understood. Plants can be genetically engineered to produce high levels of pHBA either by functional expression of the bacterial protein chorismate pyruvate lyase (CPL) or by the expression of 4-hydroxycinnamoyl-CoA hydratase/lyase (HCHL), or a combination of both. The pHBA produced is converted to hydroquinone using a novel fungal protein, pHBA 1-hydroxylase, isolated from *Candida parapsilosis* (ATCC 7336). The hydroquinone produced is rapidly glucosylated by an endogenous plant UDP-glucosyltransferase. Optionally, a foreign UDP-glucosyltransferase (e.g., *arabidopsis* UGT72B1) can be introduced into the transformed plant cell. The hydroquinone glucoside (arbutin) is subsequently sequestered in the plant's vacuoles.

Transgenic plants (tobacco and *arabidopsis*) were modified to functionally express a gene encoding a modified version of the enzyme chorismate pyruvate lyase (CPL). CPL catalyzes the direct conversion of 1 mol of chorismate to 1 mol of pyruvate and 1 mol of pHBA. Transgenic plants can also be modified to functionally express a gene encoding a 4-hydroxycinnamoyl-CoA hydratase/lyase (HCHL) which catalyzes the conversion of 4-coumaroyl-CoA to pHBA. Transgenic plants are disclosed that were engineered to co-express both CPL and HCHL or any other enzyme or combination of enzymes that are suitable for high-level production of the pHBA precursor that is subsequently converted to hydroquinone and, ultimately, to arbutin.

The pHBA produced in the transgenic plants is converted to hydroquinone by functional expression of a gene encoding a pHBA 1-hydroxylase. The last step of the method relies on a functionally expressed UDP-glucosyltransferase gene. The UDP-glucosyltransferase can be either endogenous to the plant or recombinantly introduced into the plant. This enzyme converts the produced hydroquinone to hydroquinone glucoside (arbutin).

Regardless of the particular combination of the enzymes used, Applicants' preferred method produced recovered hydroquinone glucoside that was greater than 10% per dry weight of plant leaf biomass. Applicants' more preferred method produced recovered hydroquinone glucoside that was greater than 15% per dry weight of plant leaf biomass. Applicants' most preferred method produced recovered hydroquinone glucoside that was greater than 20% per dry weight of plant leaf biomass.

The Applicants use a UDP-glucosyltransferase (UGT72B1; GenBank® 116337.1) from *arabidopsis* that shows significant activity towards hydroquinone (turnover number of 42/sec). This turnover number was significantly higher than other UDP-glucosyltransferases reported to use hydroquinone as a substrate (Hefner et al., *Biorg. Med. Chem.*, 10:1731–1741 (2002); Arend et al., *Phytochemistry*, 53:187–193 (2000)).

The unique usefulness of the enzyme for conjugation of hydroquinone is exemplified (see Example 7) by a catalytic efficiency expressed as kcat (s$^{-1}$)/Km (µM) of 140 that clearly exceeds the efficiency of any other previously disclosed glucosyltransferase enzymes that has activity with hydroquinone. The molecular identification of pHBA 1-hydroxylase and hydroquinone glucosyltransferase genes enable arbutin production in microbial systems such as *E. coli*. To this end, the pHBA 1-hydroxylase gene is expressed in *E. coli* cells in combination with a chorismate pyruvate lyase (CPL) gene and a suitable glucosyltransferase gene (Example 6). Expressing these three enzymes in *E. coli* provides a route to arbutin from a cheap fermentable carbon source (such as glucose) by creating a three-step pathway from chorismate to arbutin (FIG. 1).

Accordingly, preferred polypeptides of the instant invention are those active proteins that are at least 80% identical to the amino acid sequence identified herein. More preferred amino sequences are at least 90% identical to the sequences identified herein. Most preferred are amino acid sequences that are at least 95% identical to the amino acid fragments reported herein. Similarly, preferred nucleic acid sequences corresponding to the instant ORF are those encoding active proteins and which are at least 80% identical to the nucleic acid sequences identified herein. More preferred nucleic acid sequences are at least 90% identical to the sequences identified herein. Most preferred are nucleic acid sequences that are at least 95% identical to the nucleic acid sequences reported herein.

The Applicants also provide a method of producing arbutin from a simple carbon source in microbes. A microorganism (*E. coli*), genetically modified to produce increased levels of pHBA substrate, is subsequently engineered to produce a recombinant version of pHBA 1-hydroxylase that converts pHBA into hydroquinone. A UDP-glucosyltransferase (*arabidopsis* UGT72B1) that is also expressed in the same microbial strain rapidly glucosylates the hydroquinone to produce arbutin. (See U.S. Ser. No. 10/359,369 incorporated in its entirety by reference.)

This strain produced hydroquinone by converting endogenous pools of chorismate to pHBA that is then converted to hydroquinone by pHBA 1-hydroxylase. Production of arbutin from glucose in this case was achieved by co-cultivation of two *E. coli* strains expressing CPL and pHBA 1-hydroxylase and the hydroquinone-specific glucosyltransferase described in Example 6, respectively.

The feasibility of a fermentative route to arbutin from glucose uses a pathway provided by CPL from *E. coli*, pHBA 1-hydroxylase from *Candida parapsilosis*, and a glucosyltransferase enzyme from *Arabidopsis thaliana*. Expression of the first two enzymes in *E. coli* leads to formation of hydroquinone that diffuses or is actively excreted into the medium and is taken up by cells expressing the hydroquinone-specific glucosyltransferase. After synthesis in the *E. coli* cell the hydroquinone glucoside is again diffusing or actively excreted into the medium.

All co-factors, co-enzymes and co-substrates required for these pathways (such as FAD, NADH, $O_2$, and UDPG) are present in the *E. coli* cytoplasm. *E. coli* strains with elevated levels of chorismate resulting from increased flux of carbon into the shikimate pathway have been disclosed (Berry et al., *Trends Biotech*, 14(7):250–256 (1996); Bongaerts et al., *Metabolic Engineering*, 3(4):289–300 (2001); Tatarko and Romeo T., *Curr. Microbiol.*, 43(1):26–32 (2001); U.S. Pat. No. 6,210,937 B1; U.S. Pat. No. 5,776,736 A; and WO 73484 A1) and can be used to produce arbutin from glucose using the molecular tools described below.

In this disclosure, a number of terms and abbreviations are used. The following definitions are provided.

"Polymerase chain reaction" is abbreviated "PCR".

"Para-hydroxybenzoic acid" or "p-hydroxybenzoic acid" is abbreviated "pHBA".

"Chorismate pyruvate lyase" is abbreviated "CPL" and refers to a gene encoding an enzyme which catalyzes the conversion of chorismate to pyruvate and pHBA. A chorismate pyruvate lyase expression cassette having the structure: P-T-C-D-CPL, wherein P is a promoter suitable for driving the expression of a chorismate pyruvate lyase gene; T is a nucleic acid molecule encoding a Rubisco chloroplast transit peptide; C is a nucleic acid molecule encoding a Rubisco chloroplast transit peptide cleavage site; and D is a nucleic acid molecule encoding four contiguous amino acids of the N-terminal portion of a Rubisco chloroplast transit peptide donor polypeptide; CPL is a nucleic acid molecule encoding chorismate pyruvate lyase enzyme having the amino acid sequence set forth in SEQ ID NO:30; and P, T, C, D, and CPL are operably linked with each other "4-hydroxycinnamoyl-CoA hydratase/lyase" is abbreviated "HCHL" and refers to an enzyme that catalyzes the hydration of the double bond of a hydroxycinnamoyl CoA thioester followed by a retro aldol cleavage reaction that produces a benzoyl aldehyde and acetyl CoA.

The terms "para-hydroxybenzoic acid 1-hydroxylase", "para-hydroxybenzoic acid 1-hydroxylase (decarboxylating)", "para-hydroxybenzoate 1-hydroxylase", and "pHBA 1-hydroxylase" are used interchangeably and refer to the nucleic acid fragment isolated from *Candida parapsilosis* (ATCC 7336) encoding an enzyme which catalyzes the conversion of pHBA to hydroquinone (Eppink et al., *J. Bacteriol.*, 179(2):6680–6687 (1997)).

The terms "hydroquinone glucoside" and "arbutin" refer to a conjugate comprising hydroquinone and a glucose molecule.

The terms "p-hydroxybenzoic acid glucoside" and "pHBA glucoside" refer to a conjugate comprising pHBA and a glucose molecule.

The terms "UDP-glucosyltransferase" and "glucosyltransferase" are abbreviated as "GT" and refer to enzymes involved in the formation of glucose conjugated molecules. Such proteins catalyze a reaction between UDP-glucose and an acceptor molecule to form UDP and the glucosylated acceptor molecule. In most cases the hydroxyl group on C1 of β-D-glucose is attached to the acceptor molecule via a 1-O-β-D-linkage. UDP-glucosyltransferases that show significant activity towards hydroquinone as a substrate are termed "hydroquinone glucosyltransferases", abbreviated as "HG-GT".

The term "aglycone" refers to substrates of the present invention that lack a glucose moiety (i.e., hydroquinone and pHBA).

The term "pHBA derivative" refers to any conjugate of pHBA that may be formed in a plant as the result of the catalytic activity of the CPL enzyme.

The terms "transit peptide" or "chloroplast transit peptide" (abbreviated "TP") refer to the N-terminal portion of a chloroplast precursor protein that directs the latter into chloroplasts and is subsequently cleaved off by the chloroplast processing protease.

The term "chloroplast-targeting sequence" refers to any polypeptide extension that is attached to the N-terminus of a foreign protein for the purpose of translocation into the chloroplast. In the case of a naturally occurring chloroplast precursor protein, the transit peptide is considered to be the chloroplast-targeting sequence, although optimal uptake and proteolytic processing may depend in part on portions of the "mature" chloroplast protein.

The term "transit peptide donor sequence" refers to that portion of the chloroplast-targeting sequence that is derived from the first several (up to about 20) amino acids from the N-terminal portion of the chloroplast precursor protein. The transit peptide donor sequence is always downstream and immediately adjacent to the transit peptide cleavage site that separates the transit peptide from the mature chloroplast protein.

The term "chloroplast processing protease" refers to a protease enzyme capable of cleaving the scissile bond between the transit peptide and the mature chloroplast protein.

The term "transit peptide cleavage site" refers to a site between two amino acids in a chloroplast-targeting sequence at which the chloroplast processing protease acts.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. "Foreign" may also be used to describe a nucleic acid sequence not found in the wild-type host into which it is introduced. Foreign genes can comprise native genes inserted into a non-native organism, or chimeric genes. A "transgene" is a gene that has been introduced into the genome by a transformation procedure.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered. Numerous examples were compiled by Okamuro and Goldberg in *The Biochemistry of Plants*, Vol. 15, published by Academic Press, Burlington, Mass., pages 1–82, (1989). It is further recognized that since in most cases the exact boundaries of regulatory sequences have not been completely defined, nucleic acid fragments of different lengths may have identical promoter activity.

The "3' non-coding sequences" refer to DNA sequences located downstream of a coding sequence and include polyadenylation recognition sequences (usually limited to eukaryotic mRNA) and other sequences encoding regulatory signals capable of affecting mRNA processing or gene expression. The eukaryotic polyadenylation signal is usually characterized by affecting the addition of polyadenylic acid tracts to the 3' end of the mRNA precursor.

The term "operably linked" refers to nucleic acid sequences associated on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide (i.e., one from which any pre- or propeptides present in the primary translation product have been removed). "Precursor" protein refers to the primary product of translation of mRNA; i.e., with pre- and pro-peptides still present. Pre- and pro-peptides may be, but are not limited to, intracellular localization signals.

"Transformation" refers to the transfer of a nucleic acid fragment into the genome of a host organism, resulting in genetically stable inheritance. Host organisms containing the transformed nucleic acid fragments are referred to as "transgenic", "recombinant", or "transformed" organisms.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L., and Enquist, L. W., *Experiments with Gene Fusions*, Cold Spring Harbor Laboratory Cold Press Spring Harbor, N.Y. (1984) (hereinafter "Silhavy"); and by Ausubel, F. M. et al., *Current Protocols in Molecular Biology*, published by Greene Publishing Assoc. and Wiley-Interscience (1987) (hereinafter "Ausubel").

pHBA Production in Transgenic Plants Using CPL and HCHL pHBA is naturally occurring in nearly all plants, animals, and microorganisms, albeit in miniscule quantities. Many bacteria generate pHBA by way of chorismate, an important branchpoint intermediate in the synthesis of numerous aromatic compounds including phenylalanine, tyrosine, p-aminobenzoic acid, and ubiquinone. In *E. coli*, chorismate undergoes five different enzymatic reactions to yield five different products. The enzyme that is ultimately responsible for the synthesis of pHBA is chorismate pyruvate lyase, which is known as CPL. The latter is the product of the *E. coli* ubiC gene, which was independently cloned by two different groups (Siebert et al., *FEBS Lett* 307:347–350 (1992); Nichols et al., *J. Bacteriol.* 174:5309–5316 (1992)). The enzyme is a 19 kDa monomeric protein with no known co-factors or energy requirements. Through elimination of the $C_3$ enolpyruvyl side chain of its sole substrate, CPL catalyzes the direct conversion of 1 mol of chorismate to 1 mol of pyruvate and 1 mol of pHBA. Recombinant CPL has been over-expressed in *E. coli*, purified to homogeneity, and partially characterized both biochemically and kinetically (Siebert et al., *Microbiology*, 140:897–904 (1994); Nichols et al., *J. Bacteriol.*, 174:5309–5316 (1992)). In addition, a detailed mechanism for the CPL enzyme reaction has also been proposed (Walsh et al., *Chem. Rev.*, 90:1105–1129 (1990)).

In plants, pHBA has been found in carrot tissue (Schnitzler et al., *Planta*, 188:594 (1992)), in a variety of grasses and crop plants (Lydon et al., *J. Agric. Food. Chem.*, 36:813 (1988)), in the lignin of poplar trees (Terashima et al., *Phytochemistry*, 14:1991 (1972)), and in a number of other plant tissues (Billek et al., *Oesterr. Chem.*, 67:401 (1966)). The fact that plants possess all of the necessary enzymatic machinery to synthesize pHBA suggests that they may be a useful platform for the production of this monomer. For example, as a renewable resource a plant platform would require far less energy and material consumption than either petrochemical or microbial methods for producing the monomer. Similarly, a plant platform represents a far greater available biomass for monomer production than a microbial system. Finally, the natural presence of pHBA in plants suggests that host toxicity (a result of overproduction of the compound) might not be a problem. Nevertheless, in spite of the obvious benefits of using plants as a means to produce pHBA, high-level production of the monomer has been elusive.

The metabolic fate of chorismate in plant tissues presents a difficult problem. Indeed, the production of pHBA from chorismate is vastly more complicated in higher plants than microbes since the former lack an enzyme that is functionally equivalent to CPL. For example, the biosynthetic pathway leading to pHBA in *Lithospermum erythrorhizon* is thought to consist of up to 10 successive reactions (Loscher and Heide, *Plant Physiol.*, 106:271–279 (1992)), each one presumably catalyzed by different enzymes. Moreover, most of the enzymes that catalyze these reactions have not been identified, nor have their genes been cloned. Even less information is available on how pHBA is synthesized in other plant species. To further complicate matters, those enzymes that are known to participate in plant pHBA production span two different pathways that are differentially regulated and located in different cellular compartments. Specifically, chorismate is an intermediate of the shikimate pathway which is largely confined to chloroplasts and other types of plastids (Siebert et al., *Plant Physiol.*, 112:811–819 (1996); Sommer et al., *Plant Cell Physiol.*, 39(11):1240–1244 (1998)), while all of the intermediates downstream from phenylalanine belong to the phenylpropanoid pathway, which takes place in both the cytosol and endoplasmic reticulum.

Transgenic plants that accumulate significantly higher levels of pHBA than wild-type plants have been described. For example, Kazufumi Yazaki (*Baiosaiensu to Indasutori*, 56(9):621–622 (1998)) discusses the introduction of the CPL encoding gene into tobacco for the production of pHBA in amounts sufficient to confer insect resistance. Similarly, Siebert et al. (*Plant Physiol.*, 112:811–819 (1996)) have demonstrated that tobacco plants (*Nicotiana tabacum*), transformed with a constitutively expressed chloroplast-targeted version of *E. coli* CPL (referred to as "TP-UbiC"), have elevated levels of pHBA that are at least three orders of magnitude greater than wild-type plants (WO 96/00788). The genetically modified tobacco plants contained only trace amounts of free, unconjugated pHBA. Virtually all of the compound (~98%) was converted into two glucose conjugates, a phenolic glucoside and an ester glucoside that were present in a ratio of about 3:1 (Siebert et al., *Plant Physiol.*, 112:811–819 (1996); Li et al., *Plant Cell Physiol.*, 38(7): 844–850 (1997)). Both glucose conjugates were 1-β-D- glucosides having a single glucose residue covalently attached to the hydroxyl or carboxyl group of pHBA. The best transgenic plant that was identified in this study had a total pHBA glucoside content of ~0.52% of dry weight (plant leaf tissue). Correcting for the associated glucose residue, the actual amount of pHBA that was produced in the transgenic tobacco plants was only about half of this value.

In more recent studies, the same artificial fusion protein was expressed in transformed tobacco cell cultures using both a constitutive promoter (Sommer et al., *Plant Cell Physiol.*, 39(11):1240–1244 (1998)) and an inducible promoter (Sommer et al., *Plant Cell Reports*, 17:891–896 (1998)). While the accumulation of pHBA glucosides was slightly higher than the original study with whole plants, in neither case did the levels exceed 0.7% of dry weight. In contrast, when TP-UbiC was examined in hairy root cultures of *Lithospermum erythrorhizon* (Sommer et al., *Plant Molecular Biology*, 39:683–693 (1999)) the pHBA glucoside content reached levels as high as 0.8% of dry weight, after correcting for the endogenous levels in the untransformed control cultures.

Although these studies demonstrate the feasibility of using genetic engineering to increase the level of pHBA in higher plants, the TP-UbiC artificial fusion protein described above is unable to generate the compound in commercially useful quantities. Obtaining such quantities will require increasing the pHBA content of an agronomically suitable plant to levels that are 10- to 20-fold higher than those previously reported. Thus, one or more modifications of the known systems are needed to achieve these levels. Since chorismate, the substrate for CPL, is synthesized in plastids, one potential area for improvement may lie in the design of a better chloroplast targeting sequence to achieve higher levels of enzyme activity in the cellular compartment of interest. There is a positive correlation between CPL enzyme activity and accumulation of pHBA glucosides that is apparent in several of the studies noted above (Siebert et al., *Plant Physiol.*, 112:811–819 (1996); Sommer et al., *Plant Cell Physiol.*, 39(11):1240–1244 (1998); Sommer et al., *Plant Cell Reports*, 17:891–896 (1998)). Furthermore, in none of these studies is there any evidence to suggest that the systems were saturated with CPL enzyme activity using the TP-UbiC artificial fusion protein.

Most naturally occurring chloroplast proteins are nuclear-encoded and synthesized as larger molecular weight precursors with a cleavable N-terminal polypeptide extension called a transit peptide. It is generally accepted that the latter contains all of the information that is necessary for translocation into the chloroplast. Although the mechanistic details of protein import remain to be elucidated, several important facts have emerged: (a) precursor uptake occurs post-translationally (Chua and Schmidt, *Proc. Natl. Acad. Sci.*, 75:6110–6114 (1978); Highfield and Ellis, *Nature*, 271: 420–424 (1978)) and is mediated by proteinacious receptors that exist in the chloroplast envelope membranes (Cline et al., *J. Biol. Chem.*, 260:3691–3696 (1985))); (b) ATP-hydrolysis is the sole driving force for translocation (Grossman et al., *Nature*, 285:625–628 (1980); Cline et al., supra); (c) fusion of a transit peptide to a foreign protein is at times, but not always, sufficient to trigger uptake into chloroplasts, both in vivo ((Van den Broeck et al., *Nature*, 313:358–362 (1985)); Schreier et al., *EMBO J.*, 4:25–32 (1985)) and in vitro (Wasmann et al., *Mol. Gen. Genet.*, 205:446–453 (1986)); and finally, (d) following chloroplast import, the transit peptide is proteolytically removed from the precursor protein to give rise to the "mature" polypeptide. Although the complete sequence of thousands of transit peptides are now known, manipulating these sequences to achieve optimal targeting and expression of foreign proteins in the chloroplast compartment of plants is still a matter of trial and error. Simply attaching a transit peptide to a foreign protein does not necessarily guarantee that it will be efficiently taken up by chloroplasts or properly processed. Even when the same targeting sequence is fused to different proteins, the results are completely unpredictable (Lubben et al., *The Plant Cell*, 1:1223–1230 (1989)), and the different passenger proteins are transported with different efficiencies. The reasons for this are not clear. However, it has been suggested that chloroplast uptake and removal of the transit peptide are somehow coupled, and that certain artificial fusion proteins are either not processed or processed ineffectively. For example, it has been shown that even very subtle changes in the vicinity of the natural cleavage site of the Rubisco small subunit precursor can lead to aberrant processing (Robinson and Ellis, *Eur. J. Biochem.*, 142:342–346 (1984); Robinson and Ellis, *Eur. J. Biochem.*, 152:67–73 (1985)) and diminished chloroplast uptake (Wasmann et al., *J. Biol. Chem.*, 263:617–619 (1988)).

Some degree of improvement has been achieved in this area by including in the chloroplast targeting sequence not only the transit peptide and the scissile bond, but also a small portion of the mature N-terminus of the transit peptide donor. Indeed, this approach has worked both in vivo and in vitro ((Van den Broeck et al., supra; Schreier et al., supra; Wasmann et al., supra; EP 0189707; U.S. Pat. No. 5,728,925; and U.S. Pat. No. 5,717,084)) for another bacterial protein, namely, neomycin phosphotransferase II (NPT-II). Thus, a chimeric protein consisting of the transit peptide of the Rubisco small subunit precursor plus the first 22 residues of mature Rubisco fused to the N-terminus of NPT-II was taken up by chloroplasts much better than a similar construct that only contained the transit peptide and scissile bond. However, this strategy is not foolproof as it is still associated with a high degree of unpredictability that is inextricably linked to the passenger protein. This is most readily seen in the literature attempts to target CPL to chloroplasts. For example, Sommer et al. (*Plant Cell Physiol.*, 39(11):1240–1244 (1998)) describe an analogous artificial fusion protein comprising the CPL gene product fused at its N-terminus to the transit peptide and first 21 amino acid residues of the Rubisco small subunit (e.g., "TP21UbiC"). This modification was undertaken to improve chloroplast uptake and processing, but the cells that contained the original construct, TP-UbiC, unexpectedly had much higher levels of both CPL enzyme activity and pHBA glucosides. Thus, application of the Wasmann et al. (supra) teaching had a detrimental effect when applied with a different protein.

A patent application (U.S. Ser. No. 09/855341, hereby incorporated by reference, now U.S. Pat. No. 6,683,231) teaches a chorismate pyruvate expression cassette (SEQ ID NO: 33, encoding a polypeptide having the amino acid sequence as set forth in SEQ ID NO: 34) useful for producing pHBA in plants. The polypeptide was efficiently transported into the cell chloroplast where it was subsequently proteolytically processed into an active chloroplast-targeted CPL. The chloroplast-targeted CPL enabled production of para-hydroxybenzoic acid in plants.

4-Hydroxycinnamoyl-CoA hydratase/lyase (HCHL) isolated from *Pseudomonas fluorescens* AN103 is another bacterial enzyme that when expressed in transgenic tobacco (*Nicotiana tabacum* cv. Xanthi XHFD8), resulted in significant accumulation of pHBA glucosides (Mayer et al., *Plant Cell.*, 13: 1669–1682 (2001)). Expression of HCHL in the transgenic plant's cytosol redirected the carbon flux from the phenylpropanoid pathway into the production of pHBA glucosides. HCHL catalyzes the conversion of 4-coumaroyl-CoA into pHBA, where endogenous UDP-glucosyltransferases glucosylated the pHBA.

Either functional CPL (targeted to the chloroplast for production in green plants or non-targeted for cytosolic microbial expression) or HCHL (cytosolic) for the increased production of pHBA may be expressed. In a preferred embodiment, CPL and HCHL are coexpressed to maximize pHBA production. The pHBA produced can act as a substrate for the novel enzyme pHBA 1-hydroxylase (decarboxylating) where it is converted into hydroquinone. A UDP-glucosyltransferase, either endogenous to the host cell or recombinantly engineered into the host cell, glucosylates the hydroquinone to form hydroquinone glucoside (arbutin). In a preferred embodiment, the UDP-glucosyltransferase used in the present invention preferentially glucosylates hydroquinone over pHBA or other phenolic metabolites.

CPL Expression Cassette

The present invention provides an expression cassette useful for the expression of a fully-active, modified version of chorismate pyruvate lyase (CPL) and the targeting of that polypeptide to the chloroplasts of the host plant. Typically the expression cassette will comprise (1) the cloned CPL gene under the transcriptional control of 5' and 3' regulatory sequences and (2) a dominant selectable marker. The present expression cassette may also contain a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal (usually limited to eukaryotes). In a preferred embodiment, the cassette will additionally contain sequences allowing for efficient targeting of the pHBA 1-hydroxylase enzyme to the plastid. These components will include a transit peptide as well as sequences encoding a portion of the transit peptide donor which contains a transit peptide cleavage site that is amenable to processing by the host plant cell chloroplast processing protease. Optionally, the cassette may also comprise one or more introns in order to facilitate expression. In another preferred embodiment the CPL gene is integrated into the chloroplast genome and expressed under the control of DNA sequence elements that allow for efficient translation and transcription in this organelle. A chorismate pyruvate lyase expression cassette of particular use in this invention has the structure:

P-T-C-D-CPL wherein P is a promoter suitable for driving the expression of a chorismate pyruvate lyase gene; T is a nucleic acid molecule encoding a Rubisco chloroplast transit peptide; C is a nucleic acid molecule encoding a Rubisco chloroplast transit peptide cleavage site; and D is a nucleic acid molecule encoding four contiguous amino acids of the N-terminal portion of a Rubisco chloroplast transit peptide donor polypeptide; CPL is a nucleic acid molecule encoding chorismate pyruvate lyase enzyme having the amino acid sequence set forth in SEQ ID NO:30; and P, T, C, D, and CPL are operably linked with each other;

HCHL Expression Cassette pHBA production can also be achieved through expression of 4-hydroxycinnamoyl-CoA hydratase/lyase (HCHL) enzyme of bacterial origin in the cytoplasm of a plant cell (Mayer et al., Plant Cell, 13 (7):1669–1682 (2001); Mitra et al., PLANTA, 215(1):79–89 (2002); and WO 9735999 A2). An expression cassette useful for the production of pHBA in plants consists of a gene encoding a fully active version of HCHL. Typically the expression cassette will comprise (1) the cloned HCHL coding sequence under the transcriptional control of 5' and 3' regulatory sequences and (2) a dominant selectable marker. The present expression cassette may also contain, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal. Optionally, the cassette may also comprise one or more introns in order to facilitate HCHL expression.

The HCHL gene encodes an enzyme that converts 1 mol of pHCACoA to 1 mol of acetylCoA and 1 mol of p-hydroxybenzaldehyde. p-hydroxybenzaldehyde is subsequently converted to pHBA through the action of endogenous plant enzymes that are present in the cytoplasm. The most well characterized HCHL gene has been isolated from *Pseudomonas fluorescence* (AN103) (GenBank® Accession No. Y13067.1). DNA sequence of an HCHL gene from *Pseudomonas putida* (Muheim and Learch, *App. Micro. Biotech.*, 51(4):456–461 (1999)) and the deduced amino acid sequence of the HCHL protein of this organism is set forth herein as SEQ ID NO:37 and SEQ ID NO:38, respectively. This gene has been isolated by the Applicants and also is useful for producing pHBA in transgenic plants.

Conversion of pHBA to Hydroquinone Using pHBA 1-Hydroxylase (Decarboxylating) from *Candida parapsilosis*

The present method uses a novel enzyme, pHBA 1-hydroxylase (decarboxylating), isolated from the ascomycetous yeast *Candida parapsilosis* (ATCC 7336) for enzymatic conversion of pHBA to hydroquinone (1,4-dihydroxybenzene). A six-step strategy for purifying this enzyme has previously been reported (Eppink et al., *J. Bacteriol.*, 179 (21): 6680–6687 (1997)). However, it is important to emphasize that the final preparation described in that disclosure, although highly enriched in pHBA 1-hydroxylase enzyme activity, consisted of a complex mixture of proteins. The predominant species in the partially purified enzyme preparation was a 52 kDa polypeptide as judged from a Coomassie-stained gel, and it was therefore assumed that this was the protein of interest. However, apart from its relative abundance in the final preparation, there was no compelling reason to conclude that the 52 kDa polypeptide was responsible for pHBA 1-hydroxylase enzyme activity. Nor was there any molecular characterization of the 52 kDa polypeptide that would allow one to clone the gene to test this hypothesis.

Figure 3:
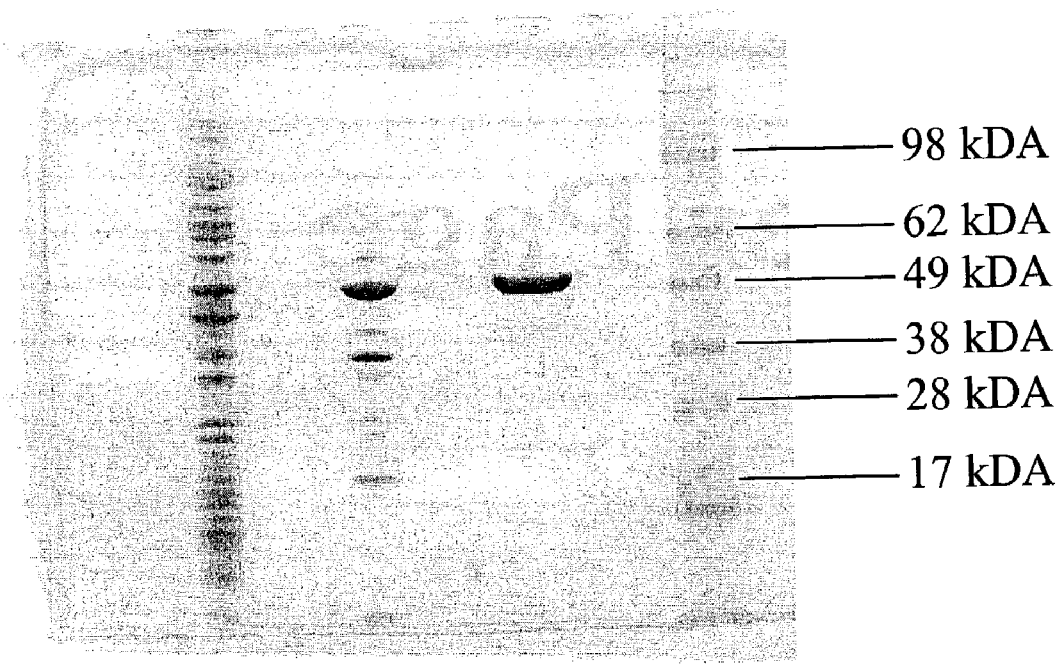
FIG. 3 shows a Coomassie blue-stained 14% SDS-PAGE gel of the purified protein that was used for enzyme characterization (lane C). The other lanes (A,B) show the recombinant pHBA 1-hydroxylase protein at various stages of the purification procedure that is described in Example 3.
Figure 4:
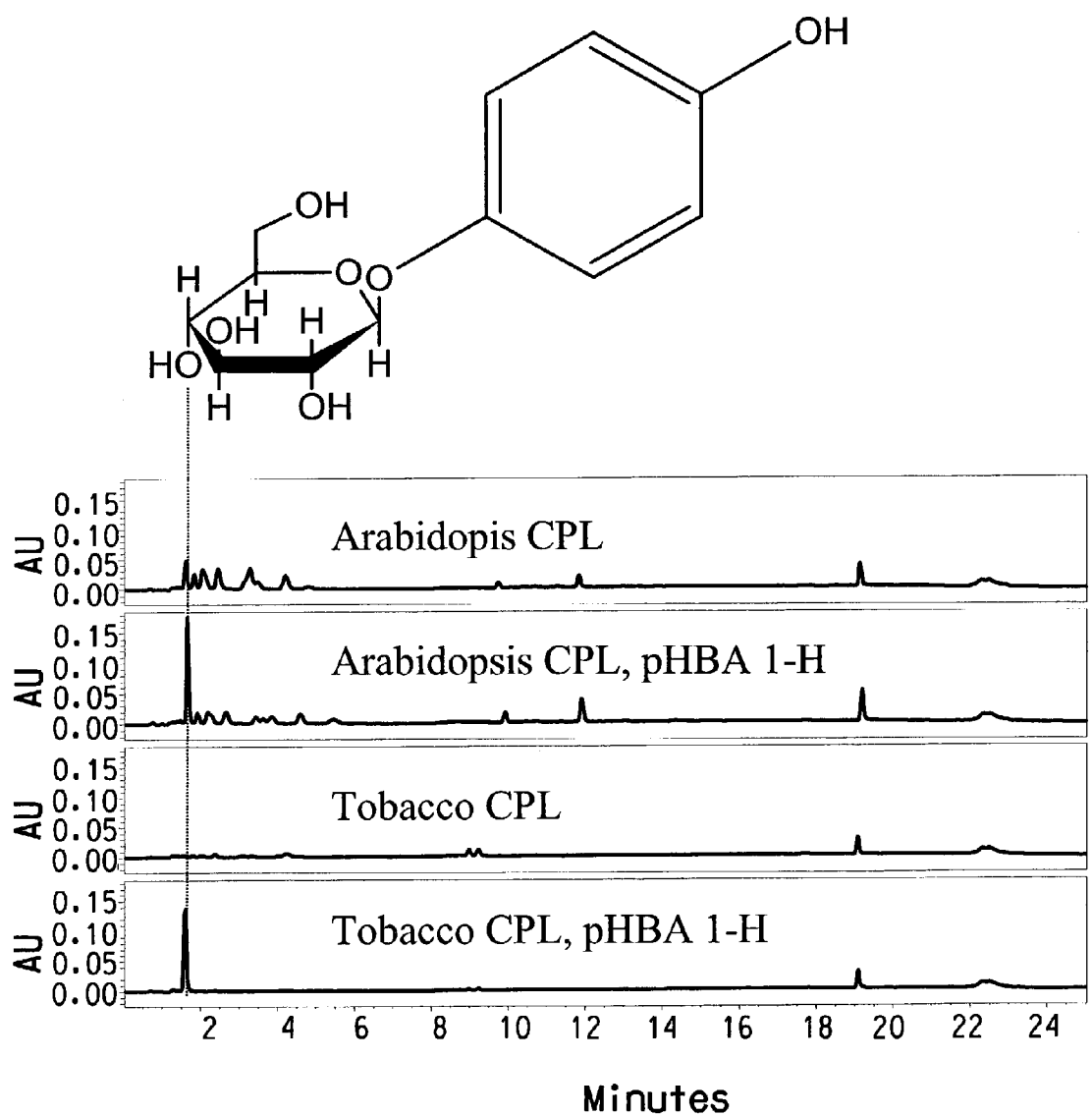
FIG. 4 shows the results of HPLC analysis of *arabidopsis* or tobacco plant tissue that expresses the CPL enzyme alone or in combination with the pHBA 1-hydroxylase enzyme.

In the present invention, Applicants have purified pHBA 1-hydroxylase from *Candida parapsilosis* to homogeneity and obtained sufficient amino acid sequence information to clone the gene. The entire DNA sequence of the full-length gene was determined (SEQ ID NO:22), and the latter was expressed in *E. coli*. To provide unequivocal proof that the cloned gene indeed codes for pHBA 1-hydroxylase, the resulting recombinant protein (SEQ ID NO:23) was purified to homogeneity and shown to catalyze the enzymatic conversion of pHBA to hydroquinone (Examples 1–3; FIGS. 3 and 4).

The closest match in GenBank® to the pHBA-1-hydroxylase amino acid sequence (SEQ ID NO:23) obtained using BLASTP analysis (default settings) identified a hypothetical protein from *Burkholderia fungorum* (GI: 22988817; 32% identity; 50% similarity; E-value=6e$^{-45}$). The low percent identity observed, in combination with the unknown function assigned to those sequences with the highest identity to SEQ ID NO:23, does not enable one to identify or assign function to the pHBA 1-hydroxylase gene. Moreover, SEQ ID NO:23 shares 30.081% identity and 39.295% similarity (GAP alignment, gap weight: 8 length weight: 2) with the 6-hydroxynicotinate 3-hydroxylase enzyme of *Pseudomonas* TN5 (Nakano et al., *Eur. J. Biochem.*, 260(1):120–126 (1999)) that catalyzes the oxidative decarboxylation of 6-hydroxynicotinate. This is a reaction that is closely related to the oxidative decarboxylation of pHBA catalyzed by the enzyme of SEQ ID NO 23. The low level of sequence similarity between this enzyme and SEQ ID NO:23 however would not have provided a means to isolate the pHBA 1-h hydroxylase enzyme using hybridization or PCR-based techniques of molecular biology.

The pHBA 1-hydroxylase is a flavoprotein monooxygenase. The enzyme requires the cofactor nicotinamide adenine dinucleotide (NADH) and a tightly bound cofactor, flavin adenine dinucleotide (FAD), for oxidative decarboxylation of pHBA or 4-hydroxybenzoate to hydroquinone as shown in Equation 1.

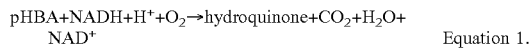

Equation 1.

Applicants have isolated the gene and expressed the functional enzyme in two different transgenic plants, tobacco and *arabidopsis* (Example 5). The ability to express the enzyme in transgenic plants capable of overproducing pHBA is illustrated. Analysis of the leaf tissue indicated that the transgenic plants expressing both a pHBA-production enzyme, such as CPL, and the pHBA 1-hydroxylase enzyme were able to produce hydroquinone as measured by the appearance of hydroquinone glucoside (arbutin) whereas hydroquinone glucoside was not detectable in plants lacking the pHBA 1-hydroxylase gene (Example 5; FIG. 4). The Glucoside production was measured as the majority of the hydroquinone produced was rapidly glucosylated by an endogenous UDP-glucosyltransferase. Applicants have conclusively demonstrated in two unrelated plant species that in order to achieve high levels of arbutin production in transgenic plants (through co-expression of a pHBA-production enzyme and pHBA 1-hydroxylase) it is not necessary to transform the plant with a hydroquinone-specific glucosyltransferase. Plants have an endogenous glucosyltransferase activity that efficiently mediates arbutin synthesis.

pHBA 1-Hydroxylase Expression Cassette

Arbutin production can be achieved by expression of a pHBA 1-hydroxylase enzyme of yeast origin in the cytoplasm of a pHBA-producing plant cell. pHBA can be expressed by suitable pHBA-production enzymes of plant, fungal, or microbial origin. Expression cassettes useful for converting pHBA to hydroquinone include a fully active version of the pHBA 1-hydroxylase enzyme. Typically, the expression cassette will comprise (1) the cloned pHBA 1-hydroxylase coding sequence under the transcriptional control of 5' and 3' regulatory sequences and (2) a dominant selectable marker as described in Example 5. The present expression cassette may also contain a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal. Optionally, the cassette may also comprise one or more introns in order to facilitate pHBA 1-hydroxylase expression. In a preferred embodiment, the cassette will additionally contain sequences allowing for efficient targeting of the pHBA 1-hydroxylase enzyme to the plastid. These components include a transit peptide as well as sequences encoding a portion of the transit peptide donor which contains a transit peptide cleavage site that is amenable to processing by the host plant cell chloroplast processing protease. In another preferred embodiment, the pHBA 1-hydroxylase gene is integrated directly into the chloroplast genome and expressed under the control of DNA sequence elements that allow for efficient translation and transcription in this organelle. This method of producing arbutin will be of particular use when the pHBA production enzyme (i.e., CPL) is also present in the plastid.

The pHBA 1-hydroxylase gene encodes an enzyme that converts 1 mol of pHBA to 1 mol of $CO_2$ and 1 mol of hydroquinone. The amino acid sequence of the pHBA 1-hydroxylase enzyme is disclosed as SEQ ID NO:23.

Plant Gene Expression

Promoters useful for driving the genes used in the present invention (CPL, HCHL, pHBA 1-Hydroxylase, and UDP-Glucosyltransferases) are numerous and well known in the art. Suitable promoters will be those that operate in plants and generally will be derived from the plant host in which the expression cassette resides. Any combination of any promoter and any terminator capable of inducing expression of the genes may be used in the present invention. Some suitable examples of promoters and terminators include the 35S promoter and those from nopaline synthase (nos), octopine synthase (ocs), and cauliflower mosaic virus (CaMV) genes. Such promoters, in operable linkage with the genetic sequences of the present invention, are capable of promoting expression of the present gene product. High-level plant promoters that may be used in this invention include the promoter of the small subunit (ss) of the ribulose-1,5-bisphosphate carboxylase from soybean (Berry-Lowe et al., *J. Mol. App. Gen.*, 1:483–498 (1982)), and the promoter of the chlorophyll a/b binding protein. These two promoters are known to be light-induced in plant cells (See, for example, *Genetic Engineering of Plants, an Agricultural Perspective*, A. Cashmore, Plenum, N.Y. (1983), pages 29–38; Coruzzi, G. et al., *J. Bio. Chem.*, 258:1399 (1983); and Dunsmuir et al., *J. Mol. App. Gen.*, 2:285 (1983)).

Where polypeptide expression is desired, it is generally desirable to include a polyadenylation region at the 3'-end of each gene's coding region in the present invention. The polyadenylation region can be derived from a variety of plant genes or from T-DNA. For example, the 3' end sequence to be added can be derived from the nopaline synthase or octopine synthase genes, or alternatively from another plant gene, or, less preferably, from any other eukaryotic gene.

An intron sequence can be added to the 5' untranslated region or the coding sequence of the partial coding sequence to increase the amount of the mature message that accumulates in the cytosol. Inducing a spliceable intron in the transcription unit of both plant and animal expression constructs has been shown to increase gene expression at both the mRNA and protein levels up to 1000-fold (Buchman and Berg, *Mol. Cell Biol.*, 8:4395–4405 (1988); Callis et al., *Genes Dev.*, 1:1183–1200 (1987)). Such intron enhancement of gene expression is typically greatest when placed near the 5' end of the transcription unit. Use of maize introns Adh1-S intron 1, 2, and 6, the Bronze-1 intron are known in the art.

(See generally, *The Maize Handbook*, Chapter 116, Freeling and Walbot, Eds., Springer, N.Y. (1994).)

It is useful to direct the CPL protein to the chloroplast and other plastids. Typically, this is achieved by introducing a chloroplast transit peptide that targets the expressed protein to plastids and also facilitates its translocation into the organelle. A number of chloroplast transit peptides are known and could be used in the present invention to direct CPL protein to the chloroplast including, but not limited to, those derived from *Pisum* (JP 1986224990; GenBank® Accession No. E00977), carrot (Luo et al., *Plant Mol. Biol.*, 33 (4):709–722 (1997); GenBank® Accession No. Z33383), *Nicotiana* (EP 0359617; GenBank® Accession No. A09029), *Oryza* (de Pater et al., *Plant Mol. Biol.*, 15 (3):399–406 (1990); GenBank® Accession No. X51911), as well as synthetic sequences (EP 0189707; U.S. Pat. No. 5,728,925; U.S. Pat. No. 5,717,084 (GenBank® Accession Nos. A10396 and A10398)). Preferred is the chloroplast transit peptide of the ribulose-1,5-bisphosphate carboxylase (Rubisco) small subunit precursor protein isolated from any plant. The Rubisco small subunit is well characterized from a variety of plants and the transit peptide from any of them will be suitable for use in the present invention. See, for example, disclosures related to *Physcomitrella* (GenBank® Accession No. AW599738); *Lotus* (GenBank® Accession No. AW428760); *Citrullus* (GenBank Accession No. AI563240); *Nicotiana* (Appleby et al., *Heredity*, 79(6): 557–563 (1997)); alfalfa (Khoudi et al., *Gene*, 197(1/2): 343–351 (1997)); potato and tomato (Fritz et al., *Gene*, 137(2):271–4 (1993)); wheat (Galili et al., *Theor. Appl. Genet.*, 81(1):98–104 (1991)); and rice (Xie et al., *Sci. Sin., Ser.* B (Engl. Ed.), 30(7):706–19 (1987)). For example, transit peptides may be derived from the Rubisco small subunit isolated from plants including, but not limited to, soybean, rapeseed, sunflower, cotton, corn, tobacco, alfalfa, wheat, barley, oats, sorghum, rice, *Arabidopsis*, sugar beet, sugar cane, canola, millet, beans, peas, rye, flax, and forage grasses. Preferred for use in the present invention is the tomato Rubisco small subunit precursor protein.

Chloroplast targeting sequences not only target the desired protein to the chloroplast but also facilitate its translocation into the organelle. This is accompanied by the cleaving of the transit peptide from the mature polypeptide or protein at the appropriate transit peptide cleavage site by a chloroplast processing protease, native to the chloroplast. Accordingly, the chloroplast targeting sequence comprises a suitable cleavage site for the correct processing of the pre-protein to an active mature polypeptide contained within the chloroplast. Preferred in the present invention is the chloroplast targeting sequence of the tomato Rubisco small subunit precursor protein having a cleavage site between the naturally occurring Cys and Met residues that separate the transit peptide from the mature polypeptide.

The functional CPL expression cassette is used to transform a suitable plant host to express CPL and produce pHBA in the chloroplast. Virtually any plant host that is capable of supporting the expression of the genes in the present invention will be suitable; however, crop plants are preferred for their ease of harvesting and large biomass. Suitable plant hosts include, but are not limited to, both monocots and dicots such as soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), *Arabidopsis*, sugar beet, sugar cane, canola, millet, beans, peas, rye, flax, and forage grasses. Preferred plant hosts are tobacco, *Arabidopsis thaliana*, sugarcane, and sugar beet.

Plant Transformation

A variety of techniques are available and known to those skilled in the art to introduce constructs into a plant cell host. These techniques include transformation with DNA employing *A. tumefaciens* or *A. rhizogenes* as the transforming agent, electroporation, and particle acceleration (EP 295959 and EP 138341). One suitable method involves the use of binary type vectors of Ti and Ri plasmids of *Agrobacterium* spp. Ti-derived vectors transform a wide variety of higher plants including monocotyledonous and dicotyledonous plants such as soybean, cotton, rape, tobacco, and rice (Pacciotti et al., *Bio/Technology*, 3:241 (1985); Byrne et al., *Plant Cell, Tissue and Organ Culture*, 8:3 (1987); Sukhapinda et al., *Plant Mol. Biol.*, 8:209–216 (1987); Lorz et al., *Mol. Gen. Genet.*, 199:178 (1985); Potrykus et al., *Mol. Gen. Genet.*, 199:183 (1985); Park et al., *J. Plant Biol.*, 38(4): 365–71 (1995); and Hiei et al., *Plant J.*, 6:271–282 (1994)). The use of T-DNA to transform plant cells has received extensive study and is amply described (EP 120516; Hoekema, In: *The Binary Plant Vector System*, Offset-drukkerij Kanters B. V.; Alblasserdam (1985), Chapter V; Knauf et al., *Genetic Analysis of Host Range Expression by Agrobacterium* In: *Molecular Genetics of the Bacteria-Plant Interaction*, Puhler, A. ed., Springer-Verlag, New York, 1983, p. 245; and An et al., *EMBO J.*, 4:277–284 (1985)). For introduction into plants, the chimeric genes can be inserted into binary vectors as described in the examples.

Other transformation methods are known to those skilled in the art. Examples include direct uptake of foreign DNA constructs (EP 295959), techniques of electroporation (Fromm et al., *Nature* (London), 319:791 (1986)), and high-velocity ballistic bombardment with metal particles coated with the nucleic acid constructs (Kline et al, *Nature* (London), 327:70 (1987); and U.S. Pat. No. 4,945,050). Once transformed, the cells can be regenerated by those skilled in the art. Of particular relevance are the recently described methods to transform foreign genes into commercially important crops, such as rapeseed (De Block et al, *Plant Physiol.*, 91:694–701 (1989)), sunflower (Everett et al., *Bio/Technology*, 5:1201 (1987)), soybean (McCabe et al, *Bio/Technology*, 6:923 (1988); Hinchee et al., *Bio/Technology* 6:915 (1988); Chee et al., *Plant Physiol.* 91:1212–1218 (1989); Christou et al., *Proc. Natl. Acad. Sci. USA*, 86:7500–7504 (1989); EP 301749), rice (Hiei et al., supra), and corn (Gordon-Kamm et al., *Plant Cell*, 2:603–618 (1990); and Fromm et al., *Biotechnology*, 8:833–839 (1990)).

Transgenic plant cells are placed in an appropriate medium to select for the transgenic cells that are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will select for transformed cells as compared to cells lacking the DNA that has been introduced. Components of DNA constructs including transcription cassettes may be prepared from sequences which are native (endogenous) or foreign (exogenous) to the host. Heterologous constructs will contain at least one region that is not native to the gene from which the transcription-initiation-region is derived. To confirm the presence of the transgenes in transgenic cells and plants, a Southern blot analysis can be performed using methods known to those skilled in the art.

CPL Translocation into the Chloroplast and Subsequent Processing

The present invention manipulates a chloroplast targeting sequence to effect the translocation of the CPL gene product into chloroplasts with sufficient enzyme activity to yield suitable amounts of pHBA substrate. Applicants have discovered that including not only a transit peptide, but also a naturally occurring chloroplast cleavage site and a small portion of the transit peptide donor's mature N-terminus improves chloroplast uptake and processing of the foreign protein to obtain higher rates of conversion of chorismate to pHBA. Following uptake into the organelle, however, the transit peptide is proteolytically removed by a chloroplast-processing enzyme to yield a CPL variant that has a small polypeptide extension attached at its N-terminus. Unexpectedly, these additional amino acid resides do not interfere with CPL enzyme activity. Transformed plants expressing the instant chimeric protein accumulate significantly greater amounts of pHBA derivatives than have previously been reported. With regard to pHBA production, the need for this type of specificity not previously appreciated in the art.

The only reported instance of an attempt to express CPL in chloroplasts of living plants is recited in Siebert et al. (*Plant Physiol.* 112:811–819 (1996)). However, the instant chimeric protein (e.g., TP-CPL; SEQ ID NO:34) differs from the chloroplast-targeted version of *E. coli* CPL (e.g., TP-UbiC) recited in Siebert et al. (supra, 1996) in a number of important aspects as described in U.S. Ser. No. 09/855,341. For example, the instant chimera includes a chloroplast-targeting sequence having a well-defined cleavage site for the efficient removal of the transit peptide. Additionally, removal of the transit peptide at this specific site results in the addition of 5 extra amino acids at the N-terminal region of the mature CPL polypeptide. In contrast, TP-UbiC recited in Siebert et al. (supra 1996) lacks a well-defined cleavage site and contains a stretch of nine amino acids inserted between the putative transit peptide cleavage site and the initiator methionine residue of *E. coli* CPL.

The TP-CPL protein consists of the chloroplast transit peptide of the tomato Rubisco small subunit precursor plus the first four amino acid residues of "mature" Rubisco, fused to the initiator Met residue of *E. coli* CPL. Thus, TP-CPL contains not only the entire transit peptide, but also the highly conserved cleavage site where transit peptide removal would normally occur (e.g., between the Cys and Met residues as indicated by the arrow). Assuming that TP-CPL is also cleaved at this position in the chloroplast, the resulting protein would be a CPL variant with five additional amino acid residues at its N-terminus. The predicted chloroplast cleavage product of TP-CPL was expressed in *E. coli* and shown it to be fully functional with regard to enzyme activity (SEQ ID NO:34).

Production of Arbutin in Microorganisms from pHBA pHBA has been produced in microbial systems. For example, JP 06078780 teaches pHBA production by culturing benzoic acid in the presence of microorganisms (preferably *Aspergillus*) that oxidize benzoic acid to pHBA. Additionally, strains of *Enterobacter* that convert p-cresol to pHBA have been isolated from soil (JP 05328981). Furthermore, JP 05336980 and JP 05336979 disclose isolated strains of *Pseudomonas putida* that produce pHBA from p-cresol. Similarly, commonly owned WO 9856920 teaches a method for the production of pHBA from toluene using a *Pseudomonas mendocina* mutant lacking the ability to express para-hydroxybenzoate hydroxylase (pHBH). Finally, U.S. Pat. No. 6,030,819 teaches the production of pHBA in genetically engineered *E. coli* expressing the chorismate pyruvate lyase (CPL) gene.

Biotransformation methods used to produce arbutin from hydroquinone have been described previously (Arend et al., *Phytochemistry*, 53:187–193 (2000); Arend et al., *Biotech. Bioeng.*, 76(2):126–131 (2001); Hefner et al., *Bioorg. Med. Chem.*, 10:1731–1741 (2002); and JP 07224083A. These methods generally involve exogenously supplying hydroquinone to plant cell cultures, seeds, or seedlings expressing suitable glucosyltransferases. A similar method by Arend et al. (*Biotech. Bioeng.*, 76(2):126–131 (2001)) converts hydroquinone (an expensive and toxic compound) and UDP-glucose into arbutin using a recombinant *E. coli* strain expressing a UDP-glucosyltransferase. These biotransformation methods rely upon the use of exogenously supplied hydroquinone. In contrast, the present invention provides methods to produce arbutin from a cheap, non-toxic, fermentable carbon source such as glucose.

The molecular identification and isolation of the pHBA 1-hydroxylase gene described by Applicants also enables arbutin production in microbial systems such as *E. coli* (described in detail in Examples 7 and 8). The pHBA 1-hydroxylase gene is expressed in *E. coli* cells in combination with a chorismate pyruvate-lyase gene and a suitable glucosyltransferase gene (Examples 6 and 8). Expressing these three enzymes in *E. coli* provides a route to arbutin from a cheap, fermentable carbon source, such as glucose, by creating a three-step pathway from chorismate to arbutin (FIG. 1). Those skilled in the art will recognize that all cofactors, coenzymes and co-substrates required for this pathway such as FAD, NADH, $O_2$, and UDP-glucose (UDPG) are present in the *E. coli* cytoplasm. Moreover *E. coli* strains with elevated levels of chorismate resulting from increased flux of carbon into the shikimate pathway have been disclosed (Berry et al., *Trends Biotech.*, 14(7):250–256 (1996); Bongaerts et al., *Metabolic Engineering*, 3(4):289–300 (2001); Tatarko and Romeo, *Current Microbiology*, 43(1):26–32 (2001); U.S. Pat. No. 6,210,937; US 5776736; and WO 73484 A1) and can be used to produce arbutin from glucose using the molecular tools described below.

UDP-Glucosyltransferases

Arbutin is a more valuable product than hydroquinone. Therefore, it is preferable to combine CPL and pHBA 1-hydroxylase with a suitable glucosyltransferase to produce arbutin instead of producing hydroquinone in microbes such as *E. coli* through co-expression of CPL and pHBA 1-hydroxylase. Producing hydroquinone glucoside results in the release of the molecule from the cell into the growth medium where it can easily be harvested and purified (Arend et al., *Biotech. and Bioeng.*, 76(2):126–131 (2001)). Producing arbutin in *E. coli* requires a glucosyltransferase gene encoding an enzyme that efficiently glucosylates hydroquinone. An enzyme with this property has been disclosed (Arend et al., *Phytochemistry*, 53:187–193 (2000) and WO 0107631 A2).

Figure 6:
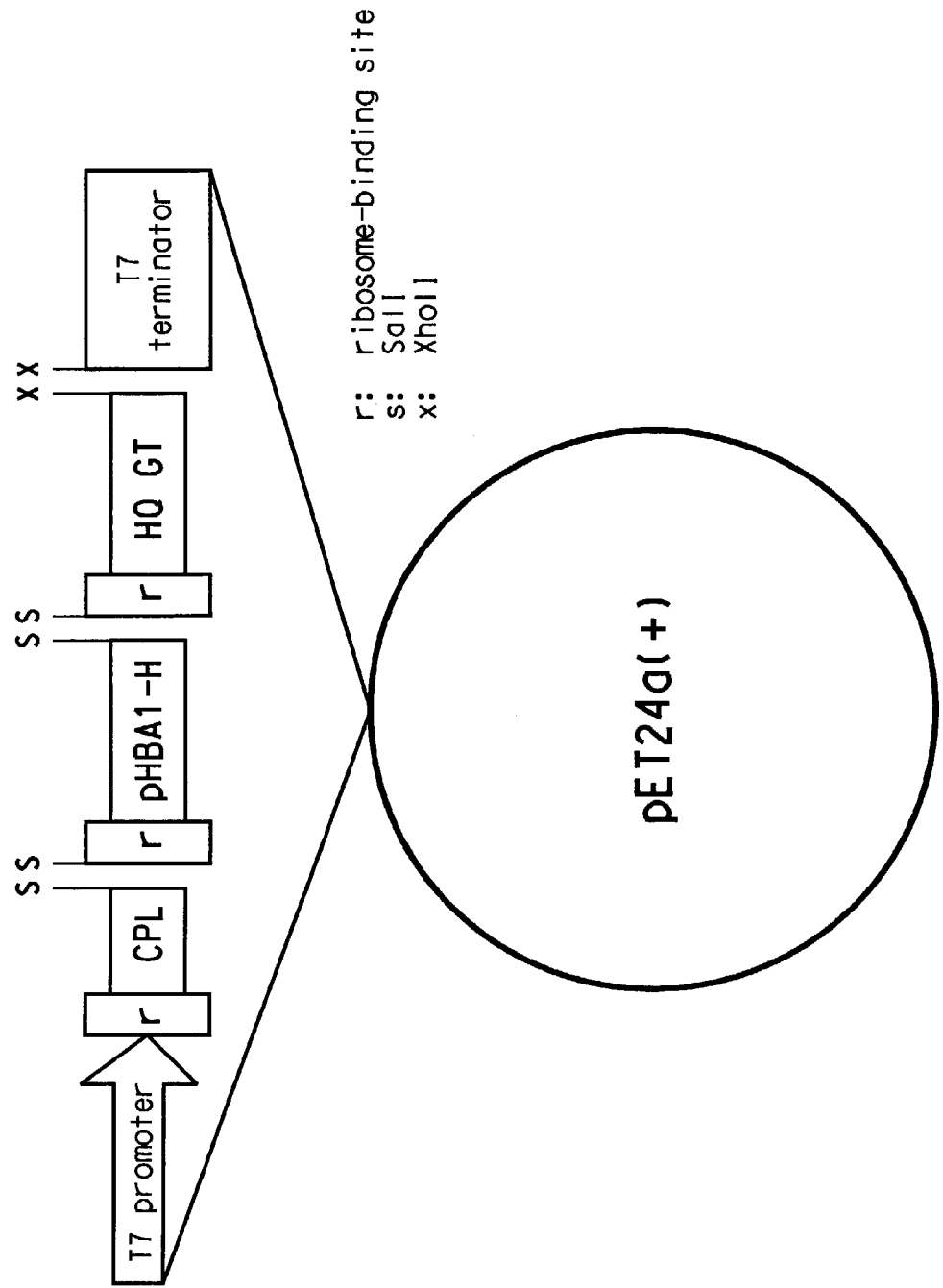
FIG. 6 shows the cloning strategy used to generate a plasmid vector carrying a synthetic operon that allows expression of chorismate pyruvate-lyase, pHBA 1-hydroxylase, and hydroquinone glucosyltransferase under the control of the T7 promoter. Co-expression of these three genes enables arbutin production in microbes such as *E. coli*.

Applicants have characterized an enzyme from *Arabidopsis thaliana* that shares 62% identity at the amino acid sequence level to the arbutin synthase of *Rauwolfia serpentina* (Gi:28380078; 62% identity; 78% similarity; E value=$e^{-174}$). Applicants disclose the unexpected observation of an extremely high catalytic efficiency (Km 0.3 µM, Kcat 42/sec) of the *arabidopsis* enzyme with hydroquinone (Example 6). A preferred embodiment of the invention is a microbial cell transformed with a plasmid carrying a synthetic operon allowing expression of CPL, pHBA 1-hydroxylase, and *arabidopsis* hydroquinone glucosyltransferase (FIG. 6). Typically, the expression cassette will comprise the three coding sequences and a ribosome binding site in sequential order under the control of a suitable promoter. In addition, a promoter regulatory region may be used to confer inducible, constitutive, or environmentally regulated expression. It will contain a transcription initiation start site, a ribosome binding site, and a transcription termination site. In another preferred embodiment, the three genes are introduced on separate plasmids that harbor origins of replication that can co-exist in *E. coli*. The expression cassette on each plasmid will be comprised of the CPL or pHBA 1-hydroxylase gene or *arabidopsis* glucosyltransferase gene and suitable promoter-regulatory regions that confer inducible, constitutive, or environmentally-regulated expression. Moreover, each plasmid will contain a transcription initiation start site, a ribosome binding site, and a transcription termination site.

In vitro methods can be used to oxidatively decarboxylate pHBA to form hydroquinone and for subsequent conversion to hydroquinone glucoside (arbutin) using enzyme catalysts having 1) pHBA 1-hydroxylase activity and 2) UDP-glucosyltransferase activity in the form of whole microbial cells, permeabilized microbial cells, one or more components of a microbial cell extract, partially purified enzyme(s), or purified enzymes(s). Preferably, the form of the enzyme catalysts is whole microbial cells or partially purified or purified enzymes. The different forms of enzyme catalysts can be immobilized on or in a soluble or insoluble support.

Microbial Expression

The genes and gene products of the present invention may be introduced into microbial host cells. Preferred host cells for expression of the instant genes and nucleic acid molecules are microbial hosts that can be found broadly within the fungal or bacterial families and which grow over a wide range of temperature, pH values, and solvent tolerances. Functional genes are expressed irrespective of carbon feedstock used to generate cellular biomass. Large-scale microbial growth and functional gene expression may utilize a wide range of simple or complex carbohydrates, organic acids and alcohols, and saturated hydrocarbons such as methane or carbon dioxide in the case of photosynthetic or chemoautotrophic hosts. However, the functional genes may be regulated by specific growth conditions including the form and amount of nitrogen, phosphorous, sulfur, oxygen, carbon or any trace micronutrient (including small inorganic ions). In addition, the regulation of functional genes may be achieved by the presence or absence of specific regulatory molecules that are added to the culture and are not typically considered nutrient or energy sources. Growth rate may also be an important regulatory factor in gene expression. Examples of suitable host strains include, but are not limited to, fungal or yeast species such as *Aspergillus, Trichoderma, Saccharomyces, Pichia, Candida, Hansenula*, or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium, Klebsiella, Burkholderia, Sphingomonas, Paracoccus, Pandoraea, Delftia*, and *Comamonas*.

Microbial expression systems and expression vectors containing regulatory sequences that direct high level expression of foreign proteins are well known to those skilled in the art. Any of these could be used to construct chimeric genes for production of the any of the gene products of the instant sequences. These chimeric genes could then be introduced into appropriate microorganisms via transformation to provide high level expression of the enzymes.

Vectors or cassettes useful for transforming suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene that harbors transcriptional initiation controls and a region 3' of the DNA fragment that controls transcriptional termination. It is most preferred when both control regions are derived from genes homologous to the transformed host cell, although it is understood that such control regions need not be derived from the genes native to the specific species chosen as a production host.

Initiation control regions or promoters used to drive expression of the instant ORF's in the desired host cells are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. A termination site may be unnecessary; however, it is most preferred if included.

Once a suitable expression cassette is constructed comprising one or more of the genes of the present invention, it may be used to transform a suitable host. The host can then be used to preferentially catalyze the formation of the hydroquinone or hydroquinone glucoside.

Culturing Systems

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as carbon dioxide. Batch and Fed-Batch culturing methods are common and well known in the art and examples may be found in Thomas D. Brock, In *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227 (1992), herein incorporated by reference.

Commercial production may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Enzyme Kinetics

Catalytic efficiency is usually expressed as Kcat/Km. Important parameters of enzyme-catalyzed reactions include:

1) turnover number (Kcat), a unit for catalytic power of a monomeric enzymatic catalyst expressed as μmol of product formed per second per μmol of enzyme, and
2) Km, a unit for affinity of the enzyme to a particular substrate, expressed as the substrate concentration at which 50% of maximum velocity is achieved.

A preferred embodiment of this invention is a pHBA 1-hydroxylase enzyme from *Candida parapsilosis* that has a Km of <1 μM and a Kcat of at least ~9.5/sec for pHBA and a glucosyltransferase enzyme from *Arabidopsis thaliana* (UGT72B1) that has a Km of <1 μM and a Kcat of at least 42/sec for hydroquinone.

EXAMPLES

The present invention is further defined in the following Examples. It should be understood that these Examples, while indicating preferred embodiments of the invention, are given by way of illustration only.

General Methods

Standard recombinant DNA and molecular cloning techniques used in the Examples are well known in the art and are described by Maniatis, Silhavy, and Ausubel (supra).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg, and G. Briggs Phillips, eds), American Society for Microbiology, Washington, D.C. (1994)) or Brock (supra). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

Manipulations of genetic sequences were accomplished using the suite of programs available from the Genetics Computer Group Inc. (Wisconsin Package Version 9.0, Genetics Computer Group (GCG), Madison, Wis.). The GCG program "Pileup" used the gap creation default value of 12, and the gap extension default value of 4. The CGC "Gap" or "Bestfit" programs used the default gap creation penalty of 50 and the default gap extension penalty of 3. In any case where GCG program parameters were not prompted for, in these or any other GCG program, default values were used.

The meaning of abbreviations is as follows: "h" means hour(s), "min" means minute(s), "sec" means second(s), "d" means day(s), "mL" means milliliters, "L" means liters, "μL" means microliters, "g" means grams, "mg" means milligrams, "μg" means micrograms, "M" means molar, "mM" means millimolar, and "μM" mean micromolar.

Example 1

Growth of *Candida parapsilosis* ATCC 7336 and Analysis of pHBA 1-Hydroxylase Activity A yeast culture was established on YM media plates (formulated per liter; 3 g yeast extract, 3 g malt extract, 5 g peptone, 10 g glucose, and 15 g agar) from the lyophilized ATCC culture stock. The yeast cells were grown at 30° C. under aseptic conditions in liquid media or on agar plates containing double concentrated Reader's medium (formulated per liter; 3 g $(NH_4)_2SO_4$, 1.4 g $MgSO_4 \cdot 7H_2O$, 1 g NaCl, 0.4 g $CaCl_2 \cdot 2H_2O$, 2 g $KH_2PO_4$, 0.2 g $K_2HPO_4$, 0.4 mg $H_3BO_3$, 0.4 mg $MnCl_2$, 0.4 mg $Na_2MoO_4$, 0.4 mg $ZnSO_4$, 0.2 mg KI, 0.2 mg $CoCl_2$, 0.08 mg $CuSO_4$, 0.1 mg $FeCl_3$, 0.4 mg panthothenate, 0.4 mg nicotinic acid, 0.4 mg pyridoxine, 0.4 mg para-aminobenzoic acid, 0.8 mg inositol, and 0.0025 mg biotin). The carbon source was 100 mM glucose or 1 mM, 10 mM, or 100 mM pHBA. Applicant determined that *Candida parapsilosis* (ATCC 7336) was able to grow on pHBA as the sole carbon source. Best growth on solidified media was observed at 10 mM pHBA. Cultures (500 mL) of concentrated Reader's medium containing 100 mM glucose or pHBA at the concentration described below were inoculated with a single colony of yeast cells obtained from a 10 mM pHBA plate.

Growth of the culture containing pHBA as sole carbon source was conducted as follows. Concentrated Reader's medium (250 mL) containing 1 mM pHBA was inoculated and allowed to grow for 24 h at 30° C. The culture was then adjusted to a final pHBA concentration of mM pHBA with concentrated Reader's medium containing 50 mM pHBA. After another 24 h, pHBA concentration was adjusted to a final concentration of 10 mM. Cells were grown for another 24 h followed by another addition of pHBA corresponding to a final concentration of 10 mM. After another 24 h, cells were harvested by centrifugation (5000×g, 10 min). Cells grown in the presence of glucose or pHBA as sole carbon source were resuspended in 10 mL of 20 mM Tris/$H_2SO_4$ (pH 7.8), 0.5 mM DTT, 0.5 mM EDTA, 0.5 mM PMSF, and 10 μM FAD. Cell-free extracts were prepared by two passes through a French press followed by centrifugation at 30000× g, 20 min, at 4° C. Protein concentrations were determined according using the Bradford reagent (Bio-Rad, Hercules, Calif.).

pHBA 1-Hydroxylase activity was measured as follows. Cell-free extract corresponding to 200 μg of total protein was incubated at 37° C. in a final volume of 100 μl in the presence of 50 mM $KPO_4$ (pH 7.6), 1 mM pHBA, and 2 mM NADH. The reaction was stopped by adding an equal volume of methanol (MeOH) containing 12% (v/v) acetic acid. The reaction products were clarified by centrifugation (13000×g, 10 min) and analyzed by HPLC as follows. Reaction products (10 μl) were injected onto a Nova Pak C18 column (3.9×150 mm, 60 Å, 4 μm) (Waters, Mass., USA). The column was developed at a flow-rate of 1 mL/min under the following conditions: Solvent A ($H_2O$/1.5% $HPO_4$), Solvent B (48% Acetonitrile/$H_2O$/1.5% $HPO_4$); 0–5 min 0% B, 5–20 min 0–100% B (linear gradient), 20–21 min 100–0% B, 21–25 min 0% B. Absorption for pHBA was detected at 254 nm and for hydroquinone at 288 nm. Compounds corresponding to pHBA and hydroquinone were identified in the enzyme reaction products based on retention time and UV absorption spectra that were indistinguishable from those of the authentic pHBA and hydroquinone standards. HPLC analysis revealed that protein extracts of cells grown on pHBA as the sole carbon source contained an enzyme activity that was able to convert pHBA to hydroquinone in the presence of NADH. Hydroquinone concentration in the enzyme assay was 260 μM after 20 min indicating that 26% of the initial pHBA had been converted to hydroquinone. No hydroquinone formation was detected when protein extracts of cells grown in the presence of glucose were used under identical conditions.

Measurement of pHBA 1-Hydroxylase Activity

Specific pHBA 1-hydroxylase activity was measured as follows: 100 μg of *Candida parapsilosis* protein (ATCC 7336) was added to 500 μl of reaction medium containing 0.1 mM pHBA, 0.2 mM NADH, 10 μM FAD, and 50 mM $KPO_4$ (pH 7.6). The rate of NADH oxidation was measured by monitoring absorption at 340 nm. NADH oxidase activity in the *Candida parapsilosis* protein extract that is unrelated to pHBA 1-hydroxylase activity was measured under identical conditions in the absence of pHBA. Specific pHBA 1-hydroxylase activity was calculated using 6250 $M^{-1}$ as the absorption coefficient for NADH and was found to be 0.14 U/mg protein for *Candida parapsilosis* cells grown on pHBA as the sole carbon source. Applicants have shown that in *Candida parapsilosis* (ATCC 7336) pHBA 1-hydroxylase expression is highly induced when cells are grown on pHBA as the sole carbon source.

Example 2

Purification of the pHBA 1-hydroxylase Enzyme, Determination of Partial Amino Acid Sequence of the Purified Protein, and Cloning and Sequencing of a cDNA Encoding the pHBA 1-hydroxylase Protein Two 5 L flasks, each containing 1 L of double-concentrated Reader's medium (Karasevich and Ivoilov, *Mikrobiologiya*, 46(5):846–56 (1977)) containing 1 mM of pHBA, were inoculated with colonies of *Candida parapsilosis* (ATCC 7336) grown on plates with 10 mM pHBA as the sole carbon source. Each culture received successive additions of 100, 300, and 600 mL of double concentrated Reader's medium containing 50 mM of pHBA at 24 h intervals. Cells were harvested 24 h after the last addition of pHBA. Thus, 4 L of yeast culture were grown under conditions where the pHBA concentration was gradually increased from 1 mM to a final concentration of 26 mM during the 96 h time interval.

Cells were harvested by centrifugation (5000×g 10 min) and resuspended in 35 mL of 20 mM Tris/$H_2SO_4$ (pH 7.8), 0.5 mM DTT, 0.5 mM EDTA, 0.5 mM PMSF, and 10 μM FAD. The cell suspension was passed twice through a French press and cleared by centrifugation (30000×g, 20 min, at 4° C.). Glycerol was added to a final concentration of 7% (v/v). This extract was stored at −80° C. without loss of pHBA 1-hydroxylase enzyme activity. The protein concentration was 16.25 mg/mL and the specific activity was 0.129 U/mg protein. The culture provided a protein extract of 40 mL representing a total of 650 mg of protein containing 84 U of pHBA 1-hydroxylase activity.

Twenty milliliters of the crude extract was buffer-exchanged in 2.5 mL aliquots on PD-10 columns (Pharmacia Biotech, Milwaukee, Wis.) into 10 mM Tris/$H_2SO_4$ (pH 7.8), 0.5 mM DTT, 0.5 mM EDTA, and 10 μM FAD; the final volume after this step was 28 mL and 85% of the original enzyme activity was recovered. Fourteen milliliters of this material was applied to a MonoQ HR 10/10 column (Amersham Biosciences, Piscataway, N.J.) that was pre-equilibrated at 25° C. with Buffer Q (10 mM Tris/$H_2SO_4$ (pH 7.8), 0.5 mM DTT, 0.5 mM EDTA, and 10 μM FAD). The column was developed at 4 mL/min with Buffer Q for the first 12 min. This was followed by a linear gradient (80 mL) of 0–100 mM $Na_2SO_4$ (in Buffer Q). Fractions (8 mL) were collected from the start of the gradient and kept on ice for subsequent determination of enzyme activity. The column was then extensively washed with 1 M $Na_2SO_4$ (in Buffer Q) and initial conditions were reestablished.

The remaining 14 mL of the PD-10 eluent was processed in an identical manner, and fractions from both MonoQ columns were assayed for pHBA 1-hydroxylase activity using the spectrophotometric assay. The most active fractions were pooled (fraction #3 from the first column and fractions #3 and #4 from the second column) and supplemented with 50 mM $Na_2SO_4$ and 7% (v/v) glycerol; 26 U of pHBA 1-hydroxylase activity was recovered. The pooled fractions were concentrated to 2.3 mL using a Centriprep-10 (Millipore Corp., Bedford, Mass.) and passed through a 0.2 μm Acrodisc filter (Gelman-Pall Life Sciences: Cat. No. 4192). Two milliliters of this material was then fractionated on a 21×600 mM TSK-Gel® G3000SW gel filtration column (Tosoh Biosep LLC., Montgomeryville, Pa.). The column was developed at 4 mL/min with 100 mM potassium phosphate (pH 7.7), 0.5 mM EDTA, 0.5 mM DTT, and 15 μM FAD (25° C.) and 2 mL fractions were collected. The latter were assayed for pHBA 1-hydroxylase activity using the spectrophotometric assay and the four most active fractions were pooled. The recovery of enzyme activity from the column was 55% (12.5 U).

The pooled fractions were concentrated to 5 mL and buffer-exchanged into 10 mM sodium phosphate (pH 6.8), 10 μM $CaCl_2$, 1 mM DTT, and 20 μM FAD (Buffer W) using two PD-10 columns (Pharmacia). The entire 7-mL sample was then applied to a 7.8×100 mM Bio-Gel HPHT hydroxylapatite column (Bio-Rad, Hercules, Calif.) which was pre-equilibrated a 25° C. with Buffer W. The column was developed at 0.5 mL/min with Buffer W for 14 min, and this was followed by a linear gradient (30 mL) of 10–350 mM sodium phosphate (pH 6.8) in Buffer W; 1 mL fractions were collected. Based on the spectrophotometric assay, pHBA 1-hydroxylase eluted between 40–50 min, and the two fractions with the most activity were pooled. The pooled material contained 4.9 U of enzyme activity. The sample was then supplemented with 50 mM NaSO$_4$ and 7% (v/v) glycerol and stored at –80° C. for further manipulation.

Visual inspection of the hydroxylapatite pool on a Coomassie-stained gel revealed the presence of two bands that had apparent molecular masses of 49 and 52 kDa. To determine which of these polypeptides was pHBA 1-hydroxylase, a 1 mL aliquot of the hydroxylapatite pool was buffer-exchanged into Buffer Z (10 mM Tris/H$_2$SO$_4$ (pH 7.5), 1 mM DTT, and 0.5 mM EDTA) using a PD-10 column. The final volume was 3.5 mL and the sample contained 1.28 U of enzyme activity based on the spectrophotometric assay. The entire sample was then applied to a MonoQ HR 5/5 column (Amersham Biosciences, Piscataway, N.J.) that was pre-equilibrated at 25° C. with Buffer Z. The column was developed at 1 mL/min with Buffer Z for the first 5 min followed by a linear gradient (20 mL) of 0–100 mM Na$_2$SO$_4$ (in Buffer Z).

Two major 280 nm-absorbing peaks emerged from the column and both were collected. The larger peak, which eluted between 8.1–8.9 min, only contained the 52 kDa polypeptide as judged from a Coomassie-stained gel. This peak also contained 1.14 U of pHBA 1-hydroxylase activity, which is ~90% of the total activity that was applied to the MonoQ column. The smaller peak, which eluted between 8.9 and 10.2 min, contained the 48 kDa polypeptide and numerous minor contaminants. Importantly, however, this peak only contained 0.02 U of pHBA 1-hydroxylase activity, which is less than 2% of the original enzyme activity applied to the column. Based on these observations it was concluded that the 52 kDa polypeptide in the first peak of the MonoQ column was the pHBA 1-hydroxylase of *Candida parapsilosis* (ATCC 7336). The column fraction was supplemented with 100 mM Na$_2$SO$_4$ and 7% (v/v) glycerol and stored at –80° C. The final volume was 1.0 mL and the sample contained approximately 50 µg of the purified enzyme. As described below, an aliquot of this material was used for trypsin digestion to generate peptide fragments for amino acid sequence analysis. Based on the specific activities of the crude extract starting material (0.129 U/mg of protein) and the final preparation of purified protein (22.8 U/mg), pHBA 1-hydroxylase was purified approximately 180-fold using the above procedure.

Amino Acid Sequence Determination

To determine the N-terminal amino acid sequence of intact pHBA 1-hydroxylase, 800 µl of the hydroxylapatite pool containing the partially purified protein was taken to dryness and resuspended in SDS sample buffer. The sample was applied to a pre-cast Novex SDS-PAGE gel (Invitrogen, USA) and subjected to electrophoresis according to manufacturer instructions. The separated proteins were electroblotted onto a polyvinylidene difluoride membrane (Novex, Calif., USA), which was subsequently washed with deionized water and stained with 0.1% Coomassie Blue G250 (Invitrogen, USA). The stained 52 kDa band corresponding to pHBA 1-hydroxylase was subjected to automated Edman degradation using a Beckman-Coulter LF3000 gas phase protein sequencer. The following amino acid sequence was obtained from the first 24 cycles of Edman degradation:

Ala-Val-Gln-Ala-Pro-Ser-Lys-Thr-Tyr- SEQ ID NO:1
Gly-Phe-Gln-Lys-Ala-Pro-Ile-Gln-Leu-
Thr-Phe-Val-Val-Val-Gly

Additional amino acid sequence information was obtained from proteolytic digestion of the purified protein, followed by HPLC-separation and Edman degradation of the resulting peptide fragments. Purified pHBA 1-hydroxylase was concentrated to approximately 0.33 mg of protein per milliliter in a Centricon-10 (Millipore Corp., Bedford, Mass.). The trypsin stock solution was prepared right before the experiment and kept on ice until use. The latter consisted of 20 µg of TPCK-treated, Sequencing Grade Trypsin (Promega) that was dissolved in 266 µl of glacial acetic acid. The trypsin digestion reaction was assembled on ice in a 1.5 mL polypropylene microfuge tube. The complete reaction system contained the following components: (a) 20 µl of purified pHBA 1-hydroxylase (6.6 µg of protein), (b) 20 µl of Trypsin Reaction Buffer (100 mM Tris-HCl (pH 8), 0.3 M NaCl, 2 mM CaCl$_2$, 2H$_2$O), and (c) 4 µl of the trypsin stock solution. The assembled reaction mixture was then transferred to 37° C. in a water bath. After a 90-min incubation period, the reaction was stopped with 4.8 µl of freshly prepared 10 mM PMSF phenylmethanesulfonyl fluoride (Sigma) dissolved in isopropanol. The terminated reaction was stored at –20° C. for subsequent HPLC analysis as described below.

The digested protein sample was supplemented with 50 µl of 0.1% (v/v) TFA in water and 80 µl, was separated on a RP 8 Symmetry Shield™ column (Waters, Mass., USA) with the dimensions 2.1×150 mM (100 Å, 5 µm) at a flow rate of 0.4 mL/min using the following conditions: Solvent A: H$_2$O, 0.1% (v/v) TFA, Solvent B: acetonitrile, 0.1% (v/v) TFA; 0–2 min 2% B, 2–5 min 2–10% B, 5–55 min 10–35% B, 55–85 min 35–85% B, 85–86 min 85–100% B, 86–90 min 100% B, 90–91 min 100-2% B, 100 min 2% B. Elution of peptides was monitored at 210 nm and fractions were collected manually. Carefully controlled experiments established that the polypeptide peaks collected for N-terminal sequence analysis resulted from trypsin digestion of pHBA 1-hydroxylase. In other words, these peaks were not observed if either the trypsin or pHBA 1-hydroxylase was omitted from the digest reaction mixture. Three fractions containing proteolytic fragments were dried down on a Sequelon AA membrane (Aryl-amino derivatized PVDF, Millipore, USA) and subjected to automated Edman degradation using a Beckman-Coulter LF3000 gas phase protein sequencer. Peptide 4 yielded the sequence Asn-Pro-Thr-Tyr-Thr-Tyr-Pro (SEQ ID NO:2). Peptide 5 yielded the sequence Gln-Tyr-Val-Gly-Asp-Val-Ile-Val-Gly-Tyr-Asp-Gly-Val-Arg (SEQ ID NO:3). Peptide 6 yielded the sequence Ala-Leu-Leu-Thr-Gly-Asp-Ser-Ser-Gly-Ala-Tyr-Asp-Thr (SEQ ID NO:4).

Six liters of *Candida parapsilosis* culture (ATCC 7336) were grown for 96 h in the presence of 25 mM pHBA as sole carbon source as described above. The culture (200 mL) was harvested and induction of pHBA 1-hydroxylase activity was confirmed by determining specific pHBA 1-hydroxylase activity in a cell free extract. pHBA 1-Hydroxylase activity was determined to be 0.13 U/mg. The remaining culture was harvested by centrifugation and washed in deionized water.

Total RNA was isolated by extraction with hot acidic phenol. Briefly, the cell pellet was resuspended in 5 mL of 10 mM Tris/HCl (pH 7.5), 10 mM EDTA, 0.5% (w/v) SDS, and an equal volume of liquefied, water-saturated, phenol was added. The yeast/phenol suspension was mixed vigorously and incubated for 45 min at 65° C. with occasional mixing. The cell lysate was centrifuged (10000×g, 20 min) and the aqueous phase was subjected to successive extractions with phenol and chloroform. The aqueous phase was supplemented with sodium acetate (pH 5.3) to reach a final concentration of 0.3 M. Nucleic acids were precipitated by adding two volumes (10 mL) of ethanol followed by centrifugation. RNA was washed with 70% ethanol, resuspended in water, visualized by electrophoresis in denaturing agarose gels, and quantitated spectrophotometrically. Approximately 4 mg of total RNA could be isolated from 6 L of yeast culture. Total RNA was also isolated in a similar fashion from 1 L of *Candida parapsilosis* culture grown in the presence of 100 mM glucose.

Complementary DNA (cDNA) was generated using 5 μg of total RNA isolated from *Candida parapsilosis* cultures grown in the presence of either glucose or pHBA as sole carbon source using, the first strand cDNA synthesis kit from MBI Fermentas (Amherst, N.Y.) according to the instructions of the manufacturer. Two degenerate oligonucleotides (Primer 1 and Primer 2) were synthesized according to sequence information provided by partial amino acid sequence of the purified pHBA 1-hydroxylase protein.

```
Primer 1 - (SEQ ID NO:5)
5'-ATGGCNGTNCARGCNCCNWSNAARACNTAYGG-3'

Primer 2 - (SEQ ID NO:6)
5'-CCRTCRTANCCNACDATNACRTCNCCNACRTA-3'
```

R indicates A/G, W indicates A/T, S indicates C/G, D indicates A/G/T, and N indicates where inosine nucleotides were incorporated in the synthetic oligonucleotides (MWG Biotech, High Point, N.C.). Primer 1 was reverse-translated from the sequence of the first 11 amino acids of the N-terminus of the purified pHBA 1-hydroxylase protein including the initiator methionine (that could not detected by Edman degradation because it is usually removed after translation). This sequence (Met-Ala-Val-Gln-Ala-Pro-Ser-Lys-Thr-Tyr-Gly) is set forth as SEQ ID NO:7. Primer 2 is the reverse complement of the DNA sequence reverse translated from the sequence of 11 amino acids of peptide 5. This sequence of 11 amino acids (Tyr-Val-Gly-Asp-Val-Ile-Val-Gly-Tyr-Asp-Gly) is set forth as SEQ ID NO:8.

A PCR reaction mixture (400 μL) containing 2.5 mM MgCl$_2$, 2 mM dNTPs, 10 mM Tris/HCl (pH 8.8), 50 mM KCl, 0.08% Nonidet P40, 1 μM of Primer 1 and Primer 2, 10 U Taq® polymerase (MBI Fermentas), and 2 μL of cDNA templates was created. The PCR mixture was divided into eight 50 μl aliquots and individual PCR reactions were performed in which annealing temperatures ranged (in two degree increments) from 40° C. to 54° C. Amplification was carried out for 40 cycles, each cycle comprising 45 sec at 94° C., 45 sec at the respective annealing temperature, and 1 min at 72° C. A 500 bp DNA fragment could be amplified at all annealing temperatures. This fragment was specific for cDNA templates derived from *Candida parapsilosis* cells grown on pHBA as the sole carbon source. The PCR fragment was gel-purified and cloned into the pCR2.1 vector (Invitrogen, USA) using the TOPO T/A cloning kit (Invitrogen, USA) according to manufacturer's instructions. Plasmid DNA was isolated from ten independently derived *E. coli* clones and subjected to DNA sequencing. DNA sequences were aligned using the SeqMan program of the Lasergene software package (DNASTAR, Madison, Wis.) which generated the consensus DNA sequence of 518 nucleotides set forth as SEQ ID NO:9. This DNA sequence could be translated into a protein fragment with the amino acid sequence set fort as SEQ ID NO:10. The deduced amino acid sequence comprises 14 amino acids of the N-terminus that was determined by Edman degradation of the purified pHBA 1-hydroxylase protein. Since this amino acid sequence was not used for the oligonucleotide design, Applicants concluded that the PCR fragment encoded the first 173 amino acid residues of the pHBA 1-hydroxylase enzyme that was purified. Interestingly, the protein fragment contained the Gly-Ala-Gly-Leu-Gly-Gly (SEQ ID NO:10, positions 25–30) sequence that matches the flavin binding motif (Gly-x-Gly-x-x-Gly), a unifying feature of flavin-dependent monooxygenases of prokaryotic and eukaryotic origin.

The remaining part of the pHBA 1-hydroxylase was isolated by 3'RACE (Invitrogen) as follows. Complementary DNA (cDNA) was generated using 5 μg of total RNA isolated from *Candida parapsilosis* cultures grown in the presence of either glucose or pHBA as the sole carbon source using the first strand cDNA synthesis kit from MBI Fermentas and Primer 3 according to the instructions of the manufacturer.

```
Primer 3 - (SEQ ID NO:11)
5'-GGCCACGCGTCGACTAGTACTTTTTTTTTTTTTT-3'
```

A PCR reaction mixture (400 μl) containing 2.5 mM MgCl$_2$, 2 mM dNTPs, 10 mM Tris/HCl (pH 8.8), 50 mM KCl, 0.08% Nonidet P40, 1 μM of Primer 4 and Primer 5, 10 U Taq® polymerase (MBI Fermentas) and 2 μl of cDNA templates was created. The PCR mixture was split up into four 100 μl aliquots and individual PCR reactions were performed in which annealing temperatures ranged (in two degree increments) from 54° C. to 60° C. Amplification was carried out for 40 cycles, each cycle comprising 45 sec at 94° C., 45 sec at the respective annealing temperature, and 1 min at 72° C.

```
Primer 4 - (SEQ ID NO:12)
5'-GGTTGATAGAGCCGAAGAATTGGGGGTTGAAATCC-3'

Primer 5 - (SEQ ID NO:13)
5'-GGCCACGCGTCGACTAGTAC-3'
```

Primer 4 corresponds to nucleotides 384–418 of the previously isolated PCR fragment of the pHBA 1-hydroxylase cDNA and Primer 5 anneals at the 3' end of each cDNA generated with Primer 3. An 1100 bp DNA fragment could be amplified at all annealing temperatures. This fragment was specific for cDNA templates derived from *Candida parapsilosis* cells grown on pHBA as sole carbon source. The DNA fragment was gel-purified. A PCR reaction mixture (1 mL) containing 2.5 mM MgCl$_2$, 2 mM dNTPs, 10 mM Tris/HCl (pH 8.8), 50 mM KCl, 0.08% Nonidet P40, 1 μM of Primer 4 and Primer 5, and 20 U Taq® polymerase was created and split into 100 μL aliquots. The aliquots received 1 to 10 μL of a 1:100 dilution of the gel purified PCR product. Amplification was carried out for 40 cycles, each cycle comprising 45 sec at 94° C., 45 sec at 60° C., and 1 min at 72° C. The reamplified PCR products were gel-purified and cloned into the pCR2.1 vector using the TOPO T/A cloning kit according to manufacturer's instructions.

Plasmid DNA was isolated from four independently derived *E. coli* clones and subjected to DNA sequencing. The new DNA sequences and those of the previously cloned fragment of the pHBA 1-hydroxylase cDNA (SEQ ID NO:9)

were aligned using the SeqMan program of the Lasergene software package (DNASTAR) which generated the consensus DNA sequence of 1526 nucleotides set forth as SEQ ID NO:14. This sequence contains an open reading frame (ORF) of 1440 nucleotides (SEQ ID NO:15) that was translated into a protein of 480 amino acids (SEQ ID NO:16). The amino acid sequence of this protein contains all sequence information that was generated from the purified pHBA 1-hydroxylase protein (see SEQ ID Nos:1–4) with the exception of two amino acid residues. Residue seven of SEQ ID NO:16 is tryptophan whereas N-terminal sequence analysis of the pHBA 1-hydroxylase protein (SEQ ID NO:1) revealed a serine at this position. Careful inspection of the sequence alignment of all ten PCR-derived clones (see above) revealed that the sequence WSN of the Primer 1 (SEQ ID NO:5) had been converted to T<u>G</u>G (which encodes for Trp) in six out of ten clones. In the four other clones the sequence T<u>C</u>G (which encodes for Ser) was determined. Thus, the discrepancy between the experimentally determined sequence of the pHBA 1-hydroxylase enzyme and the deduced amino acid sequence of the PCR-derived cDNA is an experimental artifact that can be attributed to the use of a degenerate oligonucleotide primer.

The second discrepancy between the partial amino acid sequence of the protein and the deduced amino acid sequence of the PCR-derived cDNA pertains to the third amino acid (valine) of Peptide 5, which is a serine in SEQ ID NO:16. Careful inspection of the output of the Edman degradation of Peptide 5 indicated that in the third degradation cycle a second peak, corresponding to serine, was detected and that this peak was nearly as abundant as that of valine.

A 5' RACE experiment was conducted to determine the precise sequence of the 5' region of the pHBA 1-hydroxylase transcript. Briefly, complementary DNA (cDNA) was generated using 5 µg of total RNA isolated from *Candida parapsilosis* cultures grown in the presence of pHBA as sole carbon source using the first strand cDNA synthesis kit from MBI Fermentas and Primer 6 according to the instructions of the manufacturer. This primer represents the reverse complement of the sequence from nucleotide 384–418 of the pHBA 1-hydroxylase open reading frame (SEQ ID NO:15).

```
Primer 6 - (SEQ ID NO:17)
5'-GGATTTCAACCCCCAATTCTTCGGCTCTATCAACC-3'
```

After the reverse transcriptase reaction was complete, RNA was degraded with RNAseH (Stratagene, LaYolla, Calif.) according to the instructions of the manufacturer. The cDNA was cleaned using the QIAquick PCR purification kit (Qiagen, MD) and C-tailed using recombinantly produced terminal transferase of calf thymus (New England Biolabs, Beverly, Mass.) according to manufacturer's instructions.

A PCR reaction mixture (100 µL) containing 2.5 mM MgCl$_2$, 2 mM dNTPs, 10 mM Tris/HCl (pH 8.8), 50 mM KCl, 0.08% Nonidet P40, 1 µM of Primer 7 and Primer 8, 10 U Taq® polymerase, and 2 µL of C-tailed cDNA templates was combined. The PCR mixture was divided into two 100-µL aliquots and two PCR reactions were performed at annealing temperatures of 50° C. and 52° C., respectively. Amplification was carried out for 40 cycles, each cycle comprising 45 sec at 94° C., 45 sec at the respective annealing temperature, and 1 min at 72° C. Primer 7 anneals to the C-tail of the cDNA. Primer 8 represents the reverse, complement of the sequence from nucleotide 175–204 of the pHBA 1-hydroxylase open reading frame (SEQ ID NO:15).

```
Primer 7 - (SEQ ID NO:18)
5'-GGCCACGCGTCGACTAGTACGGGNNGGGNNGGGNNG-3'

Primer 8 - (SEQ ID NO:19)
5'-CTTGGTTGATGGTGGTGGAATTTGAATACC-3'
```

"N" indicates the position where inosine nucleotides were incorporated into the synthetic oligonucleotide. PCR products of 200–400 bp were gel-purified. The gel-purified DNA was diluted 1:1000 and 10 µl was used in a PCR reaction mixture (1 mL) containing 2.5 mM MgCl$_2$, 2 mM dNTPs, 10 mM Tris/HCl (pH 8.8), 50 mM KCl, 0.08% Nonidet P40, 1 µM of Primer 7 and Primer 8, and 20 U Taq® polymerase. The PCR mixture was divided into ten 100 µL aliquots and PCR was carried out for 40 cycles, each cycle comprising 45 sec at 94° C., 45 sec at 52° C., and 1 min at 72° C. The reamplified PCR products were gel-purified and cloned into the pCR2.1 vector using the TOPO T/A cloning kit according to manufacturer's instructions. Plasmid DNA was isolated from two independently derived *E. coli* clones and subjected to DNA sequencing. These clones were found to contain identical DNA fragments of 264 bp that comprise the first 204 nucleotides of the pHBA 1-hydroxylase open reading frame and 60 nucleotides of new sequence that represents the 5' untranslated region of the pHBA 1-hydroxylase transcript. The nucleotide sequence of the 5' RACE product is set forth as SEQ ID NO:20.

DNA sequences derived from RT-PCR experiments, 3' RACE experiments (represented by the consensus sequence of SEQ ID NO:14), and 5' RACE experiments (represented by the consensus sequence of SEQ ID NO:20) were aligned using the SeqMan program of the Lasergene software package (DNASTAR) which generated a consensus DNA sequence of 1586 nucleotides set forth as SEQ ID NO:21. This sequence is the precise sequence of the pHBA 1-hydroxylase transcript including a 5' untranslated region of 60 nucleotides, a coding region of 1440 nucleotides, a 3' untranslated region of 66 nucleotides, and a poly-A tail of 20 nucleotides. The open reading frame encoding the pHBA 1-hydroxylase protein is set forth as SEQ ID NO:22. The conceptual translation of this sequence to the primary amino acid sequence of the pHBA 1-hydroxylase protein is set forth as SEQ ID NO:23.

Example 3

Expression of the pHBA 1-hydroxylase Gene in *E. coli* and Biochemical Characterization of the Recombinantly Produced pHBA 1-hydroxylase Enzyme This work was initiated before the unambiguous sequence of the pHBA 1-hydroxylase transcript (SEQ ID NO:21) was known. Complementary DNA (cDNA) was generated using 5 µg of total RNA isolated from *Candida parapsilosis* (ATCC 7336) cultures grown in the presence of pHBA as the sole carbon source using the first strand cDNA synthesis kit from MBI Fermentas according to the instructions of the manufacturer. A new primer (Primer 9) was synthesized.

```
Primer 9 - (SEQ ID NO:24)
5'-CCCGCACATaagcttAGCCTGATGCACTTAATGG-3'
```

The underlined nucleotides of Primer 9 anneal at the 3' end of the pHBA 1-hydroxylase. Nucleotides in small caps introduce a HindIII restriction site immediately following the stop codon.

A PCR reaction mixture (100 µL) containing 2.5 mM MgCl$_2$, 2 mM dNTPs, 10 mM Tris/HCl (pH 8.8), 50 mM KCl, 0.08% Nonidet P40, 1 µM of Primer 1 (SEQ ID NO:5) and Primer 9, 10 U Taq® polymerase, and 2 µL of cDNA templates was combined. PCR was carried out for 35 cycles, each cycle comprising 45 sec at 94° C., 45 sec at 54° C., and 2 min at 72° C. PCR products were gel-purified and cloned into the pCR2.1 vector using the TOPO T/A cloning kit according to manufacturer's instructions.

Plasmid DNA was isolated from six independently derived E. coli clones and subjected to DNA sequencing. Comparing the DNA sequences to SEQ ID NO:14 revealed that the nucleotide sequence of two clones was free of PCR-induced mutations. However, for reasons discussed above, the two clones carry the T<u>G</u>G codon (encoding a tryptophan residue) at position 7 of the pHBA 1-hydroxylase protein instead of the T<u>C</u>G codon (encoding a serine residue) that was determined by Edman degradation of the N-terminus of the purified pHBA 1-hydroxylase protein. Therefore, the DNA insert of these clones could not be used directly for heterologous expression of the pHBA 1-hydroxylase gene. Instead, a new primer (Primer 10, SEQ ID NO:25) was synthesized.

```
Primer 10 - (SEQ ID NO:25)
5'-GAATTCGCCcatATGGCGGTGCAGGCGCCGTCGAAGACG-3'
```

The underlined nucleotides of Primer 10 anneal at the 5' end of the pHBA 1-hydroxylase transcript. Nucleotides in small caps introduce a Nde I restriction site at the start codon. Nucleotides in bold change the TGG codon in the PCR products generated with Primer 1 to the TCG codon encoding serine. Underlined nucleotides in italics anneal to sequences in the pCR2.1 vector used to clone the PCR products representing the coding region of the pHBA 1-hydroxylase protein.

Plasmid DNA of a PCR error-free clone described above and Primers 9 and 10 were used to amplify a PCR fragment suitable for cloning into the pET29A vector. A PCR reaction mixture (100 µL) containing 2.5 mM MgCl$_2$, 2 mM dNTPs, 10 mM Tris/HCl (pH 8.8), 50 mM KCl, 0.08% Nonidet P40, 1 µM of Primer 10 and Primer 9, 10 U Taq® polymerase, and 10 ng of plasmid DNA was created. PCR was carried out for 25 cycles, each cycle comprising 45 sec at 94° C., 45 sec at 60° C., and 2 min at 72° C. PCR products were digested with Nde I and Hind III, gel purified, and ligated to pET29A DNA that had been digested with the same enzymes.

Three recombinant clones were recovered. Plasmid DNA was isolated and sequenced. No PCR-induced mutations were discovered. The DNA sequence of the insert cloned into the pET29a vector is set forth as SEQ ID NO:26. It encoded an enzyme with an amino acid sequence identical to that of SEQ ID NO:23. Plasmid DNA of a pET29a construct harboring the pHBA 1-hydroxylase insert was electroporated into E. coli BL21 DE3 cells (Novagen, Madison, Wis.). Recombinant clones were used to inoculate 100 mL of LB medium containing 50 µg/mL kanamycin. The culture was grown at 37° C. until the cells had reached a density of OD$_{\lambda=600\,nm}$ of 0.6. Subsequently, the culture was cooled to room temperature on ice, IPTG was added to a final concentration of 0.2 mM, and growth of the culture was allowed to proceed at 23° C. for 24 h.

Culture was harvested (1.5 mL) by centrifugation. Cells were washed with 10 mM Tris/H$_2$SO$_4$ (pH 7.8), 0.5 mM DTT, 0.5 mM EDTA, 10 µM FAD and finally resuspended in 150 µL of the same buffer. Toluene (15 µL) was added to the cell suspension and cells were incubated at 37° C. for 10 min. A 25-µL reaction mixture was combined containing 1 mM pHBA, 2 mM NADH, 10 µM FAD, and 10 mM KPO$_4$ (pH 7.6) and this reaction mixture received either 15 µL of pHBA 1-hydroxylase enzyme (1.14 U/mL) purified from Candida parapsilosis or 15 µL of the toluene-treated E. coli cell suspension. Enzyme reactions were incubated at 30° C. for 30 min. The reaction was stopped by adding an equal volume of MeOH containing 12% (v/v) acetic acid.

The reaction products were clarified by centrifugation (13000×g, 10 min) and analyzed by HPLC as follows. Reaction products were injected (10 µL) onto a Nova Pak C18 column (3.9×150 mm, 60 Å, 4 µm) (Waters, MA, USA). The column was developed at a flow-rate of 1 mL/min under the following conditions: Solvent A (H$_2$O/1.5% HPO$_4$), Solvent B (48% Acetonitrile/H$_2$O/1.5% HPO$_4$); 0–5 min 0% B, 5–20 min 0–100% B, 20–21 min 100–0% B, 21–25 min 0% B. pHBA was detected at 254 nm and hydroquinone at 288 nm. Compounds corresponding to pHBA and hydroquinone were identified based on retention time and UV absorption spectra that were indistinguishable from those of authentic pHBA and hydroquinone standards. HPLC analysis revealed that toluene-treated E. coli cells harboring the pET29a pHBA 1-hydroxylase plasmid contained an enzyme activity that was able to convert pHBA to hydroquinone in the presence of NADH. This activity was not observed with E. coli cells containing the empty pET29a vector (control). This is conclusive evidence that the isolated cDNA encodes a polypeptide that has pHBA 1-hydroxylase activity.

The recombinantly produced pHBA 1-hydroxylase protein was purified to homogeneity in order to obtain sufficient material for analysis of kinetic properties of the enzyme. Briefly, four 5-liter flasks containing 1 L of LB medium supplemented with 50 µg/mL kanamycin were inoculated with E. coli BL21 cells containing the pET29A pHBA 1-hydroxylase construct. The culture was grown at 26° C. until a cell density (OD$_{\lambda=600\,nm}$) of 0.6 was achieved. IPTG was then added to a final concentration of 0.4 mM followed by continued culture at 26° C. for 36 h. Cells were harvested by centrifugation (5000×g, 10 min) and resuspended in 30 mL of 20 mM Tris/H$_2$SO$_4$ (pH 7.8), 0.5 mM DTT, 0.5 mM EDTA, 0.5 mM PMSF, and 10 µM FAD. The cell suspension was passed twice through a French press and cleared by centrifugation (30000×g, 20 min, 4° C.). Glycerol was added to a final concentration of 7% (v/v). This extract was stored at −80° C. without loss of pHBA 1-hydroxylase enzyme activity. The protein concentration was 35 mg/mL and specific activity was 0.52 U/mg protein. Thus, the culture provided a protein extract of 30 mL representing a total of 1044 mg of protein containing 547 U of pHBA 1-hydroxylase activity.

The enzyme extract (15 mL) was buffer-exchanged in 2.5 mL aliquots on PD10 columns into 10 mM Tris/H$_2$SO$_4$ (pH7.8), 0.5 mM DTT, 0.5 mM EDTA, and 10 µM FAD. Buffer-exchanged protein was combined to give a total volume of 21 mL. The buffer-exchanged protein consisted of 216 mg of protein representing 123 U of pHBA 1-hydroxylase activity. Buffer-exchanged extract (7 mL) was loaded onto a Q-sepharose column (15 mL gel bed volume). The column was developed at a flow rate of 2 mL/min at 4° C. as follows: Solvent A (10 mM Tris/H$_2$SO$_4$ (pH 7.8), 0.5 mM DTT, 0.5 mM EDTA, and 10 µM FAD), Solvent B (10 mM Tris/H$_2$SO$_4$ (pH 7.8), 0.5 mM DTT, 0.5 mM EDTA, 10 µM FAD, and 1 M NaSO$_4$); 0–9 min 0% B, 9–44 min (linear gradient) 0–20% B, 44–54 min (linear gradient) 20–60% B, 54–55 min 60–0% B, 55–65 min 0% B. Fractions (4 mL) were collected and pHBA 1-hydroxylase activity in the fractions was monitored using the spectrophotometric assay described above. The remaining 14 mL of buffer-exchanged protein was processed in two additional chromatography runs carried out under identical conditions. A total of 124 U of pHBA 1-hydroxylase enzyme, representing about 87% of the column load, could be recovered from all chromatography runs in the eight 4-mL fractions. The fractions were pooled and concentrated to a final volume of 2.5 mL using Centriprep centrifugal concentrators.

The protein was desalted on PD10 columns using 10 mM NaPO$_4$ (pH 6.8), 10 µM CaCl$_2$, 1 mM DTT, and 10 µM FAD. The desalted sample, representing 22.89 mg of protein containing 72 U of pHBA 1-hydroxylase enzyme, was diluted with 1 volume (3.5 mL) of desalting buffer and injected onto a 118×15 mm Bio-Scale CHT20-1 hydroxylapatite column (Bio-Rad, Hercules, Calif.) pre-equilibrated with 10 mM sodium phosphate (pH6.8), 10 µM CaCl$_2$, 1 mM DTT, and 10 µM FAD. The column was developed at 2 mL/min (4° C.) with a linear gradient (25 mL) of 10–350 mM sodium phosphate (pH 6.8; containing 0.01 mM CaCl$_2$, 1 mM DTT, and 10 µM FAD). Fractions (8 mL) were collected and pHBA 1-hydroxylase activity in the chromatography fractions was monitored spectrophotometrically. Protein (7 mg), containing 63 U of pHBA 1-hydroxylase enzyme, was recovered in a single, 8-mL fraction. A 20 µl aliquot of this fraction was analyzed by SDS-PAGE. Visual inspection of the Coomassie-stained gel indicated that the pHBA 1-hydroxylase protein was >95% pure.

Protein (2 mL) was concentrated to a final volume of 400 µl using a Centricon-10 (Millipore Corp.). The final concentration of the purified recombinant pHBA 1-hydroxylase protein was 5.033 mg/mL, which corresponds to a monomer concentration of 95.763 µM. Protein concentration was calculated using an extinction coefficient of 71, 270 M$^{-1}$ at 280 nm, as determined by the GCG Peptidesort program using the amino acid composition given in SEQ ID NO:23.

The protein was diluted 10-fold in 50 mM KPO$_4$ (pH 6.8) and 10 µM FAD. The diluted enzyme (2 µL) was used to measure pHBA 1-hydroxylase activity spectrophotometrically in the presence of 50 mM KPO$_4$ (pH 6.8), 0.1 mM pHBA, 0.2 mM NADH, and 10 µM FAD in a final volume of 500 µL. Activity was measured in four replicates. The following rates of pHBA 1-hydroxylase were determined at 25° C.: 23.776, 20.416, 23.552, and 22.256 µM/min. From this information and the molecular weight of the pHBA 1-hydroxylase enzyme of 52559.44 Da, the Kcat of the pHBA 1-hydroxylase enzyme could be calculated to be 9.77±0.69 s$^{-1}$.

Figure 2:
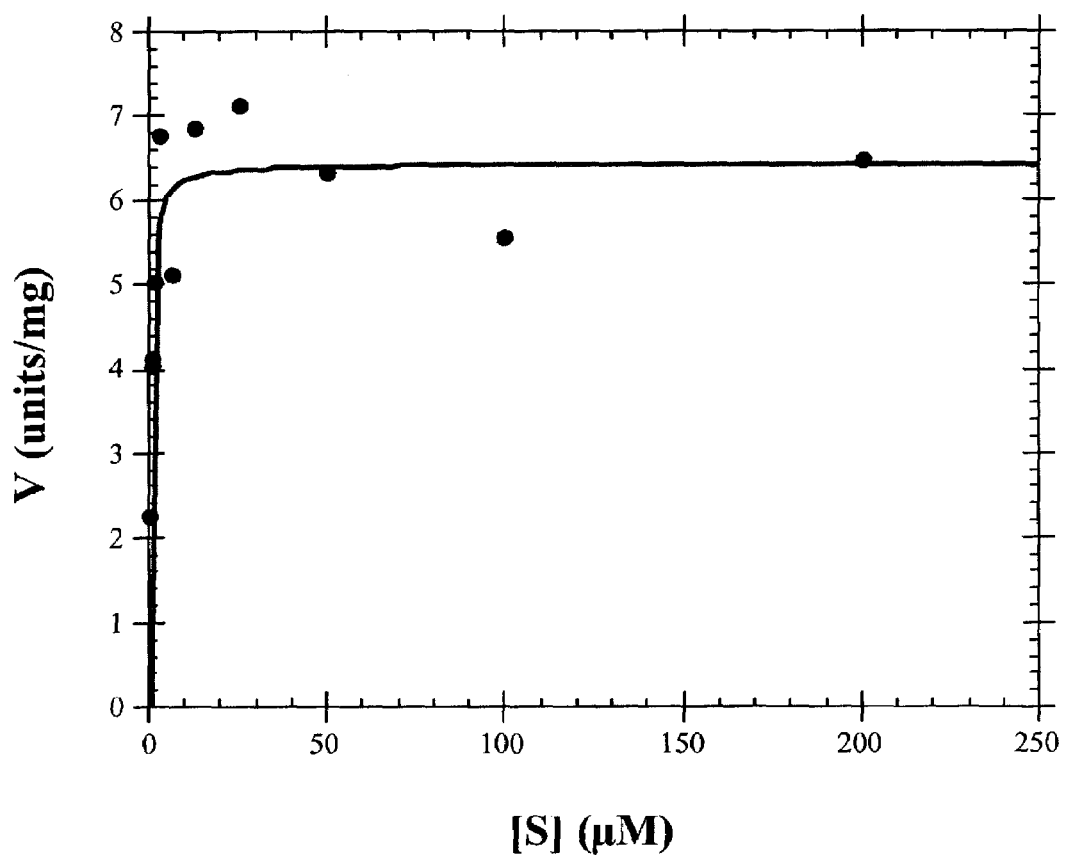
FIG. 2 shows a kinetic analysis of the purified recombinant pHBA 1-hydroxylase protein with pHBA as a substrate. Initial rates of product formation are plotted against substrate concentration.

The K$_m$ of the enzyme was determined under similar conditions. Five microliters of 0.903 µM pHBA 1-hydroxylase enzyme was used in the standard 500 µl assay described above. Initial rates were measured at 340 nm over a 15 sec interval, at various concentrations of pHBA ranging from 0.2 to 400 µM; the resulting data was fitted to the Michaelis-Menten equation. Under these conditions, apparent K$_m$ and V$_{max}$ values were 0.31 µM and 6.4 µmol/min/mg, respectively (FIG. 2).

Example 4

Generation of Transgenic Plants that Overproduce pHBA
PCR-Cloning of *E. coli* CPL Two PCR primers were used to amplify the *E. coli* ubiC gene from genomic DNA, while adding unique restriction sites to its flanking regions for subsequent ligation into a high copy number plasmid. This gene codes for chorismate pyruvate lyase (CPL). The primers used for this purpose were based on the published DNA sequences of the *E. coli* ubiC gene (GenBank® Accession number M96268) as follows:

```
Primer 11 - (SEQ ID NO:27):
5'-CTACTCATTTcatatgTCACACCCCGCGTTAA-3'

Primer 12 - (SEQ ID NO:28):
5'-CATCTTACTagatctTTAGTACAACGGTGACGCC-3'
```

The underlined bases hybridize to the target gene, while lower case letters indicate the restriction sites (NdeI or BglII) that were added to the ends of the PCR primers.

Amplification of the *E. coli* ubiC gene was achieved using Primers 11 (SEQ ID NO:27) and 12 (SEQ ID NO:28) and genomic DNA from *E. coli* strain W3110 (Campbell et al., *Proc. Natl. Acad. Sci.*, 75:2276–2284 (1978)). Primer 11 hybridizes at the start of the gene and introduces a NdeI site at the protein's initiation codon, while Primer 12 hybridizes at the opposite end and provides a BglII site just past the termination codon. The 100 µL PCR reactions contained approximately 100 ng of genomic DNA and both primers at a final concentration of 0.5 µM. The other reaction components were obtained from the GeneAmp® PCR Reagent Kit (Perkin Elmer, Boston, Mass.), according to the manufacturer's protocol. Amplification was carried out in a DNA Thermocycler 480 (Perkin Elmer) for 22 cycles, each cycle comprising 1 min at 94° C., 1 min at 55° C., and 1 min at 72° C. Following the last cycle, there was a 7-min extension period at 72° C.

The PCR product was cut with NdeI and BglII, and the resulting fragment was ligated into the *E. coli* expression vector, pET-24a (+) (Novagen) that had been digested with NdeI and BamHI. The ligation reaction mixture was used to transform *E. coli* DH10B electocompetent cells (GibcoBRL-Life Technologies, Rockville, Md.) using a BTX Transfector 100 (Biotechnologies and Experimental Research Inc., San Diego, Calif.) according to the manufacturer's protocol; growth was selected on LB media that contained kanamycin (50 µg/mL). Transformants that contained plasmids with a CPL insert were identified through PCR reactions, using Primers 11 (SEQ ID NO:27) and 12 (SEQ ID NO:28) and individual resuspended colonies as the source of template; from hereon, this technique is simply referred to as "colony PCR".

Plasmid DNA was isolated from a representative colony that yielded a PCR product of the correct size. The entire insert corresponding to the CPL was sequenced completely to check for PCR errors; none were found. The plasmid that was selected for further manipulation is referred to below as "pET24a-CPL". The nucleotide sequence of the ORF for CPL in the pET24a *E. coli* expression construct and its predicted primary amino acid sequence are set forth in SEQ ID NO:29 and SEQ ID NO:30, respectively.

Construction of a Chloroplast-Targeted Version of CPL: TP-CPL

Chorismate is localized in chloroplasts and other types of plastids (Siebert et al., *Plant Physiol.*, 112:811–819 (1996)) and it was therefore essential to provide CPL with an N-terminal chloroplast targeting sequence that would efficiently direct the foreign protein to chloroplasts, the site of chorismate production. This was accomplished by constructing a chimeric protein that included of a chloroplast targeting sequence derived from the tomato Rubisco small subunit precursor protein fused to the initiator Met residue of CPL; the resulting fusion protein is referred to below as "TP-CPL". PCR was employed to generate a DNA fragment corresponding to the transit peptide of the Rubisco small subunit and first four amino acid residues of "mature" Rubisco. The target for amplification was the plasmid pTSS1-91-(#2)-IBI (Siebert et al., *Plant Physiol.,* 112:811–819 (1996)), which contains a full-length cDNA clone of the tomato Rubisco small subunit precursor for rbcS2 (Sugita et al., *Mol Gen Genet.,* 209:247–256 (1987); Siebert et al., *Plant Physiol.,* 112:811–819 (1996)). The following primers were used this reaction:

```
Primer 13 - (SEQ ID NO:31):
5'-CTACTCACTTAGATCTccatggCTTCCTCTGTCATTTCT-3

Primer 14 - (SEQ ID NO:32):
5'-CATCTTACTcatatgCCACACCTGCATGCAGC-3'
```

The underlined portion of Primer 13 (SEQ ID NO:31) hybridizes to the first 21 nucleotides of the Rubisco small subunit precursor and introduces an NcoI site (lower case letters) at the initiator Met residue at the start of the chloroplast targeting sequence. As indicated, this primer also contains a BglII site (bold letters) at its 5' end that is just upstream from the NcoI site. Primer 14 (SEQ ID NO:32) hybridizes at the other end of the chloroplast targeting sequence to nucleotides 167–184 of the ORF of the Rubisco small subunit precursor.

A unique NdeI site was engineered into this primer (lower case letters) to allow attachment of the PCR fragment containing the chloroplast targeting sequence to the NdeI site that is situated at the start codon of CPL in the pET-24a expression construct. The 100-μL PCR reaction contained approximately 75 ng of pTSS1-91-(#2)-IBI and Primers 13 (SEQ ID NO:31) and 14 (SEQ ID NO:32), both at a final concentration of approximately 0.9 μM. Amplification was carried out in a DNA Thermocycler 480 (Perkin Elmer) for 25 cycles, each cycle comprising 1 min at 94° C., 1 min at 55° C., and 1 min at 72° C.; the last cycle was followed by a 7-min extension period at 72° C. The PCR product was digested with BglII and NdeI, and ligated into pET24a-CPL that had been cleaved with the same restriction enzymes to remove a small DNA fragment (106 bp) that contained only vector sequence, including the T7 promoter. The ligation reaction mixture was introduced into *E. coli* DH10B cells using electroporation, and growth was selected on LB media with kanamycin (50 μg/mL). Transformants harboring plasmids with the inserted chloroplast targeting sequence were identified by colony PCR using Primers 12 (SEQ ID NO:28) and 13 (SEQ ID NO:31). A representative plasmid yielding a PCR product of the correct size was selected for further manipulation; this plasmid is referred to below as "pET24a-TP-CPL". To confirm the absence of PCR errors, the region of the plasmid corresponding to the amplified chloroplast targeting sequence was sequenced completely using custom designed primers. The nucleotide sequence of the ORF for TP-CPL and its predicted primary amino acid sequence are set forth in SEQ ID NO:33 and SEQ ID NO:34, respectively.

Construction of the Expression Plasmid used for *arabidopsis* and Tobacco Transformation To generate a construct that could be used for constitutive expression in *arabidopsis* and tobacco, the DNA fragment corresponding to the full-length TP-CPL fusion protein was subcloned into a modified version of plasmid pML63. The latter was derived from pML40, which contains the following genetic elements: a CaMV 35S promoter, a cab leader sequence, the uidA coding region, and the NOS polyadenylation signal sequence. The CaMV 35S promoter is a 1.3 kb DNA fragment that extends 8 base pairs past the transcription start site (Odell et al., *Nature,* 303:810–812 (1985)). Operably linked to its 3' end is the cab leader sequence, a 60 bp untranslated double-stranded piece of DNA that was obtained from the chlorophyll a/b binding protein gene 22L (Harpster et al., *Mol. Gen. Genet.,* 212:182–190 (1988)). Fused to the 3' end of the cab leader is the uidA gene (Jefferson et al., *EMBO J.,* 6:3901 (1987)) that encodes the protein β-glucuronidase (e.g., "GUS"). Finally, attached to 3' end of the GUS gene is an 800 bp DNA fragment containing the polyadenylation signal sequence from the nopaline synthase (e.g., "NOS") gene (Depicker et al., *J. Mol. Appl. Genet.,* 1:561–564 (1982)). These DNA fragments, together comprising a 35S-GUS chimeric gene, were inserted by standard cloning techniques into the vector pGEM9Zf (−) (Promega, Madison, Wis.) to yield plasmid pMH40.

Plasmid pML63 (which is basically the same as pMH40 but has a truncated version of the 3' NOS terminator sequence) was generated in the following manner. First, pMH40 was digested with Sal I and the two resulting DNA fragments of 4.03 kb and 2.9 kb were re-ligated to yield a plasmid, pML3, with the 35S promoter/cab22 leader/GUS gene/3' NOS terminator cassette in the opposite orientation. pML3 was then digested with Asp718 I and Hind III to release a 770 bp fragment that contained the 3' NOS terminator sequence. The latter was discarded and replaced with a shorter version that was generated by PCR using pMH40 as a template and Primers 15 (SEQ ID NO:35) and 16 (SEQ ID NO:36).

```
Primer 15 - (SEQ ID NO:35): 5'-CCCGGGGGTACCTAAAGAAGGAGTGCGTCGAAG-3'

Primer 16 - (SEQ ID NO:36): 5'-GATATCAAGCTTTCTAGAGTCGACATCGATCTAGTAACATAGATG A-3'
```

The PCR product was digested with Hind III and Asp718 I to yield a 298 bp fragment that contains 279 bp of the 3' NOS terminator sequence, starting at nucleotide 1277 (the TAA stop codon) and ending at nucleotide 1556 of the published sequence (Depicker et al., *J. Mol. Appl. Genet.,* 1:561–574 (1982)). Ligation of this PCR fragment into the retained part of pML3 yielded the plasmid pML63.

As indicated above, pML63 contains the GUS coding region under the control of the 35S promoter and a truncated version of the 3' NOS terminator. It therefore contains all of the transcriptional information that is necessary for the constitutive expression of GUS in plants. To generate an analogous construct for TP-CPL, plasmid pML63 was digested with Nco I and EcoRI. This manipulation releases only the GUS gene insert, leaving the regulatory flanking sequences and the rest of the vector intact. Plasmid pet24a-TP-CPL was also treated with NcoI and EcoRI, which liberates the entire coding region of the TP-CPL fusion protein. The small DNA fragment (693 bp) corresponding to the latter was purified by agarose gel electrophoresis and subjected to a standard ligation reaction with the large vector fragment (4.63 bp) that was obtained from cutting pML63 with Nco I and EcoRI. The ligation reaction mixture was introduced into *E. coli* DH10B using electroporation, and growth was selected on LB media that contained ampicillin (100 µg/mL). Transformants harboring plasmids with the inserted TP-CPL coding sequence were identified by colony PCR using Primers 12 (SEQ ID NO:28) and 13 (SEQ ID NO:31). A representative plasmid that yielded a PCR product of the correct size was selected for further manipulation, and this construct is referred to below as "TP-CPL-pML63".

The binary vector that was used for *Agrobacterium*-mediated, leaf disc transformation of tobacco was the plasmid pZBL1 (ATCC 209128). pZBL1 contains the origin of replication from pBR322, the bacterial nptI kanamycin resistance gene, the replication and stability regions of the *Pseudomonas aeruginosa* plasmid pVS1 (Itoh et al., *Plasmid*, 11 (3): 206–220 (1984)), T-DNA borders described by van den Elzen et al. (*Plant Mol. Biol.*, 5(3): 149–154 (1985)) wherein the OCS enhancer (extending from −320 to −116 of the OCS promoter (Greve et al., *J. Mol. Appl. Genet.*, 1:499–511(1983)) that is part of the right border fragment is removed, and a NOS/P-nptII-OCS 3' gene to serve as a kanamycin resistant plant selection marker.

For expression of TP-CPL, plasmid pZBL1 was digested with Sal I which cuts at a unique site between the right and left borders that is ideally situated for the insertion of foreign genes and stable integration into the plant genome. To minimize the possibility of re-ligation without an insert, the cut vector was dephosphorylated using Calf Intestinal Alkaline Phosphatase (GibcoBRL-Life Technologies) according to the manufacturer's recommendations. To obtain the fragment that would be inserted into the binary vector, plasmid TP-CPL-pML63 was also digested with SalI. This treatment releases the entire transcriptional unit for the TP-CPL fusion gene (e.g., 35S promoter/cab22 leader/TP-CPL/3' NOS terminator) as a 2.4 kb DNA fragment. The latter was purified by agarose gel electrophoresis and subjected to a standard ligation reaction with the dephosphorylated 11.0 kb fragment that was obtained from pZBL1 as described above. The ligation reaction mixture was introduced into *E. coli* DH10B using electroporation, and growth was selected on LB media with kanamycin (50 µg/mL). Transformants harboring plasmids with the TP-CPL fusion gene were identified by colony PCR using Primers 12 (SEQ ID NO:28) and 13 (SEQ ID NO:31), and the orientation of the insert was determined by restriction digestion analysis using KpnI. The plasmid that was selected for further manipulation is referred to as "TP-CPL-pZBL1". As described in more detail below, this expression construct was used to transform tobacco and *arabidopsis* for overproduction of pHBA.

Generation of Transgenic Tobacco Plants Expressing TP-CPL

Plasmid TP-CPL-pZBL1 was introduced into *Agrobacterium tumefaciens* strain LBA4404 (Hoekema et al., *Nature*, 303:179–180 (1983)) using the freeze-thaw transformation procedure (Holsters et al., *Mol. Gen. Genet.*, 163:181–187 (1978)). The cells were plated at 28° C. on YEP media (10 g Tryptone, 10 g Yeast Extract, and 5 g NaCl per liter) that also contained kanamycin (1000 µg/mL) and rifampicin (20 µg/mL). Colonies harboring the binary construct were identified by PCR using appropriate primers.

Potted tobacco plants (*Nicotiana tabacum* cv. Xanthi) for leaf disk infections were grown in a growth chamber maintained for a 14 h, 21° C. day/10 h, 18° C. night cycle, with approximately 80% relative humidity, under mixed cool white fluorescent and incandescent lights. *Agrobacterium*-mediated, leaf disk transformations were performed essentially as described by De Blaere et al., (*Meth. Enzymol*, 153:277–292 (1987)) with the following modifications. Leaf disks, 8 mm in diameter, were prepared from whole leaves using a sterile paper punch and 4 to 6 week old plants. Leaf disks were inoculated by submerging them for 30 min in concentrated solution of *Agrobacterium* harboring TP-CPL-pZBL1 resuspended to an density of $OD_{\lambda=600\ nm}=0.8$ in Murashige's Minimal Organics Media. Inoculated leaf disks were placed directly on media, that contained (per liter) 30 g of sucrose, 1 mg of 6-benzylaminopurine (BAP), 0.1 mg of napthaleneacetic acid, 8 g of agar, and 1 package of Murashige's Minimal Organics Medium that was obtained from GibcoBRL-Life Technologies (cat. #23118-029). After incubation for 3 d at 28° C. in the light, leaf disks were transferred to fresh media of the same composition that also contained kanamycin (300 µg/mL) and cefotaxime (500 µg/mL) to select for the growth of transformed tobacco cells and eliminate residual *Agrobacterium*. Leaf disks were incubated under the growth conditions described above for 3 weeks and were then transferred at 3-week intervals to fresh media of the same composition until optimal shoot size was obtained for root induction. Shoots were rooted on media containing (per liter) 1 package of Murashige's Minimal Organics Medium, 8 g of agar, and 10 g of sucrose. Approximately 4 weeks later, the plants were transferred to soil and allowed to grow to maturity in a growth chamber under the conditions described above.

Preparation of Tobacco Leaf Samples and HPLC Analysis of pHBA Glucose Conjugates.

Healthy leaf tissue (50–100 mg fresh weight) was rapidly removed from the distal one-third portion of the leaf and placed in a Biopulverizer™ h Tube (cat. #6570-201 or 6540-401) that contained a ceramic bead; both of the latter were obtained from QBiogen (Carlsbad, Calif.). After the addition of 1 mL of 50% methanol (v/v), the tubes were capped and mechanically agitated at room temperature for 40 sec, using a FastPrep® FP120 (QBiogen) tissue disruption apparatus that was operating at a speed of 5 m/sec. The tubes were then placed on a rotary shaker and vigorously agitated at 400 rpm for 1 h at room temperature. The extract was clarified by centrifugation (10,000×g, 10 min) using a conventional tabletop microfuge, and the supernatant which contained both pHBA glucose conjugates (phenolic and ester glucosides) was carefully removed to an empty tube. In the next step, a 50-µL aliquot of the methanol extract was transferred to a fresh microfuge tube, and the sample was taken to complete dryness under vacuum in a Speed-Vac® (Thermo Savant, Holbrook, N.Y.), using the optional heat setting. The dry residue was dissolved in 100 µL of 5 mM Tris-HCl (pH 8), and the sample was passed through a 0.22 µm cellulose acetate filter to remove small particles; a Spin-X Centrifuge Tube Filter (Costar®-Corning Inc. Life Sciences, Acton, Mass.; cat. #8160) was used for this purpose.

An aliquot (10–80 µL) of the filtered sample was then applied to a Vydac 218TP54 Protein and Peptide C18 column (Grace Vydac, Hesperia, Calif.) that was pre-equilibrated at 1 mL/min with 90% Buffer A (0.1% formic acid in water) and 10% Buffer B (methanol). Following sample injection, the column was developed at a 1 mL/min with a linear gradient of 10–50% Buffer B, over a 20-min period. Elution of pHBA glucose conjugates was monitored spectrophotometrically at 254 nm. Chemically synthesized pHBA phenolic and ester glucoside standards were used to calibrate the HPLC runs for retention times, and extinction coefficients for both compounds were accurately determined under the conditions employed. Peak areas were integrated using the software package provided with the Hewlett Packard Chemstation, and values obtained with known amounts of the chemical standards were used to quantitate micrograms of pHBA glucosides per injection. After accounting for the fraction of the original methanol extract that was injected on the column, the numbers were corrected to reflect recovery from the entire leaf sample that was extracted. This, coupled with an individual measurement of the dry weight of the leaf tissue analyzed (e.g., obtained from the same leaf, from the same plant, on the same day of analysis), enabled the quantitation of pHBA-glucosides as a percentage the total dry weight. To calculate the total amount of pHBA that was attached to glucose and express this number as a percentage of the total dry weight (i.e., "pHBA (% of dry weight)"), the phenolic and ester glucoside were added together and multiplied by 0.46. This manipulation corrects for the mass of the associated glucose moiety, 54% of the total mass of both glucose conjugates.

Analysis of Transgenic Tobacco Plants Expressing TP-CPL

As described above, TP-CPL was introduced into tobacco (*Nicotiana tabacum*) using *agrobacterium*-mediated, leaf disc transformation to determine its influence on the accumulation of pHBA glucosides. The analysis was conducted on leaf tissue that was obtained from 15 tobacco plants (primary transformants) that resulted from different transformation events. After 5 weeks in soil, the plants exhibited various levels of pHBA glucosides, ranging from 0–2.3% of the total dry weight. Phenotypic variation is typically observed in nearly all plant transformation experiments, and presumably reflects different levels of gene expression that result from so-called "positional" effects (e.g., stable integration of the trait gene at different locations in the genome) and transgene copy number. That a similar phenomenon also occurred in the present study is supported by Western blot analysis of the tobacco transformants using antisera directed against purified recombinant *E. coli* CPL. For example, although the majority of the plants (14 of 15) had immunologically detectable levels of the foreign protein, there was considerable variation in the levels of expression. Generally speaking, however, there was a positive correlation between the strength of the Western signal and the accumulation of pHBA glucosides, consistent with previous observations (Siebert et al., *Plant Physiol.*, 112:811–819 (1996)); Sommer et al., *Plant Cell Physiol.*, 39(11):1240–1244 (1998); Sommer et al., *Plant Cell Reports*, 17:891–896 (1998)). The Western blot also confirmed that the chloroplast targeting sequence is efficiently cleaved in tobacco.

The mean pHBA glucoside content (±SEM) of the 5-week-old tobacco plants was 1.12%±0.186% of dry weight. However, one of the best plants (transformant #34) had a pHBA glucoside content of 2.3% of dry weight. Like all the other transgenic tobacco plants expressing TP-CPL, the accumulation of pHBA glucosides in transformant #34 continued to increase as the plant matured. Indeed, after growing in soil for 13 weeks, the leaf content of pHBA glucosides in this particular plant reached a level of about 8% of dry weight. The latter value corresponds to a total pHBA content of ~3.7% of dry weight, after correcting for the mass of the associated glucose molecule. As described in more detail below, primary transformant #34 (CPL 34) was self-crossed and the resulting T1 seeds were used to generate a pHBA-overproducing tobacco plant for trait-stacking experiments with a pHBA 1-hydroxylase transgene. Significantly, CPL 34 resulted from a single site integration event, based on the observed segregation pattern (kanamycin resistance) of the T1 seeds from the self-crossed plant.

Generation and Analysis of Transgenic *Arabidopsis* Plants Expressing TP-CPL

The artificial fusion protein, TP-CPL, was introduced into *arabidopsis* and pHBA glucoside levels were determined. The binary vector carrying the CaMV35S-CPL expression cassette (e.g., TP-CPL-pZBL1) was transformed into *Agrobacterium tumefaciens* strain C58 C1 Rif (also known as strain GV3101), carrying the disarmed Ti (virulence) plasmid pMP90 (Koncz and Schell, *Mol. Gen. Genet.*, 204: 383–396 (1986)) by electroporation, using available protocols (Meyer et al., *Science*, 264:1452–1455 (1994)). The MP90 strain carrying the binary vector with the CPL expression construct was used to transform *Arabidopsis thaliana* plants of the ecotype Columbia with wild-type, fah1-2 (Chapple et al., *Plant Cell*, 4:1413–1424 (1992)), sng1-1 (Lorenzen et al., *Plant Physiology*, 112:1625–1630 (1996)) genetic backgrounds using a published protocol of the vacuum infiltration technique (Clough and Bent, *Plant J.*, 16(6):735–43 (1998)). Transgenic seedlings were identified under sterile conditions on standard plant growth media using kanamycin (50 µg/mL) for selection. Kanamycin resistant seedlings were transferred to soil and cultivated under a 12-hour light/12-hour dark photoperiod at 100 µE m$^{-2}$s$^{-1}$ at 18° C. (dark) and 21° C. (light) in a soil/perlite mixture. This procedure generates a population of 301 primary transformants derived from independent transformation events. Six weeks after transfer to soil, the transgenic *arabidopsis* plants were analyzed for pHBA glucosides using reverse phase HPLC as described below.

Analysis of pHBA Glucosides

Fresh cut leaf material was homogenized in 50% MeOH (5 µL per mg wet weight), and the resulting extracts were clarified by low-speed centrifugation. An aliquot of the leaf extract was then applied to a Nova-Pak C18 column (60 angstrom pore size, 4 µm particle size) using a gradient of acetonitrile (6%–48%) that contained 1.5% phosphoric acid. The pHBA phenolic and ester glucosides were detected by UV absorption at 254 nm, and quantitated using extinction coefficients that were obtained from authentic chemical standards. Of the 272 transgenic *arabidopsis* plants that were analyzed, 239 (or ~88%) contained detectable levels of both glucose conjugates, and these were present in about equal amounts. The total pHBA glucoside content of the best overproducer was 10.73% of dry weight, which is very similar to the highest levels that were observed with tobacco using the same construct. The mean value for the entire population of transgenic *arabidopsis* plants was 3.35% (+/−0.13%); the number in parenthesis is the standard error of the mean. A transgenic *arabidopsis* line (#41) was identified is this large population of transgenic lines. When assayed six weeks after germination, the T1 plant of this transformant that was hemizygous for the CPL transgene contained 7.5% DW pHBA conjugates which equals 3.42% DW free pHBA. T2 progeny of this line segregated 3:1 for the kanamycin resistance gene indicating that this transgenic line carried a T-DNA insert a single genetic locus. Seed were harvested from individual T2 progeny. T3 seed batches derived from T2 plants that were homozygous for the T-DNA insertion were identified. These T3 seed batches no longer segregated kanamycin-sensitive progeny when germinated on media containing kanamycin. Homozygous progeny of this transgenic line contained 2.6% pHBA DW in leaf tissue when grown under the controlled conditions described above for eight weeks.

Example 5

Utility of the pHBA 1-hydroxylase Gene for Production of Hydroquinone Glucosides in Transgenic Plants Production of Hydroguinone Glucoside (Arbutin) in *arabidopsis*

To generate a construct for constitutive expression of the pHBA 1-hydroxylase in plants, a 1482 bp XbaI/HindlII DNA fragment, containing the full-length pHBA 1-hydroxylase ORF (SEQ ID NO:26) and 42 bp of 5' untranslated DNA (derived from the pET29A vector) immediately upstream of the initiation codon, was excised from the pET29a construct used for recombinant enzyme production and cloned into the binary vector pBE856 (SCP1-FlpM) with XbaI and HpaI. The insert DNA used in the ligation reaction was generated by HindIII digestion of the plasmid DNA. Linearized plasmid DNA was purified and overhanging DNA ends were filled in with T4 DNA polymerase (New England Biolabs, MA, USA) according to instructions of the manufacturer. The blunted plasmid DNA was digested with XbaI and ligated to the XbaI HpaI digested pBE856 DNA. This resulted in replacement of the FlpM recombinase ORF in pBE856 with the pHBA 1-hydroxylase ORF, situated between the constitutive SCP1 promoter and 3' untranslated region of the potato proteinase inhibitor II (PIN II) gene. The resulting binary vector, pHBA 1-hydroxylase expression construct ("pBE856 (SCP1-pHBA 1H)"), was used for plant transformation as described below.

Plasmid pBE856 (SCP-FlpM) was previously constructed by cloning a 2172 bp XbaI-EcoRI fragment containing a chimeric SCP1:FlpM:3' Pin gene into the multiple cloning site of the binary vector pBE673 (described below), after cleaving the latter with XbaI and EcoRI. The SCP1:FlpM: Pin gene is comprised of a synthetic 35S promoter (SCP1) (Bowen et al., U.S. Application No. 60/72050 (Jun. 6, 2000), Cont.-in-part of U.S. Ser. No. 661,601, abandoned), fused at its 3' end to the ORF of the FlpM recombinase, fused at its 3' end to the 3' PIN region derived from the *Solanum tuberosum* proteinase inhibitor II gene (GenBank® Accession No. L37519). Plasmid pBE673 was derived from pBin 19 (GenBank® Accession No. U09365) by replacing an 1836 bp Bsu36a-Cla I fragment of pBin19, which contains the 3' end of the nopaline synthase (nos) promoter, the npt II (kanamycin resistance) ORF, and the 3' nos region, with a 949 bp Bsu36I-Cla I fragment that contains (5' to 3'): a 106 bp fragment comprising the 3' end of nos promoter (nucleotides 468–574 described in GenBank® Accession Nos. V00087 and J01541; see also Bevan et al., *Nucleic Acids Res.*, 11 (2), 369–385 (1983)), a 5 bp GATCC sequence, a 551 bp fragment corresponding to the *Streptomyces hygroscopicus* phosphothricin acetyl transferase (basta resistance) ORF (GenBank® Accession No. X17220) except that the termination codon was changed from TGA to TAG, an 8 bp TCCGTACC sequence, and a 279 bp 3' nos region (nucleotides 1824–2102 of GenBank® Accession Nos. V00087 and J01541 described above).

The pBE856 SCP1-pHBA 1H plasmid was introduced into *Agrobacterium tumefaciens* C58 MP90 by electroporation. Briefly, 1 μg plasmid DNA was mixed with 100 μL of electro-competent cells on ice. The cell suspension was transferred to a 100 μL electroporation cuvette (1 mm gap width) and electroporated using a BIORAD electroporator set to 1 kV, 400Ω and 25 μF. Cells were transferred to 1 mL LB medium and incubated for 2 h at 30° C. Cells were plated onto LB medium containing 50 μg/mL kanamycin and 10 μg/mL rifampicin. Plates were incubated at 30° C. for 60 h. Recombinant *agrobacterium* cultures (500 mL LB, 50 μg/mL kanamycin and 10 μg/mL rifampicin) were inoculated from single colonies of transformed *agrobacterium* cells and grown at 30° C. for 60 h. Cells were harvested by centrifugation (5000×g, 10 min) and resuspended in 1 L of 5% (W/V) sucrose containing 0.05% (V/V) Silwet.

*Arabidopsis* plants (line #41), homozygous for the CaMV 35S CPL transgene (described above), were grown in soil at a density of 30 plants per 100 cm$^2$ pot in metromix 360 soil mixture for 4 weeks (22° C., 16 h light/8 h dark, 100 μE m$^{-2}$s$^{-1}$). Plants were repeatedly dipped into the *agrobacterium* suspension and kept in a dark, high humidity environment for 24 h. Plants were grown for 3 to 4 weeks under standard plant growth conditions described above and plant material was harvested and dried for one week at ambient temperatures in paper bags. Seeds were harvested using a 0.425 mm mesh brass sieve. Cleaned *arabidopsis* seeds (1.5 g, corresponding to about 75000 seeds) were sterilized by washes in 45 mL of 80% ethanol, 0.01% triton X-100, followed by 45 mL of 30% (V/V) household bleach in water, 0.01% triton X-100 and finally by repeated rinsing in sterile water. Aliquots of 7500 seeds were transferred to 13 mm Ø Petri dishes containing sterile plant growth medium comprised of 0.5×MS salts, 1.5% (W/V) sucrose, 0:05 MES/ KOH (pH 5.8), 200 μg/mL timentin, and 10 μg/mL phosphinotricine solidified with 10 g/L agar. Homogeneous dispersion of the seed on the medium was facilitated by mixing the aqueous seed suspension with a equal volume of melted plant growth medium. Plates were incubated under standard growth conditions for 10 d. Phosphinotricine-resistant seedlings were transferred to plant growth medium without phosphinotricine and grown for 18 d.

Determination of Arbutin Levels in Transgenic *arabidopsis* Plants

Leaf tissue (4–15 mg) was excised and transferred to 1.5 mL screw-cap tubes (Sarstedt Inc., Newton, N.C.). Water (200 μL) was added to each leaf sample and small molecules were extracted by incubation at 100° C. for 1 h. The leaf extracts were clarified by centrifugation (13000×g, 10 min) and analyzed by HPLC as follows. Reaction products (10 μL) were injected onto a Nova Pak C8 column (3.9×150 mm, 60 Å, 4 μm). The column was developed at a flow-rate of 1 mL/min under the following conditions: Solvent A (H$_2$O,/1.5% HPO$_4$), Solvent B (100% MeOH/H$_2$O/1.5% HPO$_4$); 0–5 min 0% B, 5–20 min 0–100% B, 20–21 min 100–0% B, 21–25 min 0% B. Hydroquinone glucoside (arbutin) was detected at λ=282 nm and hydroquinone at λ=288 nm. Arbutin was detected in the aqueous extracts of plants co-expressing CPL and pHBA 1-hydroxylase genes based on retention time and UV absorption spectrum that was indistinguishable from that of chemically-synthesized, authentic arbutin (hydroquinone β-D-glucopyranoside) obtained from Sigma. No free hydroquinone was detectable in the aqueous extracts of plants expressing CPL and the pHBA 1-hydroxylase genes (FIG. 4).

The identity of arbutin detected in these plant extracts was confirmed by liquid chromatography coupled to mass-spectroscopy (LC/MS). Briefly, 40 μL of plant extract were injected onto a ZORBAX Eclipse XDB-C18 column (2.1× 150 mm, 80 Å, 3.5 μm) (Agilent, CA, USA). The column was developed under the following conditions: Solvent A ($H_2O$/0.1% (v/v) formic acid), Solvent B (100% acetonitrile); 0–25 min 0%–60% B (0.3 mL/min), 25–25.5 min 60–100% B (0.4 mL/min), 25.5–30 min 100% B (0.4 mL/min), 30–31 min 100%–0% B (0.3 mL/min), 31–40 min 0% B (0.3 mL/min). A Hewlett-Packard mass spectrometer MSD1100 (Agilent, Wilmington, Del.) equipped with a electrospray interface was used to detect analytes. Data was acquired in positive ion mode with a capillary voltage of 3 kV. The desolvation gas flow was 12 L/min of nitrogen. The desolvation and the source block temperatures were 350° C. The instrument was tuned for unit resolution. Data was collected by scanning from 80–600 daltons in 1 sec for MS experiments. The aqueous extract of transgenic *arabidopsis* plants expressing both CPL and pHBA 1-hydroxylase contained a new compound that when analyzed by mass spectroscopy produced molecular ions in electrospray positive ionization mode that exhibited mass to charge ratios (m/z+) of 310.9 and 290.0. The properties of these molecular ions are in very close agreement with the expected m/z+ of the potassium adduct (MW 311.35) and ammonium adduct (MW 290.29), respectively of hydroquinone glucoside (MW 272.25). Moreover, the compound consistently produced a fragment of m/z+=180 which is in close agreement with the expected m/z+ for glucose (MW=180.16).

Arbutin concentration in tissue of plants expressing CPL and pHBA 1-hydroxylase genes was determined by HPLC analysis using calibration curves established with standards of known concentrations of chemically-synthesized arbutin (Sigma). Table 1 shows arbutin concentrations in a population of T1 plants expressing different levels of pHBA 1-hydroxylase enzyme. Table shows that, with co-expression of CPL and pHBA 1-hydroxylase genes in *arabidopsis* plant tissue, levels of arbutin production of up to 5.28 mg/g fresh weight can be attained after only 28 d of plant growth.

TABLE 1

Arbutin concentration in leaf tissue of arabidopsis plants co-expressing CPL and pHBA 1-hydroxylase genes.

| Plant id Line | Arbutin (mg/g FW) | Plant id Line | Arbutin (mg/g FW) |
|---|---|---|---|
| 66 | 5.28 | 33 | 1.12 |
| 16 | 3.62 | 20 | 1.06 |
| 53 | 3.14 | 91 | 1.02 |
| 76 | 2.62 | 68 | 1.00 |
| 31 | 2.59 | 48 | 1.00 |
| 70 | 2.57 | 82 | 1.00 |
| 88 | 2.44 | 12 | 0.99 |
| 32 | 2.35 | 25 | 0.97 |
| 8 | 2.33 | 64 | 0.96 |
| 14 | 2.31 | 11 | 0.94 |
| 4 | 2.27 | 84 | 0.94 |
| 6 | 2.10 | 42 | 0.93 |
| 34 | 2.07 | 19 | 0.92 |
| 40 | 1.91 | 29 | 0.87 |
| 1 | 1.85 | 46 | 0.87 |
| 37 | 1.82 | 35 | 0.86 |
| 93 | 1.72 | 62 | 0.83 |
| 72 | 1.68 | 36 | 0.82 |
| 45 | 1.67 | 73 | 0.80 |
| 18 | 1.66 | 52 | 0.79 |
| 15 | 1.63 | 9 | 0.78 |
| 13 | 1.63 | 55 | 0.77 |
| 63 | 1.58 | 67 | 0.76 |
| 47 | 1.55 | 71 | 0.76 |
| 56 | 1.52 | 39 | 0.75 |
| 41 | 1.52 | 89 | 0.75 |
| 85 | 1.52 | 24 | 0.73 |
| 86 | 1.49 | 58 | 0.73 |
| 61 | 1.48 | 28 | 0.72 |
| 83 | 1.48 | 17 | 0.70 |
| 80 | 1.47 | 65 | 0.66 |
| 26 | 1.44 | 21 | 0.64 |
| 78 | 1.41 | 57 | 0.63 |
| 50 | 1.39 | 3 | 0.63 |
| 87 | 1.37 | 54 | 0.62 |
| 23 | 1.37 | 5 | 0.58 |
| 27 | 1.36 | 60 | 0.55 |
| 74 | 1.36 | 10 | 0.53 |
| 30 | 1.30 | 51 | 0.44 |
| 79 | 1.29 | 38 | 0.37 |
| 22 | 1.29 | 44 | 0.37 |
| 2 | 1.22 | 59 | 0.30 |
| 49 | 1.20 | 7 | 0.00 |
| 81 | 1.17 | 69 | 0.00 |
| 92 | 1.17 | 75 | 0.00 |
| 43 | 1.14 | 77 | 0.00 |

Transgenic *arabidopsis* lines producing high levels of hydroquinone glucoside (line #s 32, 31, 16, 14) and control line #69 (showing no accumulation of hydroquinone glucoside) were transferred to soil and grown for eight weeks at 21° C., 60% relative humidity, and a 14 h light/10 h darkness cycle. Hydroquinone and pHBA levels in leaf tissue were determined. A single leaf was transferred to a 1.5 mL screw cap polypropylene tube and supplemented with 500 µl of 1 M HCl. The tissue was hydrolyzed by incubation of the sealed polypropylene tube in a heating block set to 100° C. for 1 h. The tissue hydrolysate was supplemented with 100 µL of 1 M potassium phosphate buffer (pH 6.5) and 430 µL of 1.1 N NaOH was added. Neutral pH of the neutralized tissue hydrolysate was confirmed by pH indicator paper. The leaf homogenate was cleared by centrifugation. Ten µl of the cleared tissue hydrolysate was analyzed by HPLC on a Nova-Pak® C18 column (60 Å pore size, 4 µM particle size) (Waters, USA) using a linear gradient from 1.5% phosphoric acid (solvent A) to 50% MeOH, 1.5% phosphoric acid (solvent B) and UV detection at 254 nm for detection of pHBA and 289 nm for detection of hydroquinone. The following solvent gradient was applied: 0–5 min 100% solvent A; 20 min 100% solvent B; 21–25 min 100% solvent A. Hydroquinone and pHBA were quantitated using standard curves generated with commercially available pHBA and hydroquinone (Sigma).

Table 2 summarizes the pHBA and hydroquinone levels in *arabidopsis* lines expressing CPL and pHBA 1-hydroxylase. The data indicate that *arabidopsis* plants expressing CPL and pHBA 1-hydroxylase continue to synthesize hydroquinone from pHBA after transfer to soil. In some *arabidopsis* lines more than 60% of the pHBA produced by CPL is converted to hydroquinone. Taking into consideration the difference in molecular weight between hydroquinone (110.1) and arbutin (272.1), arbutin levels in soil-grown *arabidopsis* plants expressing CPL and pHBA 1-hydroxylase reach 4% dry weight (DW).

TABLE 2

| Line | pHBA (µmol/g FW) | Hydroquinone (µmol/g FW) | Total pHBA (µmol/g FW) | % conversion pHBA→HQ | Hydroquinone % DW |
|---|---|---|---|---|---|
| 32 | 8.25 | 14.8 | 23.05 | 64.2 | 1.62 |
| 31 | 15.82 | 12.72 | 28.54 | 44.6 | 1.4 |
| 16 | 8.37 | 8.31 | 16.68 | 49.8 | 0.92 |

TABLE 2-continued

| Line | pHBA (μmol/g FW) | Hydro-quinone (μmol/g FW) | Total pHBA (μmol/g FW) | % conversion pHBA→HQ | Hydro-quinone % DW |
|---|---|---|---|---|---|
| 14 | 17.47 | 5.88 | 23.35 | 25.2 | 0.65 |
| 69 | 18.23 | 0 | 18.23 | 0 | 0 |

Production of Hydroquinone Glucoside (Arbutin) in Tobacco

T1 seeds from transgenic tobacco line #34 (CPL 34), harboring the TP-CPL expression construct, were surface-sterilized, germinated, and grown under sterile conditions on MS media that contained kanamycin (0.2 mg/mL). Plants regenerated from stem explants containing two vegetative nodes were grown in Magenta boxes on MS media that contained kanamycin (0.05 mg/mL) and Timentin™ (0.1 mg/mL) (GlaxoSmithKline, Research Triangle Part, N.C.). The plants were grown for 4 weeks in a temperature and light regulated growth chamber set to cycles of 16 h, 23° C. day/8 h, 21° C. night.

A 50-mL culture of the *Agrobacterium tumefaciens* strain harboring pBE856 (SCP1::pHBA 1H) was grown in LB media for 36 hours at 30° C. The cells were harvested by centrifugation (7000×g), washed twice with 50 mL sterile MS medium, and finally resuspended in 40 mL of the same solution. Leaves from one of the regenerated TP-CPL tobacco plants described above were harvested under sterile conditions, cut into pieces of approximately 1.5 $cm^2$, and incubated in the *agrobacterium* suspension for 30 min. at room temperature. Leaf explants were placed adaxial side down on shoot induction plates (Murashige's Minimal Organics Medium, 3% sucrose, 1 mg/L benzyl aminopurine, 0.1 mg/L naphthaleneacetic acid, and 0.8% agar) and incubated at room temperature for three days. Leaf explants were transferred to shoot induction media containing 5 mg/L glufosinate-ammonium (Fluka/Sigma Aldrich, St. Louis, Mo.), 25 mg/L kanamycin, and 100 mg/L Timentin™ (GlaxoSmithKline) and subcultured to new media every three weeks. Plates were placed in growth chambers set to cycles of 16 h, 23° C. day/8 h, 21° C. night. Excisable shoots were transferred to root induction media (Murashige's Minimal Organics Medium, 1% sucrose, and 0.8% agar). Rooted shoots were eventually transferred to soil, and the resulting plants were grown in a greenhouse.

Determination of Arbutin Levels in Transgenic Tobacco Plants

Leaf tissue (10–50 mg) was excised from plantlets grown under sterile conditions on root induction medium for 21 d. Tissue was transferred to 1.5 mL screw-cap tubes (Sarstedt Inc., Newton, N.C.). Water (400 μL) was added to each leaf sample and small molecules were extracted by incubation at 100° C. for 1 h. The leaf extracts were clarified by centrifugation (13000×g, 10 min) and analyzed by HPLC as follows. Reaction products (10 μL) were injected onto a Nova Pak C8 column (3.9×150 mm, 60 Å, 4 μm). The column was developed at a flow-rate of 1 mL/min under the following conditions: Solvent A ($H_2O$/1.5% $HPO_4$), Solvent B (100% MeOH/$H_2O$/1.5% $HPO_4$); 0–5 min 0% B, 5–20 min 0–100% B, 20–21 min 100% B–0% B, and 21–25 min 0% B. Hydroquinone glucoside (arbutin) was detected at λ=282 nm and hydroquinone at λ=288 nm.

Arbutin was detected in the aqueous extracts of plants co-expressing CPL and pHBA 1-hydroxylase genes based on retention time and UV absorption spectrum that was indistinguishable from that of chemically-synthesized, authentic arbutin obtained from Sigma (FIG. 4). Moreover, the identity of arbutin detected in these plant extracts was confirmed by liquid chromatography coupled to mass-spectroscopy (LC/MS). Forty μL of plant extract was injected onto a ZORBAX Eclipse XDB-C18 column (2.1×150 mm, 80 Å, 3.5 μm) (Bio-RAD, USA). The column was developed under the following conditions: Solvent A ($H_2O$/0.1% (v/v) formic acid), Solvent B (100% acetonitrile); 0–25 min 0%–60% B (0.3 mL/min), 25–25.5 min 60–100% B (0.4 mL/min), 25.5–30 min 100% B (0.4 mL/min), 30–31 min 100%–0% B (0.3 mL/min), and 31–40 min 0% B (0.3 mL/min). A Hewlett-Packard mass spectrometer MSD1100 equipped with a electrospray interface was used to detect analytes. Data was acquired in positive ion mode with a capillary voltage of 3 kV. The desolvation gas flow was 12 L/min of nitrogen. The desolvation and the source block temperatures were 350° C. The instrument was tuned for unit resolution. Data was collected by scanning from 80–600 daltons in 1 sec for MS experiments.

The aqueous extract of transgenic *arabidopsis* plants expressing both CPL and pHBA 1-hydroxylase contained a new compound. When analyzed by mass spectroscopy molecular ions in electrospray positive ionization mode were produced that exhibited mass to charge ratios (m/z+) of 311.0 and 290.0. The properties of these molecular ions are in very close agreement with the expected m/z+of the potassium adduct (MW 311.35) and ammonium adduct (MW 290.29), respectively of hydroquinone glucoside (MW 272.25). Moreover, the compound consistently produced a fragment of m/z+=180.0 which is in close agreement with the expected m/z+ for glucose (MW=180.16).

Arbutin concentration in tissue of plant expressing CPL and pHBA 1-hydroxylase genes was determined by HPLC analysis using calibration curves established with standards of known concentrations of chemically-synthesized arbutin. Table 3 shows arbutin concentrations in a population of T1 plants expressing different levels of pHBA 1-hydroxylase enzyme. This table shows that co-expression of CPL and pHBA 1-hydroxylase genes in tobacco plant tissues can produce levels of arbutin as high as 5.29 mg/g fresh weight after only 21 d of plant growth (FIG. 4).

TABLE 3

Arbutin concentration in leaf tissue of tobacco plants co-expressing CPL and pHBA 1-hydroxylase genes.

| Plant Line # | Arbutin (mg/g FW) |
|---|---|
| 13 | 5.29 |
| 11 | 4.66 |
| 42 | 4.38 |
| 8 | 4.26 |
| 24 | 4.18 |
| 45 | 4.17 |
| 20 | 4.10 |
| 19 | 4.03 |
| 10 | 3.25 |
| 27 | 3.07 |
| 44 | 2.93 |
| 6 | 2.77 |
| 43 | 2.62 |
| 35 | 2.59 |
| 9 | 2.50 |
| 14 | 2.37 |
| 26 | 2.32 |
| 33 | 2.27 |
| 34 | 2.25 |
| 32 | 2.22 |
| 29 | 2.20 |

TABLE 3-continued

Arbutin concentration in leaf tissue of tobacco plants co-expressing CPL and pHBA 1-hydroxylase genes.

| Plant Line # | Arbutin (mg/g FW) |
|---|---|
| 25 | 2.13 |
| 1 | 2.04 |
| 30 | 2.02 |
| 4 | 1.90 |
| 31 | 1.71 |
| 22 | 1.71 |
| 40 | 1.69 |
| 37 | 1.62 |
| 17 | 1.59 |
| 2 | 1.39 |
| 36 | 1.37 |
| 41 | 1.34 |
| 16 | 1.32 |
| 21 | 1.28 |
| 18 | 1.21 |
| 3 | 0.96 |
| 5 | 0.85 |
| 28 | 0.79 |
| 38 | 0.59 |
| 7 | 0.00 |
| 12 | 0.00 |
| 15 | 0.00 |
| 23 | 0.00 |
| 39 | 0.00 |

Transgenic tobacco lines producing high levels of hydroquinone glucoside (line #s 13, 11, 42, 8, 24, 45, 19, 10, 27, 44, 6, 43, 35, 9, and 14) and control line 34 (CPL 34, devoid of the pHBA 1-hydroxylase gene) were transferred to soil and grown for 77 d under greenhouse conditions. Hydroquinone and pHBA levels in leaf tissue of tobacco lines grown in soil were determined follows. Four leaf discs (1 cm diameter) were harvested from a mature leaf of each transgenic line using a conventional cork borer. The weight of three leaf discs was determined immediately after harvesting and again after drying the tissue samples at 65° C. for 24 h. The fourth leaf disc was transferred to a 1.5 mL screw cap polypropylene tube and supplemented with 500 µl of 1 M HCl. The tissue was hydrolyzed by incubation of the sealed polypropylene tube in a heating block set to 100° C. for 1 h. The tissue hydrolysate was supplemented with 100 µL of 1M potassium phosphate buffer (pH 6.5) and 430 µL of 1.1 N NaOH. Neutral pH of the neutralized tissue hydrolysate was confirmed using pH indicator paper (VWR, USA). The leaf homogenate was cleared by centrifugation and diluted 5-fold with water. Ten µL of the diluted tissue hydrolysate was analyzed by HPLC on a Nova-Pak® C18 column (60 Å pore size, 4 µM particle size) using a linear gradient from 1.5% phosphoric acid (solvent A) to 50% MeOH, 1.5% phosphoric acid (solvent B) and UV detection at 254 nm for detection of pHBA and 289 nm for detection of hydroquinone. The following solvent gradient was applied: 0–5 min 100% solvent A; 20 min 100% solvent B; 21–25 min 100% solvent A. Hydroquinone and pHBA were quantitated using standard curves generated with commercially available pHBA and hydroquinone.

Table 4 summarizes pHBA and hydroquinone levels in tobacco lines expressing CPL and pHBA 1-hydroxylase. The Table shows that tobacco plants expressing CPL and pHBA 1-hydroxylase continue to synthesize hydroquinone from pHBA after transfer to soil. In some tobacco lines more than 95% of the pHBA produced by CPL is converted to hydroquinone. Taking into consideration the difference in molecular weight between hydroquinone (110.1) and arbutin (272.251) and the fact that no free, unconjugated hydroquinone was detected by HPLC analysis of untreated tissue extracts of transgenic lines, arbutin levels in soil-grown tobacco plants expressing CPL and pHBA 1-hydroxylase reached 24.9% DW after 77 d of growth under greenhouse conditions.

TABLE 4

| Line | pHBA (µmol g$^{-1}$ FW) | Hydroquinone (µmol g$^{-1}$ FW) | Total pHBA (µmol g$^{-1}$ FW) | % conversion pHBA→HQ | hydroquinone % DW |
|---|---|---|---|---|---|
| 13 | 7.16 | 80.82 | 87.97 | 91.9 | 5.31 |
| 11 | 6.35 | 128.16 | 134.51 | 95.3 | 5.45 |
| 42 | 12.58 | 105.78 | 118.36 | 89.4 | 7.44 |
| 8 | 25.70 | 18.59 | 44.30 | 42.0 | 1.70 |
| 24 | 9.87 | 99.27 | 109.15 | 91.0 | 8.25 |
| 45 | 10.22 | 85.45 | 95.66 | 89.3 | 6.28 |
| 19 | 4.49 | 87.00 | 91.49 | 95.1 | 5.85 |
| 10 | 13.59 | 71.09 | 84.67 | 84.0 | 5.97 |
| 27 | 11.29 | 100.89 | 112.18 | 89.9 | 10.06 |
| 44 | 28.75 | 11.25 | 40.00 | 28.1 | 1.26 |
| 6 | 7.05 | 105.66 | 112.71 | 93.7 | 8.08 |
| 43 | 6.89 | 82.84 | 89.73 | 92.3 | 7.02 |
| 35 | 3.86 | 57.92 | 61.78 | 93.8 | 5.67 |
| 9 | 17.13 | 17.20 | 34.33 | 50.1 | 2.13 |
| 14 | 20.74 | 27.62 | 48.36 | 57.1 | 2.90 |
| Cont 34 | 46.72 | 0.00 | 46.72 | 0.0 | 0.00 |

Example 6

Expression Cloning and Biochemical Characterization of a Glucosyl Transferase Enzyme that Efficiently Glucosylates Hydroquinone to form Arbutin Analysis of Applicants' databases of expressed sequence tags ESTs) of *Arabidopsis thaliana* indicate that this plant constitutively expresses a glucosyltransferase gene (UGT72B1) encoding a polypeptide that shows 62% sequence identity to the arbutin synthase protein of *Rauwolfia serpentine* (Arend et al., *Phytochemistry*, 53:187–193 (2000): Hefner et al., *Bioorg. Med. Chem.*, 10:1731–1741 (2002)). The enzyme had previously been produced recombinantly in *E. coli* and its activity with benzoic acid derivatives has been described (Lim et al., *J. Biol. Chem.*, 277(1): 586–592 (2002): WO 02/103022 A2). Of the benzoic acid derivatives analyzed in this study, the UGT72B1 enzyme showed the highest specific activity with 2,5-dihydroxybenzoic acid. The specific activity of the enzyme with this substrate (11.72 pkat/µg protein) translates to a turnover number of ~0.6/sec at 30° C. The biochemical function of this protein (specifically its activity with other substrates) was unknown prior to the instant disclosure (Hefner et al., supra). The TBLASTN algorithm was used to search Applicants database of *arabidopsis* EST sequences using the published sequence of the UGT72B1 enzyme (GenBank® Accession No. 116337.1). An EST clone containing sequence corresponding 5' end of the UGT72B1 transcript was identified.

Expression Cloning of *Arabidopsis* GT72B1

The flanking regions of the ORF of the UGT72B1 were modified by PCR for insertion into the high-level *E. coli* expression vector, pET28a(+) (Novagen). This insertion was accomplished using primers 17 and 18 and purified plasmid DNA from the original cDNA clone as the target for amplification.

Primer 17 - (SEQ ID NO:39)
5'-GAATATTTGCATccatggAGGAATCC-3'

Primer 18 - (SEQ ID NO:40)
5'-GAACATCgtcgacTTAGTGGTTGC-3'

The underlined bases hybridize to the target gene, while lower case letters indicate the restriction sites (NcoI or SalI) that were added to the ends of the PCR primers. Primer 17 hybridizes at the start of the gene and introduces an NcoI site at the initiation codon, while Primer 18 hybridizes at the opposite end and provides a SalI site just after the stop codon; neither primer alters the deduced amino acid sequence of the ORF of the UGT72B1 gene. The PCR reaction contained 50 mm KCl, 10 mM Tris-HCl (pH 9), 0.1% Triton X-100, 2.5 mM $MgCl_2$, 0.2 mM each dNTP, 5 units of Taq® polymerase (MBI Fermentas), 10 ng of the cDNA plasmid template, and both PCR primers at a final concentration of 0.2 μM. Amplification was carried out for 25 cycles, each cycle comprising 1.5 min at 94° C., 1.5 min at 55° C., and 2.5 min at 72° C. The PCR product was digested with NcoI and SalI, gel-purified, and the resulting fragment was ligated into the *E. coli* expression vector, pET-28a(+) (Novagen) that was digested with the same restriction enzymes. The ligation reaction mixture was used to transform *E. coli* DH10B, and plasmid DNA from a representative colony was sequenced completely to check for PCR errors; none were found. The plasmid selected for further manipulation is referred to below as "pET28a/UGT72B1". Sequence of UGT72B1 open reading frame and deduced amino acid sequence of the enzyme are set forth as SEQ ID NO:41 and SEQ ID NO:42, respectively.

pET28a/UGT72B1 was introduced into *E. coli* BL21DE3 cells by electroporation. Recombinant clones were grown on LB media in the presence of 50 mg $l^{-1}$ kanamycin.

Recombinant Production of UGT72B1 in *E. coli*

A 10L fermentor run (Braun Instruments, BiostatC 15L fermentor, Allentown, Pa.) was conducted to produce sufficient *E. coli* cell mass to purify the recombinantly produced UGT72B1 protein. 9.5 L of *E. coli* growth medium with a composition described below was inoculated with a seed culture (500 mL LB 50 mg/L kanamycin) of *E. coli* BL21DE3 cells harboring the pET28a/UGT72B1 construct. The seed culture was grown at 35° C. for ~10 h to an $OD_{550\ nm}$ of 3.

Fermentor Medium Composition (per L):
$NaH_2PO_4*2H_2O$ 0.9 g
$Na_3Citrate*2H_2O$ 0.05 g
$MgSO_4$ 0.45 g
$K_2HPO_4$ 1.95 g
$NH_4SO_4$ 0.3 g
Casamino acids 20 g
Thiamine HCl 0.06 mg
$FeSO_4*7H_2O$ 0.03 g
Trace elements IL2 1 mL Composition of IL2 Trace Element Stock Solution (per L):

| | |
|---|---|
| $ZnSO_4*7H_2O$ | 8 g |
| $CuSO_4*5H_2O$ | 3 g |
| $MnSO_4*H_2O$ | 2.5 g |
| $H_3BO_3$ | 0.15 g |
| $NH_4molybdate*4H_2O$ | 0.1 g |

| | |
|---|---|
| $CoCl_2*6H_2O$ | 0.06 g |
| Polypropylene glycol | 0.83 mL |

After sterilization of the medium the following components were added from sterile stock solutions to the indicated final concentrations:
Biotin 0.005 g/L
$CaCl_2 \times 2H_2O$ 0.026 g/L
Glucose 20 g/L
Kanamycin 0.050 g/L The following set-points were used during the fermentation run.
Stirring: 375 rpm
Airflow: 6 slpm (standard liters per minute)
Temperature: 17° C.
$CO_2$: 10%, cascade stirrer then air flow
Pressure: 0.5 bar
pH: 6.8

The culture was grown for about 25 h to an $OD_{600\ nm}$ of 15. Subsequently IPTG was added from a sterile stock solution to a final concentration of 0.4 mM and fermentation was continued for another 24 h. Cell paste was harvested and stored at −80° C.

Large Scale Purification of the Recombinantly Produced UGT72B1 Enzyme

Cell paste obtained as described above (50 g wet weight) was resuspended in 95 mL ice-cold 100 mM Tris-HCl (pH 7.5), 5 mM $MgSO_4$, 1 mM dithiothreitol, 0.03 mg/mL DNAse I, and 0.5 mM phenylmethanesulfonyl fluoride and passed twice through a French pressure cell at 20,000 psi. Unless otherwise noted, subsequent steps were at 0–4° C. Cell debris was removed by centrifugation (43,000×g, 90 min), and the resulting cell-free extract (~110 mL), containing ~40 mg of protein per mL, was supplemented with glycerol (5%) and stored at −80° C. for subsequent purification.

The first step in the purification of UGT72B1 was anion exchange chromatography. The crude extract (12.5 mL) was buffer-exchanged in 2.5 mL aliquots on PD-10 columns into Q buffer (50 mM Tris-HCl (pH 7.7), 10 mM sodium sulfite, and 1 mM EDTA) and filtered through a 0.2 μm Acrodisc filter (Gelman-Pall Life Sciences). The entire sample (17.5 mL) was then applied to a Mono Q HR 16/10 column (Amersham Biosciences) that was pre-equilibrated at 25° C. with Buffer Q. The column was developed at 4 mL/min with Buffer Q for the first 20 min, and this was followed by a linear gradient (140 mL) of 0–250 mM NaCl (in Buffer Q). Fractions (8 mL) were collected from the start of the gradient. Aliquots (10 μL) of each column fraction were tested for UDP-glucosyltransferase activity using p-nitrophenol (pNP) (Sigma) as a substrate. The basis of this assay is the disappearance of yellow color when glucose is attached to the phenolic hydroxyl group of pNP. The 100-μL reactions, which were performed at room temperature, contained 40 mM Tris-HCl (pH 7.5), 240 mM NaCl, 0.8 mM $MgCl_2$, 10 mM UDP-glucose, and 148 μM pNP. Based on the visual assay, virtually all of the recombinant protein was detected in Fraction 8.

At the end of the gradient, the column was extensively washed with 1 M NaCl (in Buffer Q) and the initial conditions were reestablished. The active fraction was supplemented with 100 mM sodium phosphate buffer (pH 6.34), 10 mM dithiothreitol, and 5% glycerol, and kept on ice while five more 12.5-mL aliquots of the cell-free extract were processed in an identical manner. The active fractions from all six runs were combined and stored at −80° C. for subsequent processing.

In the next step, the pooled fractions (60 mL total volume) were subjected to size exclusion chromatography. The entire sample was concentrated to a final volume of 6 mL using four Centripep-30 devices (Millipore Corp.), filtered through a 0.2 µm Acrodisc filter, and was then fractionated on a TSK-Gel® G3000SW gel filtration column (21×600 mm) (Tosoh Biosep LLC., Montgomeryville, Pa.) in 2-mL aliquots. The column was developed at 4 mL/min with 50 mM Tris-HCl (pH 7.2), 330 mM NaCl, 1 mM dithiothreitol, 0.5 mM EDTA (25° C.). The material eluting between 32.5 and 34.4 min (corresponding to the peak of UDP-glucosyl-transferase activity with pNP as substrate) was collected and supplemented with 5.8% glycerol. This procedure was repeated two more times, consuming the entire sample. The active fractions from all three-gel filtration columns were combined and supplemented with an additional 4.85 mM dithiothreitol for further processing.

The UGT72B1 enzyme was further purified by chromatography on hydroxylapatite. Briefly, the material described above was concentrated to 3 mL in a Centripep-30 and filtered through a 0.2 µm Acrodisc filter. One quarter of the concentrated material (0.75 mL) was diluted with 10 mL of Buffer h (10 mM sodium phosphate (pH 6.34), 0.5 mM DTT, and 0.01 mM $CaCl_2$). The entire sample was then injected onto a 100×7.8 mm Bio-Gel HPHT hydroxylapatite column, pre-equilibrated with Buffer H. The column was developed at 1 mL/min (25° C.) with Buffer h for the first 12 min, and this was followed by a linear gradient (25 mL) of 10–350 mM sodium phosphate (in Buffer H). Fractions eluting between ~109 and 160 mM sodium phosphate were pooled, supplemented with 6.52% glycerol and 10 mM dithiothreitol, and frozen on dry ice while the remainder of the sample was processed in an identical manner in three identical runs consuming the entire sample. The pooled fractions from all four runs were combined to yield a total volume of 14 mL and this material was frozen at −80° C. Prior to enzyme assays described below the UGT72B1 enzyme preparation was further concentrated. Seven milliliters of the pooled hydroxylapatite material described above was buffer-exchanged into 50 mM Tris HCL (pH 7.0) and 1 mM DTT using three PD-10 columns. The PD eluents were combined and concentrated to 1.1 mL using a Centripep-30 device. The final protein concentration of the UGT72B1 protein in the concentrated sample was 14.64 mg/mL. Protein concentration was determined spectrophotometrically using an extinction coefficient at 280 nm of 50,250 $M^{-1}$ (as calculated by the Peptidesort program of GCG using SEQ ID NO:42). Visual inspection of overloaded Coomassie-stained gels indicated that the purified recombinant UGT72B1 protein was at least 95% pure.

Analysis of Kinetic Properties of UGT72B1 with Hydroquinone

Kinetic properties of UGT72B1 with the substrate hydroquinone were determined. The enzyme was diluted to a final concentration of 0.115 ng/µL using 50 mM Tris HCl (pH 7.5), 1 mM $MgCl_2$ and 2 mM DTT. Hydroquinone UDP-glucosyltransferase (HQ-GT) activity was assayed using 5 µL (0.57 ng) of UGT72B1 in a final volume of 25 µL in the presence of 50 mM Tris HCl, 1 mM $MgCl_2$ 1 mM DTT, 20 mM UDPG, and hydroquinone ranging from 4 mM to 7.8 µM for 5 min at 37° C. Arbutin formation was quantitated by HPLC analysis as follows: 10 µL of analyte were separated on a Nova-Pak® C18 column (60 Å pore size, 4 µM particle size) using a gradient from 2% acetonitrile, 1.5% phosphoric acid (solvent A) to 48% acetonitrile, 1.5% phosphoric acid (solvent B). The following solvent gradient is applied: 0–5 min 100% solvent A; 5–20 min linear gradient of 0–100% solvent B; 21–25 min 100% solvent A. Arbutin was detected at 221 nm absorbance wavelength and quantitated using calibration curves generated with a commercially available standard of arbutin.

Figure 5:
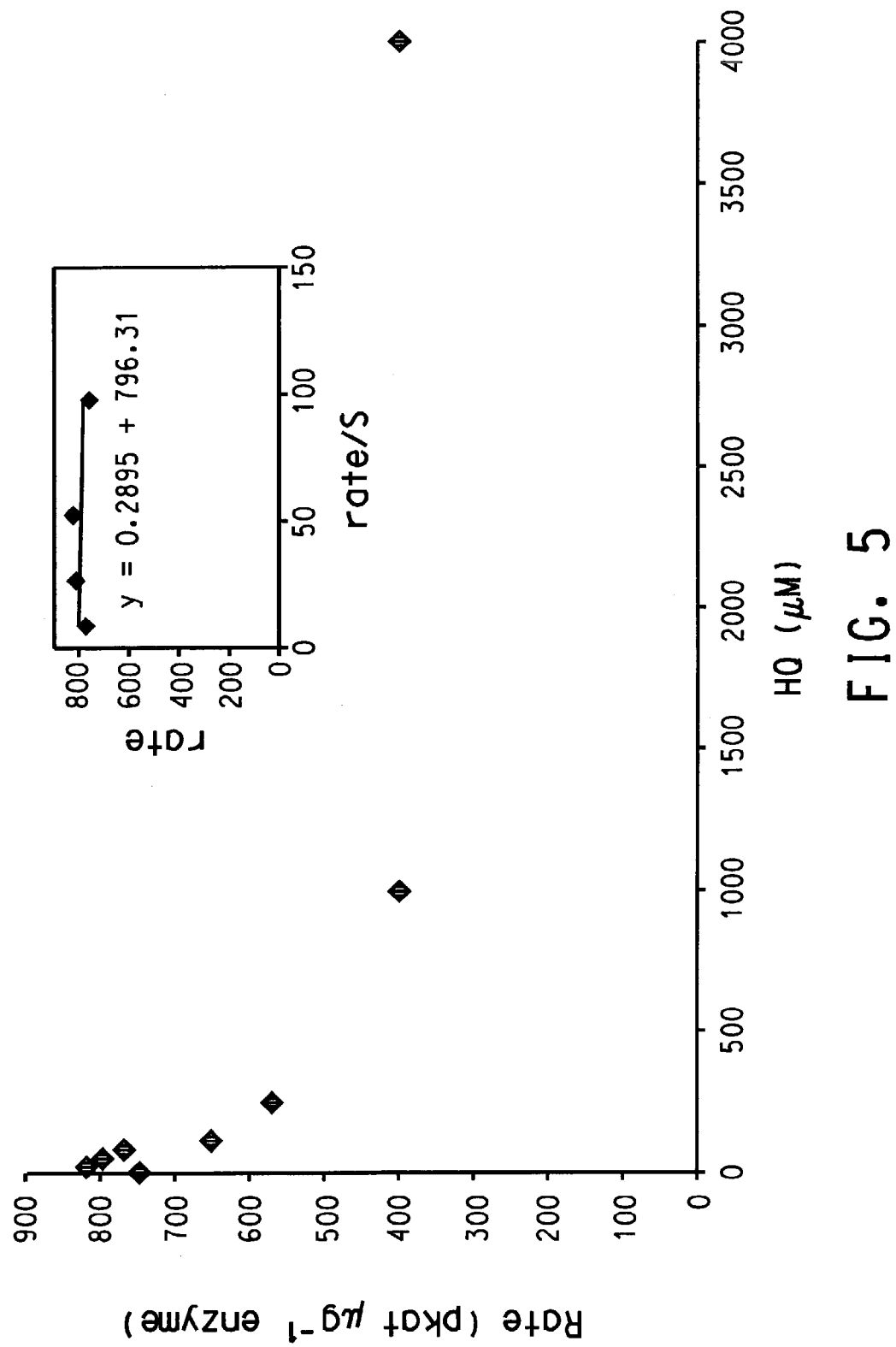
FIG. 5 shows a kinetic analysis of the purified recombinant UGT72B1 protein with hydroquinone as a substrate. Initial rates of product formation are plotted against substrate concentration.

The data was fitted to the Michaelis-Menten equation. Under these conditions, apparent Km and Vmax values were ~0.3 µM and, ~796 pmol/sec/µg, respectively. These parameters were determined using the Hofstee plot by plotting velocity/substrate concentration versus velocity using velocities determined at hydroquinone concentrations of 7.8, 15.6, 31.25, and 62.5 µM (FIG. 5). In this plot, an estimate of the Km is provided as the slope of the line representing the linear regression curve through the points and the Vmax by the intercept of the regression curve with the y axis. FIG. 5 shows a Michaelis-Menten plot of the enzyme assay data. The figure shows that the enzyme is subject to significant substrate inhibition at hydroquinone concentrations of greater than 100 µM.

The Vmax of the UGT72B1 enzyme with hydroquinone is significantly (~68 fold) higher than the Vmax value determined with the UGT72B1 enzyme and benzoic acid substrates (Lim et al., *J. Bio. Chem.*, 277(1):586–592 (2002)). The Vmax of the UGT72B1 enzyme for hydroquinone represents a turnover number of 42/sec at 37° C. This turnover number was calculated using a molecular weight of the UGT72B1 enzyme of 53,015.33 Da calculated with the PEPIDESORT software package of the GCG. This turnover number was significantly higher than the turnover number of the *Rauwolfia serpentina* arbutin synthase that was reported to have a Vmax of 26.32 pkat/µg at 50° C. in the presence of 1 mM hydroquinone (Arend et al., *Phytochemistry*, 53:187–193 (2000)). This Vmax can be converted into a turnover number of ~1.4/sec at 50° C. using 51,793.01 Da as molecular weight of the arbutin synthase protein calculated using GenBank® Accession No. AJ310148.1 and with the PEPIDESORT software package of the GCG.

Applicants disclose the unexpected and unique utility of the UGT72B1 enzyme for conjugation of hydroquinone. The uniqueness of the enzyme is exemplified by a catalytic efficiency expressed as kcat $(s^{-1})$/Km (µM) of 140 that clearly exceeds the efficiency of any other previously disclosed glucosyltransferase enzyme that has activity with hydroquinone.

Example 7

Construction of a Synthetic Operon for Expression of CPL, pHBA 1-H and *Arabidopsis* HQ-GT in *E coli*

A plasmid is constructed that expresses a polycistronic transcript allowing for translation of all three enzymes required to produce of arbutin in *E. coli* from a single transcription unit. The cloning strategy to accomplish this is outlined in FIG. 6. Plasmid DNA of the pET24a construct harboring the CPL gene of *E. coli* (SEQ ID NO:29) is linearized by restriction digestion with SalI and XhoI. The linearized plasmid DNA is combined with two restriction fragments, each containing a ribosome binding site and the open reading frames for the pHBA 1-hydroxylase and ara-

*bidopsis* glucosyltransferase genes, respectively. Restriction fragments for both genes are created as follows:

Plasmid DNA of the pET29A construct for recombinant production of the pHBA 1-hydroxylase protein described in Example 3 is used in a PCR reaction using primers 19 (SEQ ID NO:43) and 20 (SEQ ID NO:44).

```
Primer 19 - (SEQ ID NO:43):
5'-gtcgacAAGGAGATATACATATGGCGGTGCAGGC-3'

Primer 20 - (SEQ ID NO:44):
5'-gtcgacAAGCTTAGCCTGATGCACTTAATGG-3'
```

The underlined nucleotides in caps correspond to the sequence of the pET29A construct for recombinant expression of pHBA 1-hydroxylase. Nucleotides in small caps introduce SalI restriction sites at the 5' and 3' end of the PCR product, respectively. The sequence in bold corresponds to the ribosome-binding site for efficient translation in *E. coli*.

A PCR reaction mixture (100 μL) containing 2.5 mM $MgCl_2$, 2 mM dNTPs, 10 mM Tris/HCl (pH 8.8), 50 mM KCl, 0.08% Nonidet P40, 1 μM of Primer 19 and Primer 20, 10 U Taq® polymerase, and 100 ng of pET29A-pHBA 1-H DNA template is combined. PCR is carried out for 25 cycles, each cycle comprising 45 sec at 94° C., 45 sec at 58° C., and 2 min at 72° C. PCR products are gel-purified and cloned into the pCR2.1 vector using the TOPO T/A cloning kit according to manufacturer's instructions. Recombinant clones are grown in LB medium containing 50 mg/L kanamycin. Plasmid DNA is isolated and subjected to DNA sequencing. Plasmid DNA devoid of PCR-induced mutations is digested with SalI. The 1.4 kb SalI restriction fragment representing the pHBA 1-hydroxylase gene is gel purified.

Plasmid DNA of the pET28A construct for recombinant production of the hydroquinone glucosyltransferase protein of *arabidopsis* described in Example 6 is used in a PCR reaction using primers 21 (SEQ ID NO:45) and 22 (SEQ ID NO:46).

```
Primer 21 - (SEQ ID NO:45):
5'-gtcgacAAGGAGATATACCATGGAGGAATCC-3'

Primer 22 - (SEQ ID NO:46):
5'-ctcgagTTAGTGGTTGCCATTTTGCTCTAACTC-3'
```

The underlined nucleotides correspond to the sequence of the pET28A construct for recombinant expression of the hydroquinone glucosyltransferase protein from *arabidopsis* described as previously described. Nucleotides in small caps introduce SalI and XhoI restriction sites at the 5' and 3' end of the PCR product, respectively. The sequence in bold corresponds to the ribosome-binding site for efficient translation in *E. coli*.

A PCR reaction mixture (100 μL) containing 2.5 mM $MgCl_2$, 2 mM dNTPs, 10 mM Tris/HCl (pH 8.8), 50 mM KCl, 0.08% Nonidet P40, 1 μM of Primer 21 and Primer 22, 10 U Taq® polymerase, and 100 ng of pET28A-HQ GT DNA template is combined. PCR is carried out for 25 cycles, each cycle comprising 45 sec at 94° C., 45 sec at 58° C., and 2 min at 72° C. PCR products are gel-purified and cloned into the pCR2.1 vector using the TOPO T/A cloning kit according to manufacturer's instructions. Recombinant clones are grown in LB medium containing 50 mg/L kanamycin. Plasmid DNA is isolated and subjected to DNA sequencing. Plasmid DNA devoid of PCR-induced mutations is sequentially digested with SalI and XhoI. The 1.4 kb SalI/XhoI restriction fragment representing the HQ GT enzyme is gel-purified.

A ligation reaction is assembled in a final volume of 5 μL comprised of 100 ng of the SalI XhoI linearized, gel-purified, pET24a-CPL DNA and 50 ng each of the SalI pHBA 1-hydroxylase and the SalI/XhoI hydroquinone GT fragment. Ligation products are introduced into electro-competent DH10B cells (Invitrogen, USA) according to the manufacturer's instructions. Recombinant clones are recovered on LB media containing 50 mg/L kanamycin and grown in liquid LB media under selective conditions. Plasmid DNA is isolated and subjected to diagnostic restriction digests with XbaI. Plasmid clones containing all three genes in the orientation illustrated in FIG. 6 are used to produce a pET24a vector fragment of 5 kb and a fragment of 3.2 kb comprised of CPL, pHBA 1-H, and 1.2 kb of the HQ-GT gene. The sequence of the DNA insert of the pET24a vector construct for coexpression of CPL, pHBA 1-H, and HQ-glucosyltransferase proteins is set forth as SEQ ID NO:47.

For arbutin production facilitated by co-expression of CPL, pHBA 1-H, and HQ-glucosyltransferase enzymes in *E. coli*, the pET24a plasmid construct described above is introduced into an *E. coli* host expressing T7 RNA polymerase under the control of an inducible promoter. A suitable host with this property is *E. coli* BL21 DE3 (Novagen, WI, USA). In this strain, expression of the T7 polymerase is under the control of the lacUV5 promoter. The plasmid is introduced into the expression host by electroporation. Transformants are selected on LB medium containing 50 mg/L kanamycin.

To produce arbutin from glucose, a single colony of the BL21DE3 host harboring the arbutin production plasmid is used to inoculate 100 mL of sterile M9 medium (per liter: 6 g $Na_2HPO_4$, 3 g $KH_2PO_4$, 2 g glucose, 1 g $NH_4Cl$, 1 mM $MgSO_4$, 1 mM thiamine, and 0.1 mM $CaCl_2$) containing 50 mg/L kanamycin. Cells are grown under continuous shaking (250 rpm) at 25° C. to an $OD_{600\ nm}$ of 0.6 and arbutin production is induced by adding of IPTG to a final concentration of 0.25 mM. After 24 h, arbutin concentration in the culture medium and *E. coli* cells is determined as follows. Culture (1 mL) is harvested by centrifugation. The culture supernatant is subjected to HPLC analysis as described below. The cell pellet is resuspended in 50 μL of water. The cellular contents are extracted by supplementing the aqueous cell suspension with an equal volume of 100% MeOH. The cell suspension is cleared by centrifugation and both culture medium and methanolic cell extract are subjected to HPLC analysis as follows: 10 μL of analyte are separated on a Nova-Pak® C18 column (60 Å pore size, 4 μM particle size) using a gradient from 2% acetonitrile, 1.5% phosphoric acid (solvent A) to 48% acetonitrile, 1.5% phosphoric acid (solvent B) and UV detection at 282 nm. The following solvent gradient is applied: 0–5 min 100% solvent A; 5–20 min linear gradient of 0–100% solvent B; 21–25 min 100% solvent A. Arbutin is detected at 282 nm absorbance wavelength and quantitated using calibration curves generated with a commercially available standard of arbutin (Sigma).

Generation of Plasmid Vectors that Allow Co-expression of CPL, pHBA 1-hydroxylase, and Hydroquinone Glucosyltransferase at Levels Suitable for Highest Arbutin Productivity.

The DNA construct previously described expresses all three genes required for arbutin production from a single plasmid under the control of the same, very strong T7 promoter. Further advances in the art of arbutin production resulting in improvements of arbutin yield and titer need to take into account the differences in catalytic efficiency of the enzymes required for arbutin production. For example, catalytic efficiency (expressed as Kcat ($s^{-1}$)/Km ($\mu M$)) of the three enzymes required for conversion of chorismate to arbutin is 0.083, 32, and 140 for CPL, pHBA 1-H, and *arabidopsis* HQ GT enzymes, respectively. Thus, the latter two enzymes of the arbutin synthesis pathway can be expressed at significantly lower levels than CPL without affecting flux, thereby alleviating detrimental effects associated with high levels of protein expression. This rationale does not take into account possible differences in the stability of the three enzymes in the *E. coli* cytoplasm. In any case, fine-tuning of expression levels of the enzymes for improved product formation in *E. coli* requires the ability to independently regulate expression levels of the three enzymes used in the arbutin pathway. The expression level of a heterologous gene in *E. coli* is controlled by both copy number of the plasmid and strength of the promoter.

Applicants describe construction of two compatible plasmids pMPMT3 pHBA 1-H and pCL1920 HQ GT in which expression of the pHBA 1-H gene and the HQ GT gene is under the control of the lac promoter. This promoter is weaker than the T7 promoter. Furthermore, the p15a ori of pMPMT3 (10–12 copies/cell) (Mayer et al., *Gene*, 163: 41–46 (1995)) and pSC101 ori of pCL 1920 (5 copies/cell) (Lerner and Inouye, *NAR*, 18(15):4631 (1990)) results in a copy number per cell that is significantly lower than that of the pET24 vector used above. Both promoter strength and plasmid copy number of the new expression plasmids will lead to expression of pHBA 1-H and HQ-GT genes that is significantly lower than that of the CPL gene in the pET24a vector, thereby taking into account the dramatic differences in efficiency of the three catalysts of the proposed arbutin pathway.

A pMPMT3-derived plasmid is created that expresses the pHBA 1-H gene under the control of the lac promoter. Plasmid DNA of the pET29A construct used for recombinant production of the pHBA 1-hydroxylase protein described in Example 3 is used in a PCR reaction using primers 23 (SEQ ID NO:48) and 24 (SEQ ID NO:49).

```
Primer 23 - (SEQ ID NO:48):
5'-ggtaccGTGAAAGGAGATATACATATGGCGGTGCAGGC-3'

Primer 24 - (SEQ ID NO:49):
5'-gagctcAAGCTTAGCCTGATGCACTTAATGG-3'
```

The underlined nucleotides in caps correspond to the sequence of the pET29A construct for recombinant expression of pHBA 1-hydroxylase. Nucleotides in small caps introduce KpnI and SacI restriction sites at the 5' and 3' end of the PCR product, respectively. The sequence in bold corresponds to the ribosome-binding site for efficient initiation of translation in *E. coli*. The sequence in bold italics is a stop codon that terminates translation from the initiator methionine of the β-galactosidase α-fragment gene of the pMPMT3 vector.

A PCR reaction mixture (100 μL) containing 2.5 mM $MgCl_2$, 2 mM dNTPs, 10 mM Tris/HCl (pH 8.8), 50 mM KCl, 0.08% Nonidet P40, 1 μM of Primer 23 and Primer 24, 10 U Taq® polymerase, and 100 ng of pET29A-pHBA 1-H DNA template is combined. PCR is carried out for 25 cycles, each cycle comprising 45 sec at 94° C., 45 sec at 58° C., and 2 min at 72° C. PCR products are gel-purified and cloned into the pCR2.1 vector using the TOPO T/A cloning kit according to manufacturer's instructions. Recombinant clones are grown in LB medium containing 50 mg/L kanamycin. Plasmid DNA is isolated and subjected to DNA sequencing. Plasmid DNA devoid of PCR-induced mutations is digested with KpnI and SacI. The 1.4 kb restriction fragment representing the pHBA 1-hydroxylase gene is gel purified and ligated to the pMPMT3 vector that has been digested with KpnI and SacI restriction enzymes. Ligation products are transformed into electro-competent DH10B cells (Invitrogen) and transformants are selected on LB media containing 10 g/L tetracycline. Plasmid DNA is isolated using standard protocols.

A pCL1920-derived plasmid is created that expresses the *arabidopsis* HQ-GT gene under the control of the lac promoter. Plasmid DNA of the pET28A construct for recombinant production of the glucosyltransferase (UGT72B1) protein described in Example 6 is used in a PCR reaction using primers 25 (SEQ ID NO:50) and 26 (SEQ ID NO:51).

```
Primer 25 - (SEQ ID NO:50):
5'-ggatccGTGAAAGGAGATATACCATGGAGGAATCC-3'

Primer 26 - (SEQ ID NO:51):
5'-aagcttTTAGTGGTTGCCATTTTGCTCTAACTC-3'
```

The underlined nucleotides in caps correspond to the sequence of the pET28A construct for recombinant expression of the UGT72B1 glucosyltransferase. Nucleotides in small caps introduce BamHI and HindIII restriction sites at the 5' and 3' end of the PCR product, respectively. The sequence in bold corresponds to the ribosome-binding site for efficient initiation of translation in *E. coli*. The sequence in bold italics is a stop codon that terminates translation from the initiator methionine of the β-galactosidase α-fragment gene of the pCL1920 vector.

A PCR reaction mixture (100 μL) containing 2.5 mM $MgCl_2$, 2 mM dNTPs, 10 mM Tris/HCl (pH 8.8), 50 mM KCl, 0.08% Nonidet P40, 1 μM of Primer 25 and Primer 26, 10 U Taq® polymerase, and 100 ng of pET28A-UGT72B1 DNA template is combined. PCR is carried out for 25 cycles, each comprising 45 sec at 94° C., 45 sec at 58° C., and 2 min at 72° C. PCR products are gel-purified and cloned into the pCR2.1 vector using the TOPO T/A cloning kit according to manufacturer's instructions. Recombinant clones are grown in LB medium containing 50 mg/L kanamycin. Plasmid DNA is isolated and subjected to DNA sequencing. Plasmid DNA devoid of PCR-induced mutations is digested with BamHI and HindIII. The 1.4 kb restriction fragment representing the UGT72B1 gene is gel-purified and ligated to the pMPMT3 vector that has been digested with BamHI and HindIII restriction enzymes. Ligation products are transformed into electro-competent DH10B cells (Invitrogen) and transformants are selected on LB media containing 50 mg/L spectinomycin. Plasmid DNA is isolated using standard protocols.

For arbutin production facilitated by co-expression of CPL, pHBA 1-H, and HQ-glucosyltransferase enzymes in *E. coli*, the pET24a CPL (Example 4), pMPMT3 pHBA 1-H, and pCL1920 HQ-GT plasmid vectors are introduced into an *E. coli* host expressing T7 RNA polymerase under control of an inducible promoter. A suitable host with this property is *E. coli* BL21 DE3 (Novagen). In this strain expression of the T7 polymerase is under the control of the lacUV5 promoter. The plasmids are simultaneously introduced into the expression host by electroporation. Transformants are selected on LB medium containing 50 mg/L kanamycin, 50 mg/L spectinomycin, and 10 mg/L tetracycline.

To produce arbutin from glucose, a single colony of the BL21DE3 host harboring the three arbutin production plasmids is used to inoculate 100 mL of sterile M9 medium (per liter: 6 g $Na_2HPO_4$, 3 g $KH_2PO_4$, 2 g glucose, 1 g $NH_4Cl$, 1 mM $MgSO_4$, 1 mM thiamine, and 0.1 mM $CaCl_2$) containing 50 mg/L kanamycin, 50 mg/L spectinomycin and 10 mg/L tetracycline. Cells are grown under continuous shaking (250 rpm) at 25° C. to an $OD_{600\ nm}$ of 0.6, and arbutin production is induced by adding IPTG to a final concentration of 1 mM. After 24 h, arbutin concentration in the culture medium and *E. coli* cells is determined as follows. Culture (1 mL) is harvested by centrifugation. The culture supernatant is subjected to HPLC analysis as described below. The cell pellet is resuspended in 50 µL of water and cellular contents are extracted by supplementing the aqueous cells suspension with an equal volume of 100% MeOH. The cell suspension is cleared by centrifugation and both culture medium and methanolic cell extract are subjected to HPLC analysis as follows: 10 µL of analyte are separated on a Nova-Pak® C18 column (60 Å pore size, 4 µM particle size) using a gradient from 2% acetonitrile, 1.5% phosphoric acid (solvent A) to 48% acetonitrile, 1.5% phosphoric acid (solvent B) and UV detection at 282 nm. The following solvent gradient is applied: 0–5 min 100% solvent A; 5–20 min linear gradient of 0–100% solvent B; 21–25 min 100% solvent A. Arbutin is detected at 282 nm absorbance wavelength and quantitated using calibration curves generated with a commercially available standard of arbutin (Sigma).

Example 8

Construction of a Synthetic Operon for Expression of CPL and pHBA 1-H in *E coli*

A plasmid was constructed that expresses a polycistronic transcript allowing for translation of the enzymes required to produce hydroquinone in *E. coli* from a single transcription unit. Plasmid DNA of the pET29a vector was linearized by restriction digestion with NdeI and XhoI. The linearized plasmid DNA was combined with two restriction fragments carrying CPL and pHBA 1-hydroxylase genes. Restriction fragments for both genes are created as follows:

A single colony of *E. coli* BL21 DE3 was used in a PCR reaction using primers 27 (SEQ ID NO:52) and 28 (SEQ ID NO:53).

```
Primer 27 - (SEQ ID NO:52):
5'-CTACTCATTTcatatgTCACACCCCGCGTTAA-3'

Primer 28 - (SEQ ID NO:53):
5'-CATCTTACTgtcgacTTAGTACAACGGTGACGCC-3'
```

The underlined nucleotides in caps correspond to the *E. coli* CPL gene sequence. Nucleotides in small caps introduce NdeI and SalI restriction sites at the 5' and 3' end of the PCR product, respectively.

A PCR reaction mixture (100 µL) containing 2.5 mM $MgCl_2$, 2 mM dNTPs, 10 mM Tris/HCl (pH 8.8), 50 mM KCl, 0.08% Nonidet P40, 1 µM of Primer 27 and Primer 28, 10 U Taq® polymerase was combined and supplemented with *E coli* cells from a single colony of BL21DE3 cells. PCR was carried out for 25 cycles, each cycle comprising 45 sec at 94° C., 45 sec at 58° C., and 2 min at 72° C. PCR products were gel-purified and cloned into the pCR2.1 vector using the TOPO T/A cloning kit according to manufacturer's instructions. Recombinant clones were grown in LB medium containing 50 mg/L kanamycin. Plasmid DNA was isolated and subjected to DNA sequencing. Plasmid DNA devoid of PCR-induced mutations is digested with NdeI and SalI. The 0.49 kb restriction fragment representing the pHBA 1-hydroxylase gene was gel purified.

Plasmid DNA of the pET29A construct for recombinant production of the pHBA 1-hydroxylase protein described in Example 3 was used in a PCR reaction using primers 19 (SEQ ID NO:43) and 20 (SEQ ID NO:44).

A PCR reaction mixture (100 µL) containing 2.5 mM $MgCl_2$, 2 mM dNTPs, 10 mM Tris/HCl (pH 8.8), 50 mM KCl, 0.08% Nonidet P40, 1 µM of Primer 19 and Primer 20, 10 U Taq® polymerase, and 100 ng of pET29A-pHBA 1-H DNA template was combined. PCR was carried out for 25 cycles, each cycle comprising 45 sec at 94° C., 45 sec at 58° C., and 2 min at 72° C. PCR products were gel-purified and cloned into the pCR2.1 vector using the TOPO T/A cloning kit according to manufacturer's instructions. Recombinant clones were grown in LB medium containing 50 mg/L kanamycin. Plasmid DNA was isolated and subjected to DNA sequencing. Plasmid DNA devoid of PCR-induced mutations was digested with SalI. The 1.4 kb SalI restriction fragment representing the pHBA 1-hydroxylase gene was gel purified.

A ligation reaction was assembled in a final volume of 5 µL comprised of 100 ng of the NdeI XhoI linearized, gel-purified pET29a DNA and 50 ng each of the NdeI SalI and SalI restriction fragments corresponding to CPL and pHBA 1-hydroxylase gene, respectively. Ligation products were introduced into electro-competent DH10B cells according to instructions of the manufacturer.

Recombinant clones were recovered on LB media containing 50 mg/L kanamycin and grown in liquid LB media under selective conditions. Plasmid DNA was isolated and subjected to diagnostic restriction digests with XbaI and HindIII which excises a 2 kb restriction fragment containing CPL and pHBA 1-hydroxylase genes. The sequence of the DNA insert comprised of CPL and pHBA 1-hydroxylase genes is set forth as SEQ ID NO:54.

Production of hydroquinone or arbutin from glucose in *E. coli* was achieved as follows. The polycistronic construct for arbutin production described above and the construct for expression of the hydroquinone-specific glucosyltransferase described in Example 6 were independently introduced into cells of the *E. coli* host BL21DE3. In this strain expression of the T7 polymerase is under the control of the lacUV5 promoter. Transformants were selected on LB medium containing 50 mg/L kanamycin. To produce arbutin from glucose, single colonies of the BL21DE3 hosts harboring either CPL and pHBA 1-Hydroxylase or the HQ-GT gene were used to inoculate 50 mL of sterile M9 medium (per liter: 6 g $Na_2HPO_4$, 3 g $KH_2PO_4$, 2 g glucose, 1 g $NH_4Cl$, 1 mM $MgSO_4$, 1 mM thiamine, and 0.1 mM $CaCl_2$, adjusted to pH 6 with phosphoric acid) containing 50 mg/L kanamycin. Cells were grown under continuous shaking (300 rpm) at 37° C. to an $OD_{600\ nm}$ of 0.6. Cells were harvested by centrifugation and resuspended in 5 mL of M9 medium.

Hydroquinone production in *E. coli* was achieved by combining the harvested cells of two 50 mL cultures containing the CPL/pHBA 1-hydroxylase construct in 100 mL of fresh M9 medium containing 25 mg/L kanamycin and 0.5 mM IPTG. Cells were grown under continuous shaking (300 rpm) at 26° C. for 14 h.

Arbutin production in *E. coli* was achieved by combining the harvested cells of 50 mL cultures containing either the CPL/pHBA 1-hydroxylase or the HQ-GT construct in 100 mL of fresh M9 medium containing 25 mg/L kanamycin and 0.5 mM IPTG. Cells were grown under continuous shaking (300 rpm) at 26° C. for 14 h.

For control purposes, a third culture that only contained cells harboring the HQ-GT construct was set up under identical conditions.

The culture was cleared by centrifugation and subjected to HPLC analysis as follows: 10 μL of culture supernatant were separated on a Nova-Pak® C18 column (60 Å pore size, 4 μM particle size) using a gradient from 1.5% acetonitrile, 1.5% phosphoric acid (solvent A) to 48% acetonitrile, 1.5% phosphoric acid (solvent B) and UV detection at 221 nm. The following solvent gradient was applied: 0–5 min 100% solvent A; 5–20 min linear gradient of 0–100% solvent B; 21–25 min 100% solvent A. Arbutin and hydroquinone were detected at 221 nm absorbance wavelength and quantified using calibration curves generated with commercially available standards.

Figure 7:
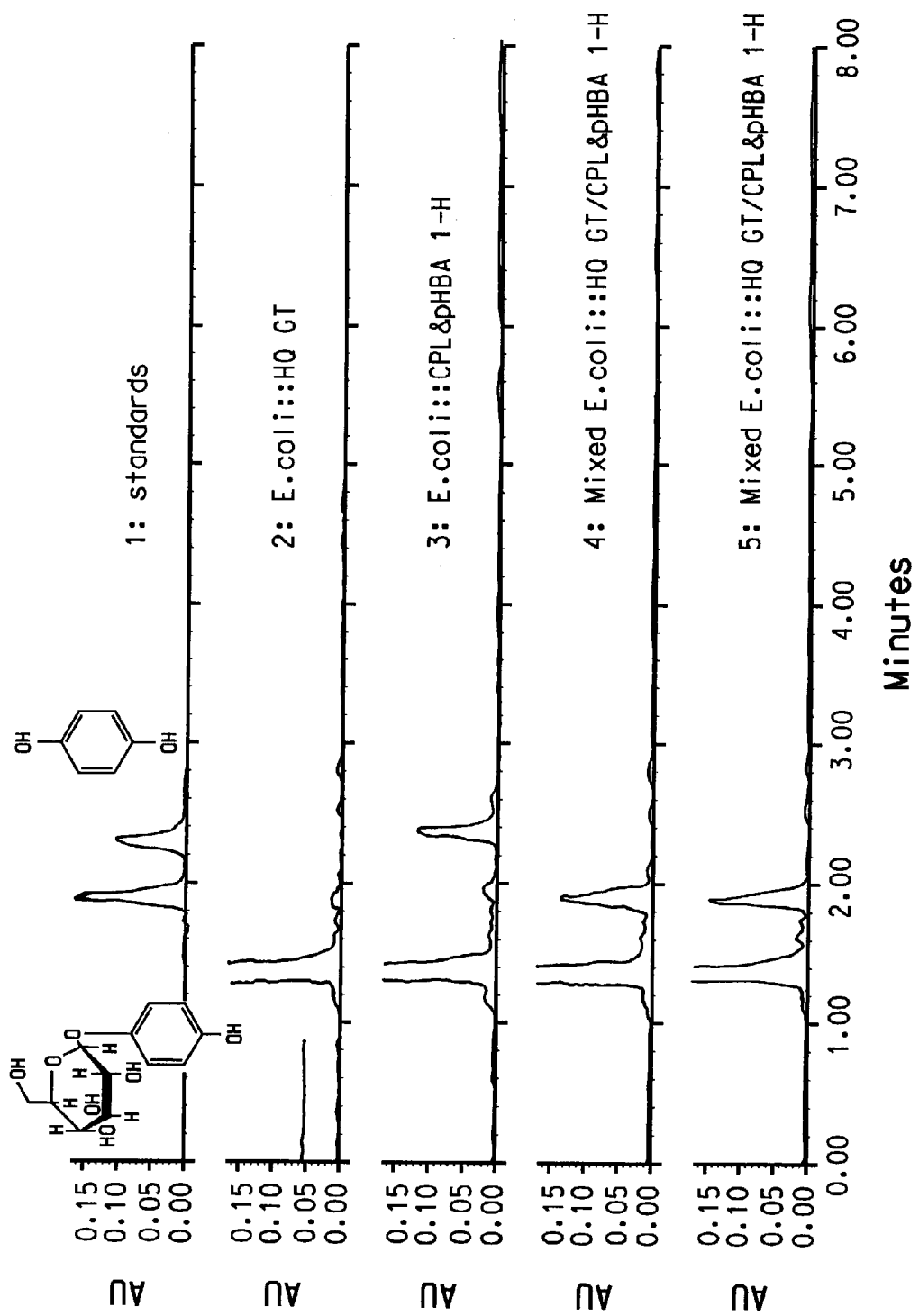
FIG. 7 shows the results of HPLC analysis of medium from *E. coli* cultures expressing CPL, pHBA 1-hydroxylase, and hydroquinone-specific glucosyltransferase enzymes.

FIG. 7 shows HPLC traces illustrating the composition of the medium of $E.$ $coli$ cultures. Comparison of trace 1 and trace 3 reveals that co-expression of CPL and pHBA 1-hydroxylase leads to production of a new compound with a retention time that is identical to that of the hydroquinone standard. Moreover, comparison of trace 1 and trace 4/5 reveals that when cultures expressing CPL and pHBA 1-hydroxylase and HQ-GT are mixed and enzyme production induced by adding IPTG, the putative hydroquinone intermediate is converted to a new compound with a retention time identical to that of arbutin. Identity of the microbially-produced arbutin was confirmed by LC-MS analysis as follows. 100 microliters of the cell-free culture supernatant were separated by HPLC as described above and the putative arbutin peak was collected manually. The purified arbutin was analyzed by LC-MS. 100 μL of the HPLC-purified compound was injected onto a ZORBAX Eclipse XDB-C18 column (2.1×150 mm, 80 Å, 3.5 μm) (Bio-RAD, USA). The column was developed under the following conditions: Solvent A ($H_2O$/0.1% (v/v) formic acid), Solvent B (100% acetonitrile); 0–25 min 0%–60% B (0.3 mL/min), 25–25.5 min 60–100% B (0.4 mL/min), 25.5–30 min 100% B (0.4 mL/min), 30–31 min 100%–0% B (0.3 mL/min), and 31–40 min 0% B (0.3 mL/min). A Hewlett-Packard mass spectrometer MSD1100 equipped with a electrospray interface was used to detect analytes. Data was acquired in positive ion mode with a capillary voltage of 3 kV. The desolvation gas flow was 12 L/min of nitrogen. The desolvation and the source block temperatures were 350° C. The instrument was tuned for unit resolution. Data was collected by scanning from 80–600 daltons in 1 sec for MS experiments.

The medium of a mixed $E.$ $coli$ culture of cells expressing CPL and pHBA 1-hydroxylase and cells expressing a hydroquinone-specific glucosyltransferase from $arabidopsis$ contained a new compound. When analyzed by mass spectroscopy, the new compound produced a molecular ion in electrospray positive ionization mode that exhibited a mass to charge ratio (m/z+) of 290.1. The properties of this molecular ion are in very close agreement with the expected m/z+ of the ammonium adduct (MW 290.29) of hydroquinone glucoside (MW 272.25). Moreover, the compound consistently produced a fragment of m/z+=180.0 which is in close agreement with the expected m/z+ for glucose (MW=180.16).

The culture medium of $E.$ $coli$ BL21 DE3 cells expressing CPL and pHBA 1-hydroxylase enzymes contained 29.3 mg/L hydroquinone after 14 h of fermentation. The medium of a mixed culture of $E.$ $coli$ BL21 DE3 cells expressing CPL and pHBA 1-hydroxylase and HQ-GT enzyme contained 63.5 mg/L arbutin after 14 h of fermentation. Further improvements to arbutin accumulation in $E.$ $coli$ cultures will be achieved by expressing all three enzymes required for arbutin production in a single cell as described in Example 7.

What is claimed is:

1. A method for producing hydroquinone glucoside in a green plant comprising:
   a) growing a green plant under suitable conditions, the green plant having
      i) an endogenous source of chorismate;
      ii) a nucleic acid fragment encoding active para-hydroxybenzoic acid 1-hydroxylase enzyme at least 95% identical to the amino acid sequence set forth in SEQ ID NO:23; and
      iii) an endogenous source of hydroquinone glucosyltransferase; and
      iv) a chorismate pyruvate lyase expression cassette having the structure:

P-T-C-D-CPL wherein
      P is a promoter suitable for driving the expression of a chorismate pyruvate lyase gene; T is a nucleic acid molecule encoding a Rubisco chloroplast transit peptide; C is a nucleic acid molecule encoding a Rubisco chloroplast transit peptide cleavage site; and D is a nucleic acid molecule encoding four contiguous amino acids of the N-terminal portion of a Rubisco chloroplast transit peptide donor polypeptide; CPL is a nucleic acid molecule encoding chorismate pyruvate lyase enzyme having the amino acid sequence set forth in SEQ ID NO:30; and P, T, C, D, and CPL are operably linked with each other; and
   b) recovering the hydroquinone glucoside produced in step a).

2. A method for producing hydroquinone glucoside in a green plant comprising:
   a) growing a green plant cell under suitable conditions, the green plant having
      i) an endogenous source of chorismate;
      ii) a nucleic acid fragment encoding active para-hydroxybenzoic acid 1-hydroxylase enzyme at least 95% identical to the amino acid sequence set forth in SEQ ID NO:23; and
      iii) a nucleic acid fragment encoding an active hydroquinone glucosyltransferase enzyme at least 95% identical to the amino acid sequence set forth in SEQ ID NO: 42; and
      iv) a chorismate pyruvate lyase expression cassette having the structure:

P-T-C-D-CPL wherein
      P is a promoter suitable for driving the expression of a chorismate pyruvate lyase gene; T is a nucleic acid molecule encoding a Rubisco chloroplast transit peptide; C is a nucleic acid molecule encoding a Rubisco chloroplast transit peptide cleavage site; and D is a nucleic acid molecule encoding four contiguous amino acids of the N-terminal portion of a Rubisco chloroplast transit peptide donor polypeptide; CPL is a nucleic acid molecule encoding chorismate pyruvate lyase enzyme at least 95% identical to the amino acid sequence set forth in SEQ ID NO:30; and P, T, C, D, and CPL are operably linked with each other; and
   b) recovering the hydroquinone glucoside from the green plant produced in step a).

3. The method of claims 1 or 2 wherein the promoter is selected from the group consisting of the nopaline synthase promoter, the octopine synthase promoter, cauliflower mosaic virus 35S promoter, the ribulose-1,5-bisphosphate carboxylase promoter, and the promoter of the chlorophyll a/b binding protein.

4. The method of claims 1 or 2 wherein the Rubisco transit peptide is derived from tobacco, Arabidopsis, sugar beet, sugar cane, soybean, rapeseed, sunflower, cotton, corn, alfalfa, wheat, barley, oats, sorghum, rice, canola, millet, beans, peas, rye, flax, or forage grasses.

5. The method of claims 1 or 2 wherein the green plant cell is selected from the group consisting of tobacco, Arabidopsis, sugar beet, and sugar cane.

6. The method of claim 2 wherein the chorismate lyase expression cassette encodes a polypeptide having an amino acid sequence as set forth in SEQ ID NO:30.

7. The method according to claims 1 or 2 wherein the hydroquinone glucoside recovered in step (b) is more than 10% per dry weight of plant leaf biomass.

8. The method of claims 1 or 2 wherein the hydroquinone glucoside recovered in step (b) is more than 15% per dry weight of plant leaf biomass.

9. The method of claims 1 or 2 wherein the hydroquinone glucoside recovered in step (b) is more than 20% per dry weight of plant leaf biomass.

10. A transgenic green plant comprising a nucleic acid fragment encoding active para-hydroxybenzoic acid 1-hydroxylase enzyme having an amino acid sequence at least 95% identical to the amino acid sequence set forth in SEQ ID NO:23.

11. The transgenic green plant of claim 10 further comprising a nucleic acid fragment encoding active hydroquinone glucosyltransferase enzyme having an amino acid sequence at least 95% identical to the amino acid sequence set forth in SEQ ID NO:42.

12. The transgenic green plant of claims 10 or 11 wherein the host green plant is selected from the group consisting of tobacco, *Arabidopsis*, sugar beat, and sugar cane.

* * * * *